(12) United States Patent
Hidaka et al.

(10) Patent No.: US 6,403,607 B1
(45) Date of Patent: Jun. 11, 2002

(54) SULFONAMIDE DERIVATIVES AND DRUGS CONTAINING THE SAME AS THE ACTIVE INGREDIENT

(75) Inventors: Hiroyoshi Hidaka, 607, Otokikiyama, Tenpaku-ku, Nagoyai-shi, Aichi 468-0063; Tsutomu Inoue, Funabashi; Isao Umezawa, Tokyo; Hiroyuki Nakano, Machida; Hiroshi Nakamura, Nagareyama; Naofumi Watanabe, Inagi; Shizumasa Yokota, Tsurugashima; Tomomitsu Sasaki, Ageo; Yumi Yajima, Matsudo, all of (JP)

(73) Assignee: Hiroyoshi Hidaka, Nagoya (JP)

( * ) Notice: Subject to any disclaimer, the term of this patent is extended or adjusted under 35 U.S.C. 154(b) by 0 days.

(21) Appl. No.: 09/647,533

(22) PCT Filed: Mar. 30, 1999

(86) PCT No.: PCT/JP99/01621

§ 371 (c)(1),
(2), (4) Date: Oct. 2, 2000

(87) PCT Pub. No.: WO99/50237

PCT Pub. Date: Oct. 7, 1999

(30) Foreign Application Priority Data

Mar. 30, 1998 (JP) ............................................. 10-083804

(51) Int. Cl.[7] ........................ A61K 31/47; A61K 31/34; A61K 31/535; C07D 217/22; C07D 40/100
(52) U.S. Cl. .................... 514/309; 514/461; 514/231.2; 514/231.5; 546/141; 546/142; 546/167
(58) Field of Search .................... 564/80, 81; 546/294, 546/141, 60, 167, 142; 544/128; 549/67, 429; 548/251; 514/187, 461, 231.2, 231.5, 309

(56) References Cited

FOREIGN PATENT DOCUMENTS

| WO | WO 9420467 | * | 9/1994 |
| WO | 43-12966 A1 | * | 10/1994 |

* cited by examiner

*Primary Examiner*—Alan L. Rotman
*Assistant Examiner*—Binta Robinson
(74) *Attorney, Agent, or Firm*—Oblon, Spivak, McClelland, Maier & Neustadt, P.C.

(57) ABSTRACT

The present invention discloses a sulfonamide derivative represented by the following formula (1):

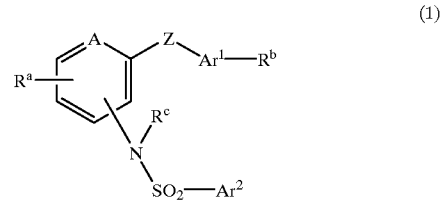

[wherein A represents a nitrogen atom, —CH=, etc.; Z represents an oxygen atom, etc.; $Ar^1$ represents an aryl group, etc.; $Ar^2$ represents an alkyl group, etc.; $R^a$ represents a hydrogen atom, etc.; $R^b$ represents a hydrogen atom, etc.; and $R^c$ represents an alkyl group, etc.], or a salt thereof; and drugs containing the derivative or a salt thereof as an active ingredient.

This compound exhibits radical scavenging action, gastric mucous secretion augmenting action, and anti-HP action, and thus is effective as a peptic ulcer therapeutic agent.

8 Claims, No Drawings

SULFONAMIDE DERIVATIVES AND DRUGS CONTAINING THE SAME AS THE ACTIVE INGREDIENT

TECHNICAL FIELD

The present invention relates to a novel sulfonamide derivative exhibiting excellent effects in the treatment of peptic ulcer and a drug comprising the derivative as an active ingredient.

BACKGROUND ART

Drug therapy for peptic ulcers has been founded on two essential approaches based on Shay's Balance Theory; inhibition of aggressive factors and potentiation of defensive factors. On the basis of such balance theory, peptic ulcers have been treated for a long time using inorganic drugs such as antacids or by mucosal protective drugs such as isoprene compounds. In the 1980s, a guanidine derivative was developed as an $H_2$-receptor antagonist (hereinafter referred to as "$H_2$-RA"), an acid secretion inhibitory drug which acts immediately and exhibits a high cure rate as compared with conventional drugs. In addition, in the 1990s, a sulfinylbenzimidazole derivative was developed as a proton pump inhibitor (hereinafter referred to as "PPI") which is an acid secretion inhibitory drug having different active sites. PPIs exhibited excellent inhibitory gastric acid secretion as compared with $H_2$-RAs. In addition, PPIs were reported to exhibit protective effects on the mucosa and to also eliminate *Helicobacter pylori* (hereinafter referred to as "HP") which is considered to be a cause of peptic ulcer recurrence. Therefore, the development of peptic ulcer remedies was thought to have reached a culmination.

However, since both $H_2$-RAs and PPIs, which were generally expected to successfully address the treatment of peptic ulcers, have become widely used, it has become apparent that ulcers frequently recur at a high recurrence ratio after $H_2$-RAs is withdrawn when ulcers are thought be cured. In addition, it has been reported that when a PPI is used continuously, hyperplasia of enterochromaffin-like cells, hypergastrinemia, or gastric carcinoid may occur. Therefore, the amount of PPI to be administered has been restricted. Meanwhile, it has been pointed out that an $H_2$-RA or PPI exhibits insufficient or no anti-HP effect when used as monotherapy, and thus it has been proposed that an $H_2$-RA or PPI be used in combination with an antibacterial drug such as clarithromycin. On the basis of this proposition, clinical trials have been carried out using an $H_2$-RA or PPI in combination with a variety of antibacterial drugs. However, such combination therapy for peptic ulcer has not yet become generally established, since the level of elimination of HP does not increase commensurately with the number of drugs employed; a high dose of an antibacterial drug is required; side effects may develop; and resistant bacteria may occur. In addition, peptic ulcer therapy using an $H_2$-RA or PPI in combination with two types of antibacterial drugs, i.e., triple therapy, has also been proposed. However, at the present time, a peptic ulcer remedy exhibiting significant anti-HP effects has not been developed. $H_2$-RAs or PPIs also have such disadvantages as a correlation between free radicals thereof and lesions of the gastric mucosa. Therefore, although $H_2$-RAs or PPIs exhibit a gastric acid secretion inhibitory effect, both are unsatisfactory as peptic ulcer remedies.

In view of the foregoing, an object of the present invention is to provide a compound which exhibits a gastric acid secretion inhibitory effect, anti-HP effect, and a gastric mucus secretion potentiating effect, and which is useful as a peptic ulcer remedy.

DISCLOSURE OF THE INVENTION

The present inventors have performed extensive studies, focusing on aromatic sulfonamide compounds, and have found that a sulfonamide derivative, represented by the following formula (1), exhibits an excellent gastric acid secretion inhibitory effect, anti-HP effect, and gastric mucus secretion potentiating effect as compared with aminobenzyl derivatives disclosed in the patent application previously filed by the present inventors (Japanese Patent Application Laid-Open (kokai) No. 6-72979), and that the sulfonamide derivative is useful as a peptic ulcer remedy. The present invention has been accomplished on the basis of these findings.

Accordingly, the present invention provides a sulfonamide derivative represented by the following formula (1):

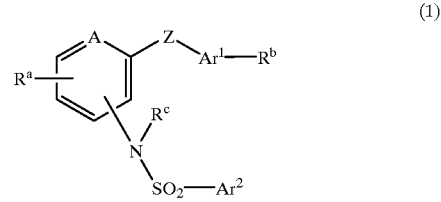

(1)

[wherein A represents a nitrogen atom or a group —$C(R^1)$=;

Z represents a single bond, an oxygen atom, a sulfur atom, an imino group, —$N(R^2)$—$(CH_2)_n$—, —$N(R^2)$—$(CH_2)_n$—$N(R^3)$—, —$N(R^2)$—$(CH_2)_n$—O—, —$N(R^2)$—$(CH_2)$—S—, —$N(R^2)$—$(CH_2)_n$—$NHSO_2$—, —$N(R^2)$—$CH_2CH=CH$—, —$O(CH_2)_n$—$N(R^3)$—, or —$N(R^2)$—$(CH_2)_n$—O—$CH_2$—;

$Ar^1$ represents an aromatic hydrocarbon group, or a saturated or unsaturated heterocyclic group;

$Ar^2$ represents a phenyl group, an alkyl group, a naphthyl group, a quinolyl group, an isoquinolyl group, a thienyl group, or a pyridyl group, which may have one through three substituents selected from among a halogen atom, an alkyl group, an alkoxy group, an acetamido group, and a nitro group;

$R^a$ represents a hydrogen atom, a morpholinoyl group, an alkoxy group, or an aminoalkoxy group;

$R^b$ represents a hydrogen atom, a halogen atom, an alkyl group, or an alkoxy group;

$R^c$ represents a hydrogen atom, or an alkyl group or a halogenobenzenesulfonyl group, which may have a substituent;

$R^1$ represents a hydrogen atom, or $R^1$ and $R^2$ together form a trimethylene group;

$R^2$ represents a hydrogen atom, an alkyl group, a dialkylaminoalkyl group, a benzyl group, a halogenophenyl group, or a halogenobenzenesulfonyl group, $R^2$ and $R^1$ together form a trimethylene group, or $R^2$ and $R^3$ together form an ethanedioyl group or an alkylene group;

$R^3$ represents a hydrogen atom, an alkyl group, a hydroxyoxalyl group, an alkanoyl group, a sulfonyl group, an alkoxycarbonyl group, or a halogenobenzenesulfonyl group, or $R^3$ and $R^2$ together form an ethanedioyl group or an alkylene group;

n is a number of 2–4; and

Z is not —N($R^2$)—$CH_2$—CH=CH— when $Ar^2$ is an isoquinolyl group], or a salt thereof.

The present invention also provides a drug comprising, as an active ingredient, a sulfonamide derivative represented by formula (1) or a salt thereof.

The present invention also provides a pharmaceutical composition comprising a sulfonamide derivative represented by formula (1) or a salt thereof and a pharmaceutically acceptable carrier therefor.

The present invention also provides use of a sulfonamide derivative represented by formula (1) or a salt thereof as a drug.

The present invention also provides a method for treating peptic ulcer comprising administration of an effective dose of a sulfonamide derivative represented by formula (1) or a salt thereof.

BEST MODE FOR CARRYING OUT THE INVENTION

In formula (1), A represents a nitrogen atom or a group —C($R^1$)=. When A is a nitrogen atom, a pyridine ring is formed; when $R^1$ is a hydrogen atom, a benzene ring is formed; and when $R^1$ and $R^2$ together form a trimethylene group, a tetrahydroquinoline ring is formed.

In a group represented by Z in formula (1), a halogen atom of a halogenophenyl group or a halogenobenzenesulfonyl group represented by $R^2$ or $R^3$ may be a fluorine atom, a chlorine atom, a bromine atom, or an iodine atom. In $R^2$ and $R^3$, the alkyl group or the alkyl moiety of the dialkylaminoalkyl group is preferably a C1–C4 alkyl group. Specific examples include a methyl group, an ethyl group, an n-propyl group, an i-propyl group, an n-butyl group, an i-butyl group, a sec-butyl group, and a t-butyl group. Of these, a methyl or ethyl group is preferable, and a methyl group is more preferable. An alkoxy moiety of an alkoxycarbonyl group is preferably a C1–C4 alkoxy group. Specific examples include a methoxy group, an ethoxy group, an n-propoxy group, an i-propoxy group, an n-butoxy group, an i-butoxy group, a sec-butoxy group, and a t-butoxy group. Of these, a t-butoxy group is preferable; and a t-butoxycarbonyl group is preferable as an alkoxycarbonyl group. Examples of alkylene groups formed by $R^2$ and $R^3$ include a methylene group, an ethylene group, and a trimethylene group. Of these, an ethylene group or a trimethylene group is preferable.

A number n of a group represented by Z is 2 to 4, but 2 or 3 is preferable.

Z specifically represents a single bond, an oxygen atom, a sulfur atom, an imino group (—NH—), —N($R^2$)—$(CH_2)_2$—, —N($R^2$)—$(CH_2)_3$—, —N($R^2$)—$(CH_2)_2$—N($R^3$)—, —N($R^2$)—$(CH_2)_3$—N($R^3$)—, —N($R^2$)—$(CH_2)_2$—O—, —N($R^2$)—$(CH_2)_3$—O—, —N($R^2$)—$(CH_2)_2$—S—, —N($R^2$)—$(CH_2)_3$—S—, —N($R^2$)—$(CH_2)_2$—$NHSO_2$—, —N($R^2$)—$CH_2$—CH=CH—, —O$(CH_2)_2$—N($R^3$)—, —O$(CH_2)_3$—N($R^3$)—, or —N($R^2$)—$(CH_2)_2$—O—$CH_2$—.

Examples of ethanedioyl and alkylene groups formed by $R^2$ and $R^3$ include the following groups.

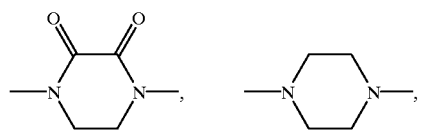

-continued

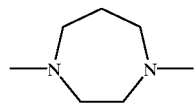

When $Ar^2$ is an isoquinolyl group, Z is not —N($R^2$)—$CH_2$—CH=CH—.

In formula (1), the aromatic hydrocarbon group represented by $Ar^1$ may be a phenyl group or a naphthyl group, but a phenyl group is preferable. A heterocyclic group may be saturated or unsaturated. A hetero atom of the heterocyclic group may be a nitrogen atom, an oxygen atom, or a sulfur atom. Specific examples of the heterocyclic group include a pyridyl group, a thienyl group, a furyl group, a pyrimidyl group, an indolyl group, an imidazolyl group, a cumalinyl group, a phthalimidyl group, a quinolyl group, a tetrazolyl group, a triazolyl group, an oxazolyl group, a thiazolyl group, a thiadiazolyl group, a morpholino group, and a piperazino group. Of these, a morpholino group or a piperazino group is preferable. When Z is a single bond, $Ar^1$ is preferably a morpholino group or a piperazino group.

In $Ar^2$ in formula (1), the alkyl group is preferably a C1–C20 alkyl group. Specific examples include a methyl group, an ethyl group, an n-propyl group, an i-propyl group, an n-butyl group, an i-butyl group, a sec-butyl group, a t-butyl group, an n-pentyl group, an i-pentyl group, an n-hexyl group, an i-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-eicosyl group. Of these, a C1–C8 alkyl group is preferable. A substituent of a phenyl group may be an alkyl group similar to that as described above, but is preferably a C1–C4 alkyl group, more preferably a methyl group or an ethyl group. A halogen atom may be a fluorine atom, a chlorine atom, a bromine atom, or an iodine atom. An alkoxy group is preferably a C1–C4 alkoxy group. Specific examples include a methoxy group, an ethoxy group, an n-propoxy group, an i-propoxy group, an n-butoxy group, an i-butoxy group, a sec-butoxy group, and a t-butoxy group. Of these, a methoxy group is preferable.

In formula (1), the alkoxy group or the alkoxy moiety of the aminoalkoxy group represented by $R^a$ or an alkoxy group represented by $R^b$ is preferably a C1–C4 alkoxy group. Specific examples include a methoxy group, an ethoxy group, an n-propoxy group, an i-propoxy group, an n-butoxy group, an i-butoxy group, a sec-butoxy group, and a t-butoxy group. The alkyl group represented by $R^b$ or $R^c$ is preferably a C1–C8 alkyl group. Specific examples include a methyl group, an ethyl group, an n-propyl group, an i-propyl group, an n-butyl group, an i-butyl group, a sec-butyl group, a t-butyl group, an n-pentyl group, an i-pentyl group, an n-hexyl group, an i-hexyl group, an n-heptyl group, an i-heptyl group, an n-octyl group, and an i-octyl group. Of these, $R^b$ is preferably a methyl group, and $R^c$ is preferably a methyl group, an ethyl group, or an n-propyl group. The halogen atom represented by $R^b$ or the halogen atom moiety of the halogenobenzenesulfonyl group represented by $R^c$ may be a fluorine atom, a chlorine atom, a bromine atom, or an iodine atom.

The alkyl group represented by $R^c$ may have a substituent. Examples of substituents include an amino group; a dialkylamino group (preferably, a di-$C_{1-4}$ alkylamino group such as a dimethylamino group or a diethylamino group); an aminoalkoxy group (preferably, an amino-$C_{1-4}$ alkoxy group); a dialkylaminoalkoxy group (preferably, di-$C_{1-4}$ alkylaminoalkoxy group); a heterocyclic group such as a pyrilidino group, a pyridyl group, a piperidino group, a piperazino group, a morpholino group, or an imidazolyl group; a hydroxyl group; a 2-cyano-3-$C_{1-4}$ alkylguanidino group; a $C_{1-4}$ alkoxyoxalylamino-$C_{1-4}$ alkoxy group; a $C_{3-6}$ cycloalkylureido-$C_{1-4}$ alkoxy group; a guanidino group; a halogenophenyloxy group; a $C_{1-4}$ alkoxycarbonylamino group; a halogen atom; a mono-$C_{1-4}$ alkylamino group; a hydroxy-$C_{1-4}$ alkylamino group; and a $C_{1-4}$ alkoxycarbonylamino-$C_{1-4}$ alkoxy group. A $C_{1-4}$ alkyl group in these substituents may be a methyl group, an ethyl group, an n-propyl group, an i-propyl group, an n-butyl group, an i-butyl group, a sec-butyl group, or a t-butyl group. A $C_{1-4}$ alkoxy group in these substituents may be a methoxy group, an ethoxy group, an n-propoxy group, an i-propoxy group, an n-butoxy group, an i-butoxy group, a sec-butoxy group, or a t-butoxy group.

$R^c$ is preferably an alkyl group having a substituent selected from among an amino group, a dialkylamino group, an aminoalkoxy group, a dialkylaminoalkoxy group, a heterocyclic group, and a hydroxy group.

In formula (1) representing a sulfonamide derivative, Z is preferably —NH(CH$_2$)$_n$O—, —NH(CH$_2$)$_n$NH, =N(CH$_2$)$_n$N=, =N(CH$_2$)$_n$O—, or an oxygen atom. $Ar^1$ is preferably a phenyl group. $Ar^2$ is preferably a halogenophenyl group, more preferably a chlorophenyl group. $R^a$ is preferably a hydrogen atom. $R^b$ is preferably a halogen atom, more preferably a chlorine atom. $R^c$ is preferably a dimethylaminoethyl group, an aminoethoxyethyl group, a piperidylethyl group, an aminopentyl group, a hydrogen atom, a pyrrolidylethyl group, or an aminoethyl group.

The salt of the sulfonamide derivative (1) of the present invention is not particularly limited, so long as the salt is pharmaceutically acceptable. Examples of preferred salts include salts of alkali metal and alkaline earth metal such as sodium salts, potassium salts, and calcium salts; hydrogen halide salts such as hydrogen fluorides, hydrochlorides, hydrogen bromides, and hydrogen iodides; inorganic salts such as carbonates, nitrates, perchlorates, sulfates, and phosphates; lower alkylsulfonates such as methanesulfonates, trifluoromethanesulfonates, and ethanesulfonates; arylsulfonates such as benzenesulfonates and p-toluenesulfonates; organic acid salts such as fumarates succinates, citrates, tartrates, oxalates, and maleates; and amino acid salts such as glutamates and aspartates.

The present invention encompasses hydrates, a variety of pharmaceutically acceptable solvates, and crystal forms of the sulfonamide derivative.

The sulfonamide derivative (1) of the present invention may be produced through, for example, the following process (1).

Process 1

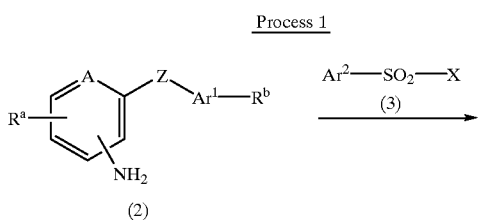

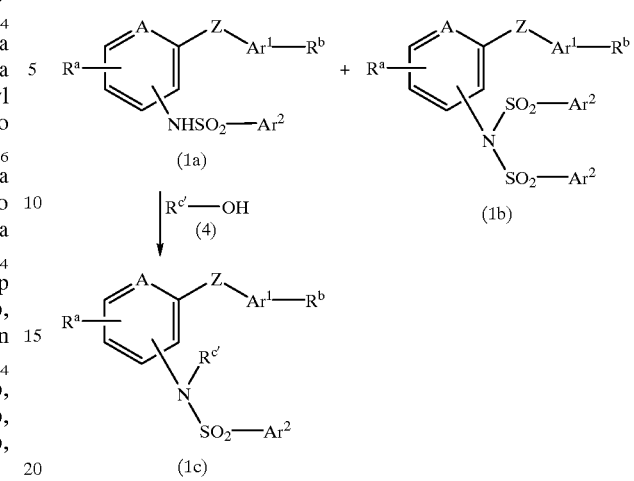

(wherein X represents a halogen atom, $R^c$ represents an alkyl group which may have a substituent, and A, Z, $Ar^1$, $Ar^2$, $R^a$, and $R^b$ are the same as described above).

Briefly, when an amine compound (2) is reacted with a sulfonyl halide (3), a monosulfonamide (1a) and a disulfonamide (1b) are obtained. Subsequently, when a monosulfonamide (1a) is reacted with an alcohol (4), a compound (1c) is obtained.

In the process, the reaction between the compound (2) and the sulfonyl halide (3) is preferably carried out in the presence of a base such as pyridine in a manner similar to the reaction of customary acid amid formation. In the process, the reaction between the compound (1a) and the alcohol (4) may be carried out through the Mitsunobu process by use of triphenylphosphine and diisopropylazo dicarboxylate. However, the reaction is preferably carried out through a customary process; i.e., a reaction between a halogenated alcohol and an alkali metal salt of amide, or a reaction between a sulfonated alcohol and an alkali metal salt of amide.

The amine compound (2) serving as a raw material in the process can be produced as follows. The group $R^b$—$Ar^1$—Z— is introduced into phenylenediamine, nitrobenzene, or nitropyridine, serving as a raw material, and then the nitro group of the resultant compound is reduced to an amino group.

Of sulfonamide derivatives (1) of the present invention, compounds in which Z and $R^a$ moieties have special structures may be produced as follows:

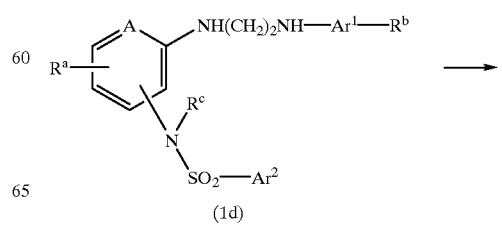

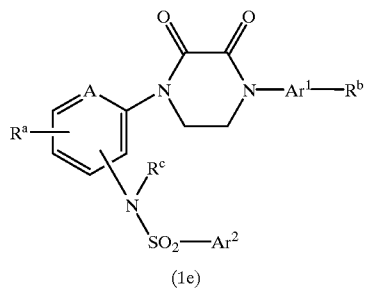

(wherein A, $Ar^1$, $Ar^2$, $R^a$, $R^b$, and $R^c$ are the same as described above).

When a compound (1d) is reacted with oxalyl chloride, a compound (1e) in which Z is a piperazinedione structure.

A variety of salts of the thus-produced compound of the present invention can be obtained through a conventional process.

The sulfonamide derivative of the present invention exhibits a gastric acid secretion inhibitory effect, anti-ulcer effect, radical scavenging effect, gastric mucus secretion potentiating effect, and anti-HP effect, and thus the derivative is effectively employed as a peptic ulcer remedy.

A drug comprising the sulfonamide derivative (1) of the present invention may be administered orally or parenterally. The drug may be formed into a variety of products including oral administration forms such as powders, granules, tablets, sugar-coated tablets, and capsules; subcutaneous, intramuscular, or intravenous injections; and suppositories.

The aforementioned drug products may be produced by use of the sulfonamide derivative (1) singly, or by use of the derivative in an appropriate combination with pharmaceutically acceptable carriers such as excipients, expanders, binders, wetting agents, disintegrating agents, surfactants, lubricants, dispersants, buffers, preservatives, sweetening agents, perfumes, and coating agents.

The dose of the thus-produced drug of the present invention varies depending on the disease to be treated, symptoms, or administration route. One daily dose of the drug for an adult is usually 3–1,000 mg as reduced to the sulfonamide derivative (1), preferably 10–500 mg. The aforementioned daily dose is preferably administered in divided portions 1–4 times a day.

EXAMPLES

The present invention will next be described in more detail by way of examples, which should not be construed as limiting the invention thereto.

Referential Example 1

N-[2-(4-Chlorophenoxy)ethyl]-o-phenylenediamine

Under stirring on ice, carbon tetrabromide (57.7 g) in tetrahydrofuran (50 ml) was added dropwise over 30 minutes to a tetrahydrofuran solution (100 ml) containing 2-(4-chlorophenoxyethanol) (30 g) and triphenylphosphine (45.5 g). After completion of exothermic reaction, the solution was stirred at room temperature for one hour, and the precipitate was removed by filtration. The solvent was removed by evaporation under reduced pressure. Ether was added to the residue, followed by stirring at room temperature. The sediment that precipitated was removed by filtration, and the solvent was evaporated under reduced pressure. The procedure of filtering off and evaporation under reduced pressure was repeated until no sediment came to precipitate. The thus-obtained oily matter was dissolved in toluene (200 ml), and o-phenyldiamine (51.92 g) was added thereto, followed by refluxing for 16 hours. The reaction mixture was cooled to room temperature. Subsequently, chloroform was added thereto and insoluble matter was removed by filtration. The solvent was removed by evaporation under reduced pressure. The residue was purified by means of silica gel chromatography (solvent=hexane:ethyl acetate=5:1) and subsequently re-crystallized from ethyl acetate-hexane, to thereby yield the target product (30.7 g) in the form of white crystals.

Mp.: 95–97° C.; $^1$H-NMR (270 MHz, CDCl$_3$) δ: 7.23 (2H, d, J=8.91 Hz), 6.85 (2H, d, J=8.91 Hz), 6.81 (1H, m) 6.73 (3H, m), 4.17 (2H, t, J=4.94 Hz), 3.50 (2H, t, J=4.94 Hz).

Example 1

N-[2-(4-Chlorophenoxy)ethyl]-N'-(4-chlorobenzenesulfonyl)-o-phenylenediamine

The product of Referential Example 1 (30.7 g) was dissolved in pyridine (100 ml). To the resultant solution, 4-chlorobenezensulfonyl chloride was added dropwise over 30 min with stirring on ice. The mixture was stirred at room temperature for another 30 min. Excessive pyridine was removed under reduced pressure, and ethyl acetate (300 ml) was added so as to dissolve the residue. The thus-obtained solution was washed sequentially with water, 2N HCl, a saturated sodium hydrogencarbonate solution, and saturated brine, in this order, and dehydrated over anhydrous sodium sulfate so as to remove the solvent, The resultant product was allowed to stand overnight, and the thus-obtained crystals were re-crystallized from ethyl acetate-hexane, to thereby yield the target product (46.8 g) in the form of white crystals.

Mp.: 142–143° C.; $^1$H-NMR(270 MHz, CDCl$_3$) δ: 7.67 (2H, d, J=8.91 Hz), 7.39 (2H, d, J=8.91 Hz), 7.24 (2H, d, J=8.91 Hz) 7.15 (1H, m), 6.86 (2H, d, J=8.91 Hz), 6.80 (1H, d, J=7.92 Hz), 6.56 (2H, m), 6.17 (1H, brs), 4.09 (2H, t, J=5.28 Hz), 3.49 (2H, t, J=5.28 Hz), Example 2

N-(4-Chlorobenzenesulfonyl)-N-(2-dimethylaminoethyl)-N'-[2-(4-chlorophenoxy)ethyl]-o-phenylenediamine The product of Example 1 (10.71 g), triphenylphosphine (9.63 g), and dimethylaminoethanol (3.27 g) were dissolved in tetrahydrofuran (60 ml). To the resultant solution diisopropyl azodicarboxylate (7.43 g) was added dropwise over 30 min with stirring on ice. After completion of dropwise addition of the solution, the mixture was further stirred for one hour at room temperature and the solvent was removed under reduced pressure. The residue was purified through two steps: NH silica gel column chromatography (solvent=hexane:ethyl acetate=3:1,) and silica gel column chromatography (solvent=hexane:ethyl acetate=1:1 and chloroform:methanol=10:1). The resultant product was re-crystallized from ether-hexane, to thereby obtain the target product (7.42 g) in the form of crystals. Mp.: 99° C.; $^1$H-NMR(270 MHz, CDCl$_3$) δ: 7.65 (2H, d, J=8.58 Hz), 7.41 (2H, d, J=8.58 Hz), 7.25 (2H, d, J=8.91 Hz), 7.18 (1H, m), 6.87 (2H, d, J=8.91 Hz), 6.72 (1H, d, J=8.25 Hz), 6.47 (2H, m), 5.78 (1H, brs), 4.08 (3H, m), 3.51 (2H, m), 3.12 (1H, m), 2.42 (1H, m), 2.22 (1H, m), 2.20 (6H, s).

Example 3

N-(4-Chlorobenzenesulfonyl)-N-(2-dimethylaminoethyl)-N'-[2-(4-chlorophenoxy)ethyl]-o-phenylenediamine ½ Tartaric Acid Salt The product of Example 2 (30 g) and tartaric acid (8.94 g) were dissolved in pre-heated purified water (1176 ml).

The resultant solution was filtrated under reduced pressure and stirred moderately overnight at room temperature. The crystals that precipitated were collected through filtration and washed with purified water. Subsequently, the crystals were air-dried for 4 days at room temperature and further dried for 8 hours under reduced pressure, to thereby obtain the target product (34.3 g) in the form of white crystals.

Mp.: 84–86° C.; $^1$H-NMR(270 MHz, DMSO-d$_6$) δ: 7.72 (2H, d, J=8.58 Hz), 7.62 (2H, d, J=8.58 Hz), 7.36 (2H, d, J=8.91 Hz), 7.18 (1H, m), 7.00 (2H, d, J=8.91 Hz), 6.78 (H, d, J=8.24 Hz), 6.48 (2H, m), 4.18 (1H, s), 4.10 (2H, t, J=5.28 Hz). 4.00 (1H, m), 3.46 (2H, t, J=5.28 Hz), 3.18 (1H, m), 2.35 (1H, m), 2.22(1H, m, 1H), 2.18 (6H, s).

By the employment of different types of alcohol of Example 2, the following products were obtained.

Example 4
N-[2-(2-Aminoethoxy)ethyl]-N-(4-chlorobenzenesulfonyl)-N'-[2-(4-chlorophenoxy)ethyl]-o-phenylenediamine Tartaric Acid Salt $^1$H-NMR(270 MHz, CDCl$_3$) δ: 7.64 (2H, d, J=8.58 Hz), 7.43 (2H, d, J=8.58 Hz), 7.23 (2H, d, J=8.90 Hz) 7.16~7.19 (1H, m), 6.87 (2H, d, J=8.91 Hz), 6.76 (1H, d, J=8.24 Hz), 6.52 (H, t, J=7.26 Hz), 6.41 (1H, d, J=7.92 Hz), 5.16 (1H, br), 4.00~4.13 (2H, ), 3.56 (2H, q, J=5.61 Hz), 3.26~3.47 (5H, m), 2.74 (2H, t, J=5.28 Hz).

Example 5
NN-(4-Chlorobenzenesulfonyl)-N-[2-(2-dimethylamino)ethoxyethyl]-N'-[2-(4-chlorophenoxy)ethyl]-o-phenylenediamine $^1$H-NMR(270 MHz, CDCl$_3$) δ: 7.34 (2H, d, J=8.58 Hz), 7.26 (4H, s), 6.84 (2H, d, J=8.91 Hz), 6.59 (1H, t, J=7.58 Hz), 6.49 (1H, d, J=7.92 Hz), 6.38 (1H, t, J=7.59 Hz), 4.07 (1H, brt, J=5.28 Hz), 4.07 (2H, t, J=5.31 Hz), 3.64~3.68 (4H, br), 3.49~3.51 (2H, m), 3.23 (6H, s), 3.18~3.22 (3H, m).

Example 6
N-(4-Chlorobenzenesulfonyl)-N-(3-aminopropyl)-N'-[2-(4-chlorophenoxy)ethyl]-o-phenylenediamine $^1$H-NMR(270 MHz, CDCl$_3$) δ: 7.58 (2H, d, J=8.58 Hz), 7.42 (2H, d, J=8.58 Hz), 7.22 (2H, d, J=9.23 Hz), 7.18 (1H, t, J=8.58 Hz), 6.84 (2H, d, J=9.24 Hz), 6.74 (1H, d, J=7.26 Hz), 6.48 (1H, t, J=7.58 Hz), 6.28 (1H, d, J=7.92 Hz), 5.04 (1H, t, J=5.94 Hz), 4.08 (2H, t, J=5.62 Hz), 3.74~3.80 (1H, m), 3.54 (2H, q, J=5.62 Hz), 3.02~3.08 (1H, m), 2.86 (2H, t, J=7.26 Hz).

Example 7
N-(4-Aminobuthyl)-N-(4-chlorobenzenesulfonyl)-N'-[2-(4-chlorophenoxy)ethyl]-o-phenylenediamine $^1$H-NMR(270 MHz, CDCl$_3$) δ: 7.59 (2H, d, J=8.58 Hz), 7.41 (2H, d, J=8.58 Hz), 7.22 (2H, d, J=9.23 Hz), 7.19 (1H, t, J=7.26 Hz), 6.85 (2H, d, J=9.24 Hz), 6.75 (1H, d, J=7.26 Hz), 6.48 (1H, t, J=6.26 Hz), 6.27 (1H, d, J=7.92 Hz), 5.06 (1H, t, J=6.27 Hz), 4.09 (2H, t, J=5.61 Hz), 3.58~3.80 (1H, m), 3.55 (2H, q, J=5.6, 5.94 Hz), 3.03~3.08 (1H, m), 2.86 (2H, t, J=7.26 Hz), 1.63~1.65 (2H, m), 1.26~1.45 (3H, m).

Example 8
N-(4-Chlorobenzenesulfonyl)-N-[2-(1-pyrolidino)ethyl]-N'-[2-(4-chlorophenoxy)ethyl]-o-phenylenediamine 1H-NMR(270 MHz, CDCl$_3$) δ: 7.65 (2H, d, J=8.58 Hz), 7.41 (2H, d, J=8.25 Hz), 7.24 (2H, d, J=9.56 Hz), 7.18 (1H, t, J=6.6 Hz), 6.86 (2H, d, J=8.91 Hz), 6.73 (1H, d, J=7.92 Hz), 6.42~6.50 (2H, m), 5.71 (1H, brs), 4.00~4.13 (21, m), 3.10~3.19 (1H, m), 2.52~2.66 (3H, m), 2.26~2.37 (3H, m), 1.71 (4H, brs).

Example 9
N-(4-Chlorobenzenesulfonyl)-N-(2-hydroxyethyl)-N'-[2-(4-chlorophenoxy)ethyl]-o-phenylenediamine $^1$H-NMR(270 MHz, CDCl$_3$) δ: 7.64 (2H, d, J=8.58 Hz), 7.45 (2H, d, J=8.58 Hz), 7.24 (2H, d, J=9.24 Hz), 7.18~7.23 (1H, m), 6.88 (2H, d, J=9.24 Hz), 6.82~6.86 (1H, m), 6.61 (1H, t, J=7.59 Hz), 6.32 (1H, d, J=7.91 Hz), 4.11~4.19 (4H, m), 3.64~3.69 (1H, m), 3.55 (1H, br), 3.31~3.39 (1H, m), 3.07~3.20 (2H, m).

Example 10
N-(4-Chlorobenzenesulfonyl)-N-[3-(4-pyridyl)propyl]-N'-[2-(4-chlorophenoxy)ethyl]-o-phenylenediamine $^1$H-NMR(270 MHz, CDCl$_3$) δ: 8.40 (2H, d, J=5.94 Hz), 7.58 (2H, d, J=8.58 Hz), 7.43 (2H, d, J=8.58 Hz), 7.20 (2H, d, J=8.91 Hz), 7.18~7.20 (1H, m), 6.94 (1H, d, J=5.94 Hz), 6.80 (2H, d, J=9.24 Hz), 6.53 (1H, t, J=7.26 Hz), 6.30 (1H, d, J=7.58 Hz), 5.14 (1H, t, J=5.94 Hz), 4.08~4.16 (3H, m), 3.80~3.90 (1H, m), 3.57 (2H, q, J=4.39, 5.6 Hz), 3.06~3.08 (1H, m), 2.53~2.69 (2H, m), 1.65~1.81 (2H, m).

Example 11
N-(2-Aminoethyl)-N-(4-methoxybenzenesulfonyl)-N'-[2-(4-chlorophenoxy)ethyl]-o-phenylenediamine $^1$H-NMR(270 MHz, CDCl$_3$) δ: 7.62 (2H, d, J=8.91 Hz), 7.23 (2H, d, J=8.90 Hz), 7.17 (1H, t, J=7.58 Hz), 6.93 (2H, d, J=8.90 Hz), 6.87 (2H, d, J=8.91 Hz), 6.75 (1H, d, J=8.24 Hz), 6.51 (1H, t, J=7.26 Hz), 6.34 (1H, d, J=7.59 Hz), 4.14 (2H, t, J=5.81 Hz), 3.89~3.97 (1H, m), 3.86 (3H, s), 3.56 (2H, t, J=5.28 Hz), 3.05 3.13 (1H, m), 2.70~2.77 (1H, m), 2.59~2.69 (1H, m).

Example 12
N-(4-Chlorobenzenesulfonyl)-N-[3-(2-pyridyl)ethyl]-N'-[2-(4-chlorophenoxy)ethyl]-o-phenylenediamine $^1$H-NMR(270 MHz, CDCl$_3$) δ: 8.42~8.44 (1H, m), 7.61 (2H, d, J=8.58 Hz), 7.50 (1H, t, J=7.98 Hz), 7.41 (2H, d, J=8.58 Hz), 7.20 (2H, d, J=9.24 Hz), 7.15~7.18 (1H, m), 7.00~7.09 (2H, m), 6.83 (2H, d, J=9.24 Hz), 6.75 (1H, d, J=8.25 Hz), 6.50 (1H, t, J=7.75 Hz), 6.40 (1H, d, J=7.92 Hz), 5.30 (1H, t, J=5.94 Hz), 4.20~4.31 (1H, m), 4.08 (2H, t, J=5.61 Hz), 3.55 (2H, q, J=5.60 Hz), 2.91~3.02 (1H, m), 2.76~2.86 (1H, m).

Example 13
N-(5-Aminopenthyl)-N-(4-chlorobenzenesulfonyl)-N'-[2-(4-chlorophenoxy)ethyl]-o-phenylenediamine $^1$H-NMR(270 MHz, CDCl$_3$) δ: 7.59 (2H, d, J=8.58 Hz), 7.41 (2H, d, J=8.58 Hz), 7.22 (2H, d, J=9.23 Hz), 7.18 (1H, t, J=8.58 Hz), 6.84 (2H, d, J=9.24 Hz), 6.75 (1H, d, J=7.26 Hz), 6.48 (1H, t, J=7.59 Hz), 6.27 (1H, d, J=7.92 Hz), 5.06 (1H, t, J=5.94 Hz), 4.09 (2H, t, J=5.61 Hz), 3.72~3.80 (1H, m), 3.55 (2H, q, J=5.60 Hz), 3.03~3.08 (1H, m), 2.86 (2H, t, J=7.26 Hz), 1.63 1.65 (2H, m), 1.26~1.45 (4H, m).

Example 14
N-(4-Chlorobenzenesulfonyl)-N-[2-(2-cyano-3-methylguanidino)ethoxyethyl]-N'-[2-(4-chlorophenoxy)ethyl]-o-phenylenediamine $^1$H-NMR(270 MHz, CDCl$_3$) δ: 7.60 (2H, d, J=8.58 Hz), 7.43 (2H, d, J=8.58 Hz), 7.25 (2H, d, J=8.91 Hz), 7.17~7.22 (1H, m), 6.86 (2H, d, J=9.24 Hz), 6.76 (1H, d, J=7.25 Hz), 6.54 (1H, t, J=7.26 Hz), 6.42 (1H, d, J=7.92 Hz), 5.82 (1H, brs), 5.74 (1H, brs), 5.06 (1H, t, J=5.94 Hz), 4.01~4.16 (4H, m), 3.25~3.55 (8H, m), 2.82 (3H, d, J=4.95 Hz), 2.79~2.87 (2H, m).

Example 15
N-(4-Chlorobenzenesulfonyl)-N-[2-(2-piperidino)ethyl]-N'-[2-(4-chlorophenoxy)ethyl]-o-phenylenediamine $^1$H-NMR(270 MHz, CDCl$_3$) δ: 7.77~7.85 (1H, m), 7.62 (2H, d, J=8.91 Hz), 7.55 (1H, t, J=4.29 Hz), 7.50~7.54 (2H, m), 7.30~7.46 (2H, m), 7.12~7.30 (3H, m), 6.86 (2H, d, J=5.28 Hz), 6.75 (1H, d, J=8.24 Hz), 6.51 (1H, d, J=15.18 Hz), 6.31 (1H, t, J=6.59 Hz), 5.15 (1H, t, J=5.94 Hz), 4.13 (2H, q, J=5.28 Hz), 3.83~3.98 (1H, m), 3.54 (2H, q, J=5.94 Hz), 3.09~3.17 (1H, m), 2.93~2.98 (1H, m), 2.42~2.52 (2H, m), 1.16~1.83 (8H, m), 0.90~1.03 (1H, m).

Example 16
N-(4-Chlorobenzenesulfonyl)-N-[2-(2-ethoxyoxalylamino)ethoxyethyl]-N'-[2-(4-chlorophenoxy)ethyl]-o-phenylenediamine $^1$H-NMR(270 MHz, CDCl$_3$) δ: 7.64 (2H, d, J=8.58 Hz), 7.46~7.56 (1H, m), 7.44 (2H, d, J=8.58 Hz), 7.24 (2H, d, J=8.90 Hz), 7.16~7.19 (2H, m), 7.87 (2H, d, J=8.91 Hz), 6.75~6.79 (2H, m), 6.53 (1H, t, J=7.59 Hz), 6.40 (1H, d, J=7.92 Hz), 5.10~5.14 (1H, m), 4.38 (2H, q, J=5.16 Hz), 4.02~4.14 (4H, m), 3.53~3.59 (2H, m), 3.40~3.48 (4H, m), 3.26~3.33 (2H, m).

Example 17
N-(4-Chlorobenzenesulfonyl)-N-[2-(2-cyclohexylureido)ethoxyethyl]-N'-[2-(4-chlorophenoxy)ethyl]-o-phenylenediamine $^1$H-NMR(270 MHz, CDCl$_3$) δ: 7.61 (2H, d, J=8.25 Hz), 7.42 (2H, d, J=8.25 Hz), 7.16~7.26 (4H, m), 6.85 (2H, d, J=8.91 Hz), 6.43~6.78 (2H, m), 5.02~5.16 (1H, m), 4.04~4.12 (2H, m), 3.27~3.57 (6H, m), 1.25~1.87(10H, m).

Example 18
N-(4-Chlorobenzenesulfonyl)-N-(2-guanidinoethoxyethyl)-N'-[2-(4-chlorophenoxy)ethyl]-o-phenylenediamine $^1$H-NMR(270 MHz, CDCl$_3$) δ: 7.78 (2H, d, J=8.90 Hz), 7.72 (2H, d, J=8.90 Hz), 7.41 (2H, d, J=9.24 Hz), 7.21~7.27 (1H, m), 7.03 (2H, d, J=8.91 Hz), 6.87 (1H, d, J=8.24 Hz), 6.56 (2H, d, J=3.30 Hz), 4.14~4.18 (2H, m), 3.56 (2H, brt, J=12.86 Hz), 3.45~3.49 (2H, m), 3.28 (1H, br).

Example 19
N-(2-Bromoethyl)-N-(4-chlorobenzenesulfonyl)-N'-[2-(4-chlorophenoxy)ethyl]-o-phenylenediamine $^1$H-NMR(270 MHz, CDCl$_3$) δ: 7:64 (2H, d, J=8.58 Hz), 7.44 (2H, d, J=8.58 Hz), 7.24 (2H, d, J=8.57 Hz), 7.21 (1H, t, J=8.58 Hz), 6.86 (2H, d, J=8.91 Hz), 6.62 (1H, d, J=8.24 Hz), 6.53 (1H, t, J=7.92 Hz), 6.45 (1H, d, J=7.92 Hz), 5.05 (1H, brt, J=5.94, 5.61 Hz), 4.14~4.22 (1H, m), 4.13 (2H, t, J=5.94 Hz), 3.55 (2H, q, J=5.93 Hz), 3.26~3.52 (3H, m).

Example 20
N-[2-(4-Chlorophenoxy)ethyl]-N'-[2-(4-chlorophenoxy)ethyl]-N'-(4-chlorobenzenesulfonyl)-o-phenylenediamine $^1$H-NMR(270 MHz, CDCl$_3$) δ: 7.67 (2H, dm, J=8.6 Hz), 7.44 (2H, dm, J=8.6 Hz), 7.23 (2H, dm, J=8.9 Hz), 7.21 (1H, td, J=7.9, 1.7 Hz), 7.11 (2H, dm, J=8.9 Hz), 6.78 (1H, dd, J=7.6, 1.3 Hz), 6.76 (2H, dm, J=8.9 Hz), 6.62 (2H, dm, J=8.9 Hz), 6.55 (1H, td, J=7.6, 1.3 Hz), 6.44 (1H, dd, J=7.9, 1.7 Hz), 5.0~5.4 (1H, br), 4.24 (1H, dt, J=13.9, 6.2 Hz), 3.82~3.98 (4H, m), 3.52 (1H, dt, J=13.9, 4.9 Hz), 3.37~3.46 (2H, m).

Example 21
N-[2-(2-Amino)ethoxyethyl]-N-(1-butanesulfonyl)-N'-[2-(4-chlorophenoxyethyl]-o-phenylenediamine $^1$H-NMR(270 MHz, CDCl$_3$) δ: 7.22 (2H, d, J=8.4 Hz), 7.14 (1H, t, J=7.59 Hz), 6.84 (2H, d, J=8.91 Hz), 6.78 (1H, d, J=7.91 Hz), 6.71 (1H, t, J=7.92 Hz), 5.18 (1H, brt, J=5.94 Hz), 4.11 (2H, t, J=5.61 Hz), 3.87 (1H, tt, J=5.61, 5.60 Hz), 3.54~3.68 (3H, m), 3.39~3.47 (4H, m), 3.04~3.19 (2H, m), 2.79 (2H, t, J=4.94 Hz), 1.77~1.89 (2H, m), 1.58 (2H, m), 1.35~1.48 (2H, m), 0.92 (3H, t, J=7.59 Hz).

Example 22
N-[2-(2-Amino)ethoxyethyl]-N-(methanesulfonyl)-N'-[2-(4-chloro)phenoxyethyl]-o-phenylenediamine $^1$H-NMR(270 MHz, CDCl$_3$) δ: 7.22 (2H, d, J=8.9 Hz), 7.19~7.22 (1H, m), 7.15 (1H, d, J=7.92 Hz), 6.84 (2H, d, J=8.91 Hz), 6.79 (1H, t, J=6.93 Hz), 5.14 (1H, brt, J=5.94 Hz), 4.11 (2H, t, J=5.61 Hz), 3.70~3.79 (2H, m), 3.58 (2H, q, J=5.94 Hz), 3.41~3.49 (2H, m), 3.02 (3H, s), 2.81 (2H, t, J=5.30 Hz).

Example 23
N-[2-(2-Amino)ethoxyethyl]-N-(1-ethanesulfonyl)-N'-[2-(4-chlorophenoxy)ethyl]-o-phenylenediamine $^1$H-NMR(270 MHz, CDCl$_3$), δ: 7.21 (2H, d, J=8.91 Hz), 7.15~7.19 (1H, m), 6.84 (2H, d, J=8.91 Hz), 5.12 (1H, brt), 4.13 (2H, t, J=5.61 Hz), 3.81~3.90 (1H, m), 3.58~3.71 (5H, m), 3.45~3.49 (2H, m), 3.12 (2H, q, J=7.26 Hz), 3.00~3.05 (2H, m), 1.35 (3H, t, J=7.59 Hz).

Example 24
N-[2-(2-Amino)ethoxyethyl]-N-(1-propanesulfonyl)-N'-[2-(4-chlorophenoxy)ethyl]-o-phenylenediamine $^1$H-NMR(270 MHz, CDCl$_3$) δ: 7.22 (2H, d, J=8.90 Hz), 7.15 (1H, d, J=7.92 Hz), 6.84 (2H, d, J=9.24 Hz), 6.77 (1H, d, J=8.24 Hz), 6.70 (1H, t, J=7.59 Hz), 5.18 (1H, brt, J=5.94 Hz), 4.12 (2H, t, J=5.61 Hz), 3.72~3.89 (1H, m), 3.63~3.69 (1H, m), 3.54~3.60 (2H, m), 3.39~3.47 (3H, m). 3.10 (1H, t, J=7.26 Hz), 3.12 (1H, t, J=8.9 Hz), 2.79 (2H, t, J=5.28 Hz), 1.82~1.96 (2H, m), 1.49 (2H, brs), 1.02 (3H, t, J=7.26 Hz),

Example 25
N-[2-(2-Amino)ethoxyethyl]-N-(2-propanesulfonyl)-N'-[2-(4-chlorophenoxy)ethyl]-o-phenylenediamine $^1$H-NMR(270 MHz, CDCl$_3$) δ: 7.22 (2H, d, J=8.90 Hz), 7.16 (1H, d, J=7.92 Hz), 6.85 (2H, d, J=8.91 Hz), 6.78 (1H, d, J=8.24 Hz), 6.71 (1H, t, J=7.43 Hz), 5.22 (1H, t, J=5.94 Hz), 4.13 (1H, t, J=5.61 Hz), 3.96 4.06 (1H, m), 3.57 (2H, q, J=5.61 Hz), 3.35~3.50 (4H, m), 2.81 (2H, t, J=4.94 Hz), 2.34 (2H, br), 1.40 (6H, dd, J=6.59 Hz).

Example 26
N-[2-(2-Amino)ethoxyethyl]-N-(1-octanesulfonyl)-N'-[2-(4-chlorophenoxy)ethyl]-o-phenylenediamine $^1$H-NMR(270 MHz, CDCl$_3$) δ: 7.22 (2H, d, J=8.9 Hz), 7.14 (1H, d, J=7.92 Hz), 6.84 (2H, d, J=8.91 Hz), 6.75 (1H, d, J=8.24 Hz), 6.70 (1H, t, J=7.92 Hz), 5.18 (1H, t, J=5.94 Hz), 4.11 (2H, t, J=5.61 Hz), 3.82~3.92 (1H, m), 3.54~3.69 (3H, m), 3.37~3.47 (3H, m), 3.06~3.18 (2H, m), 2.79 (2H, t, J=4.95, 5.28 Hz), 1.78~1.89 (2H, m), 1.25~1.40 (10H, m), 0.87 (3H, t, J=6.6 Hz).

Example 27
N-[2-(2-Amino)ethoxyethyl]-N-(1-pentanesulfonyl)-N'-[2-(4-chlorophenoxy)ethyl]-o-phenylenediamine $^1$H-NMR(270 MHz, CDCl$_3$) δ: 7.22 (2H, d, J=8.90 Hz), 7.14 (1H, d, J=7.75 Hz), 6.84 (2H, d, J=8.91 Hz), 6.78 (1H, d, J=8.24 Hz), 6.70 (1H, t, J=7.59 Hz), 5.18 (1H, brt, J=5.94 Hz), 4.11 (2H, t, J=5.61 Hz), 3.82~3.89 (1H, m), 3.54~3.71 (3H, m), 3.39~3.47 (4H, m), 3.08~3.15 (2H, m), 2.79 (2H, t, J=5.28 Hz), 1.79~1.87 (2H, m), 1.55 (2H, br), 1.31~1.38 (3H, m), 0.89 (3H, t, J=7.92 Hz).

Example 28
N-[2-(2-Amino)ethoxyethyl]-N-(1-hexanesulfonyl)-N'-[2-(4-chlorophenoxy)ethyl]-o-phenylenediamine $^1$H-NMR(270 MHz, CDCl$_3$) δ: 7.20 (2H, d, J=7.58 Hz), 7.14 (1H, d, J=7.75 Hz), 6.84 (2H, d, J=8.90 Hz), 6.75 (1H, d, J=8.24 Hz), 6.68 (1H, t, J=7.52 Hz), 5.18 (1H, t, J=5.90 Hz), 4.11 (2H, t, J=5.60 Hz), 3.80~3.92 (1H, m), 3.54~3.68 (3H, m), 3.39~3.46 (4H, m), 3.08~3.15 (2H, m), 2.79 (2H, t, J=5.28 Hz), 1.79~1.89 (2H, m), 1.22~1.42 (7H), 0.88 (3H, t, J=6.93 Hz).

Example 29
N-[2-(2-Amino)ethoxyethyl]-N-(1-heptanesulfonyl)-N'-[2-(4-chlorophenoxy)ethyl]-o-phenylenediamine $^1$H-NMR(270 MHz, CDCl$_3$) δ: 7.20 (2H, d, J=7.59 Hz), 7.14 (1H, d, J=7.75 Hz), 6.84 (2H, d, J=8.91 Hz), 6.75 (1H, d, J=8.24 Hz), 6.70 (1H, t, J=7.51 Hz), 5.18 (1H, t, J=5.94 Hz), 4.11 (2H, t, J=5.61 Hz), 3.82~3.92 (1H, m), 3.54~3.62 (3H, m), 3.39~3.47 (4H, m), 3.06~3.18 (2H, m), 2.79 (2H, t, J=5.28 Hz), 1.78~1.89 (2H, m), 1.20~1.42 (9H, m), 0.87 (3H, t, J=7.26 Hz).

Example 30
N-[2-(Dimethylamino)ethyl]-N-ethanesulfonyl-N'-[2-(4-chlorophenoxy)ethyl]-o-phenylenediamine Hydrochloride $^1$H-NMR(270 MHz, DMSO-d$_6$) δ: 10.75 (1H, br), 7.54~7.65 (2H, m), 7.32 (2H, d, J=9.24 Hz), 7.28~7.33 (1H, m), 7.22 (1H, t, J=8.24 Hz), 6.97 (2H, d, J=8.91 Hz), 6.85 (1H, d, J=8.58 Hz), 6.67 (1H, t, J=7.59 Hz), 4.06.~4.14 (2H, m), 4.02 (2H, q, J=7.59 Hz), 3.76~3.83 (1H, m), 3.54 (2H, t, J=5.28 Hz), 3.26~3.35 (2H, m), 3.09 (2H, brs), 2.72 (6H, d, J=9.24 Hz), 1.23 (3H, t, J=7.59 Hz).

Example 31
N-[2-(Dimethylamino)ethyl]-N-(1-butanesulfonyl)-N'-[2-(4-chlorophenoxy)ethyl]-o-phenylenediamine Hydrochloride $^1$H-NMR(270 MHz, DMSO-d$_6$) δ: 10.20 (1H, br), 7.32 (2H, d, J=8.58 Hz), 7.29~7.33 (1H, m), 7.22 (1H, t, J=8.24 Hz), 6.97 (2H, d, J=8.91 Hz), 6.84 (1H, d, J=8.25 Hz), 6.67 (1H, t, J=7.26 Hz), 4.11 (2H, t, J=5.61 Hz), 4.00~4.05 (1H, m), 3.70~3.75 (1H, m), 3.53 (2H, t, J=5.94 Hz), 3.24~3.55 (2H, m), 3.06 (2H, br), 2.73 (6H, d, J=13.20 Hz).

Example 32
N-[2-(Dimethylamino)ethyl]-N-(1-hexanesulfonyl)-N'-[2-(4-chlorophenoxy)ethyl]-o-phenylenediamine Hydrochloride $^1$H-NMR(270 MHz, DMSO-d$_6$) δ: 10.24 (1H, br), 7.32 (2H, d, J=8.58 Hz), 7.29~7.32 (1H, m), 7.22 (1H, t, J=8.24 Hz), 6.97 (2H, d, J=8.91 Hz), 6.84 (1H, d, J=8.24 Hz), 6.67 (1H, t, J=7.58 Hz), 4.10 (2H, t, J=5.61 Hz), 3.74~3.80 (1H, m), 3.51~3.55 (2H, m), 3.24~3.53 (2H, m), 3.06 (2H, brs), 2.73 (6H, d, J=12.21 Hz), 1.63~1.65 (2H, m), 0.84 (2H, t, J=6.27 Hz).

Example 33
N-[2-(2-Amino)ethoxyethyl-N-benzenesulfonyl-N'-(2-(4-chlorophenoxy)ethyl]-o-phenylenediamine $^1$H-NMR(270 MHz, CDCl$_3$) δ: 7.72 (2H, d, J=7.59 Hz), 7.58 (1H, t, J=7.26 Hz), 7.46 (2H, d, J=7.92 Hz), 7.23 (2H, d, J=8.57 Hz), 7.17 (1H, d, J=8.25 Hz), 6.87 (2H, d, J=8.91 Hz), 6.76 (1H, d, J=8.24 Hz), 6.49 (1H, t, J=7.59 Hz), 6.38 (1H, d, J=7.92 Hz), 5.19 (1H, t, J=5.94 Hz), 4.11 (2H, t, J=5.94 Hz), 4.02~4.11 (1H, m) 3.56 (2H, q, J=5.94 Hz), 3.24~3.50 (4H, m), 2.71 (2H, t, J=5.28 Hz).

Example 34
N-[2-(Dimethylamino)ethyl]-N-benzenesulfonyl-N'-[2-(4-chlorophenoxy)ethyl]-o-phenylenediamine Hydrochloride $^1$H-NMR(270 MHz, DMSO-d$_6$) δ: 10.69 (1H, brs), 7.74 (2H, d, J=7.92 Hz), 7.73~7.76 (1H, m), 7.34 (2H, d, J=8.91 Hz), 7.16 (1H, t, J=7.26 Hz), 7.00 (2H, d, J=8.91 Hz), 6.82 (1H, d, J=7.59 Hz), 6.43 (1H, t, J=7.26 Hz), 6.24 (1H, d, J=7.92 Hz), 4.30~4.35 (1H, m), 4.12 (2H, t, J=5.61 Hz), 3.44~3.55 (3H, m), 3.10 (2H, brs), 2.76 (6H, dd, J=12.21, 3.3 Hz).

Example 35
N-[2-(2-Amino)ethoxyethyl]-N-(p-toluenesulfonyl)-N'-[2-(4-chlorophenoxy)ethyl]-o-phenylenediamine $^1$H-NMR(270 MHz, CDCl$_3$) δ: 7.59 (2H, d, J=8.25 Hz), 7.24 (2H, d, J=8.9 Hz), 7.22 (2H, d, J=6.59 Hz), 6.87 (2H, d, J=8.91 Hz), 6.75 (1H, d, J=7.25 Hz), 6.50 (1H, t, J=7.92 Hz), 6.40 (1H, d, J=7.92 Hz), 5.19 (1H, brs), 4.11 (1H, t, J=5.28 Hz), 4.02~4.09 (1H, m), 3.56 (2H, q, J=5.28 Hz), 3.21~3.47 (3H, m), 2.74 (2H, t, J=4.95, 4.85 Hz), 2.41 (3H, s).

Example 36
N-[2-(Dimethylamino)ethyl]-N-(p-toluenesulfonyl)-N'-[2-(4-chlorophenoxy)ethyl]-o-phenylenediamine Hydrochloride $^1$H-NMR(270 MHz, DMSO-d$_6$) δ: 10.22 (1H, br), 7.61 (2H, d, J=8.25 Hz), 7.42 (1H, d, J=8.25 Hz), 7.34 (2H, d, J=9.24 Hz), 7.16 (1H, t, J=7.26 Hz), 6.99 (2H, d, J=8.91 Hz), 6.82 (1H, d, J=7.92 Hz), 6.44 (1H, t, J=7.25 Hz), 6.25 (1H, d, J=6.60 Hz), 4.23~4.30 (1H, m), 4.11 (2H, t, J=5.61 Hz), 3.41~3.53 (3H, m), 3.16 (3H, s), 3.06 (2H, brs), 2.63 (6H, d, J=17.16 Hz).

Example 37
N-[2-(2-Amino)ethoxyethyl]-N-(1-naphthalenesulfonyl)-N'-[2-(4-chlorophenoxy)ethyl]-o-phenylenediamine $^1$H-NMR (270 MHz, CDCl$_3$) δ: 8.64~8.69 (1H, m)H, 7.99~8.08 (2H, m), 7.88~7.91 (1H, m), 7.52~7.55 (2H, m), 7.52 (1H, t, J=4.29 Hz), 7.23 (2H, d, J=8.90 Hz), 7.11 (1H, t, J=6.93 Hz), 6.76 (2H, d, J=8.90 Hz), 6.69 (1H, d, J=7.59 Hz), 6.60 (1H, d, J=7.58 Hz), 6.44 (1H, t, J=7.59 Hz), 4.85 (1H, t, J=6.27 Hz), 4.10~4.19 (1H, m), 3.74~3.86 (1H, m), 3.66~3.72 (1H, m), 3.41~3.56 (3H, m), 3.29 (2H, t, J=4.95 Hz), 3.14~3.23 (1H, s), 2.66 (2H, t J=4.94 Hz).

Example 38
N-[2-(Dimethylamino)ethyl]-N-(1-naphthalenesulfonyl)-N'-[2-(4-chlorophenoxy)ethyl]-o-phenylenediamine Hydrochloride $^1$H-NMR(270 MHz, DMSO-d6) δ: 10.95 (1H, brs), 8.33 (2H, t, J=9.57 Hz), 8.12 (2H, t, J=7.58 Hz), 7.49~7.67 (4H, m), 7.35 (2H, d, J=8.91 Hz), 7.12 (1H, t, J=8.58 Hz), 6.95 (2H, d, J=8.91 Hz), 6.77 (1H, d, J=8.24 Hz), 6.29~6.79 (2H, m), 4.22~4.33 (1H, m), 3.88~3.96 (1H, m), 3.413.48 (1H, m), 3.31~3.39 (H, m), 3.14 (2H, brs), 2.74 (6H, dd, J=2.97, 10.23 Hz).

Example 39
N-[2-(2-Amino)ethoxyethyl]-N-(4-methoxybenzenesulfonyl)-N'-[2-(4-chlorophenoxy)ethyl]-o-phenylenediamine $^1$H-NMR(270 MHz, CDCl$_3$) δ: 7.64 (2H, d, J=8.91 Hz), 7.23 (2H, d, J=8.90 Hz), 7.17 (1H, t, J=6.93 Hz), 6.91 (2H, d, J=8.90 Hz), 6.87 (2H, d, J=8.91 Hz), 6.75 (1H, d, J=7.26 Hz), 6.51 (1H, t, J=7.26 Hz), 6.42 (1H, d, J=7.59 Hz), 5.21 (1H, brt, J=5.94 Hz), 4.11 (1H, t, J=5.94 Hz), 3.85 (3H, s), 3.56 (2H, q, J=5.61Hz), 3.22~3.46 (3H, m), 2.72 (2H, t, J=5.28 Hz).

Example 40

N-[2-(Dimethylamino)ethyl]-N-(4-methoxybenzenesulfonyl)-N'-[2-(4-chlorophenoxy)ethyl]-o-phenylenediamine Hydrochloride $^1$H-NMR(270 MHz DMSO-d$_6$) δ: 10.27 (1H, brs), 7.65 (2H, d, J=8.91 Hz), 7.55~7.61 (1H, m), 7.34 (2H, d, J=8.91 Hz), 7.16 (1H, t, J=7.26 Hz), 7.12 (2H, d, J=8.91 Hz), 7.00 (2H, d, J=8.91 Hz), 6.82 (2H, d, J=7.92 Hz), 6.46 (1H, t, J=7.25 Hz), 6.29 (1H, d, J=7.92 Hz), 4.24~4.29 (1H, m), 4.11 (2H, t, J=5.28 Hz), 3.86 (3H, s), 3.39~3.55 (3H, m), 3.06 (2H, brs), 2.77 (6H, d, J=15.84 Hz).

Example 41

N-[2-(2-Amino)ethoxyethyl]-N-(4-fluorobenzenesulfonyl)-N'-[2-(4-chlorophenoxy)ethyl]-o-phenylenediamine $^1$H-NMR(270 MHz, CDCl$_3$) δ: 7.73 (1H, d, J=4.95 Hz), 7.70 (1H, d, J=4.95 Hz), 7.10~7.26 (6H, m), 6.87 (2H, d, J=9.24 Hz), 6.78 (1H, d, J=8.24 Hz), 6.52 (1H, t, J=7.92 Hz), 6.39 (1H, d, J=7.59 Hz), 5.18 (1H, brs), 4.12 (2H, t, J=5.28 Hz), 4.04 (1H, t, J=6.6 Hz), 3.56 (2H, br), 3.27~3.48 (6H, m), 2.77 (2H, t, J=4.95 Hz).

Example 42

N-[2-(Dimethylamino)ethyl]-N-(4-fluorobenzenesulfonyl)-N'-[2-(4-chlorophenoxy)ethyl]-o-phenylenediamine Hydrochloride $^1$H-NMR(270 MHz, DMSO-d$_6$) δ: 10.10 (1H, br), 7.63 (2H, d, J=7.53 Hz), 7,57 (2H, d, J=7.59 Hz), 7.48 (H, t, J=8.91 Hz), 7.35 (2H, d, J=8.91 Hz), 7.17 (1H, t, J=7.26 Hz), 6.98 (2H, d, J=8.91 Hz), 6.83 (H, d, J=8.25 Hz), 6.46 (1H, t, J=7.25 Hz), 6.27 (1H, d, J=7.94 Hz), 4.26~4.32 (1H, m), 4.12 (2H, t, J=5.61 Hz), 3.48~3.53 (1H, m), 3.07 (2H, brs), 2.79 (6H, dd, J=21.77, 2.97 Hz).

Example 43

N-[2-(2-Amino)ethoxyethyl]-N-(4-bromobenzenesulfonyl)-N'-[2-(4-chlorophenoxy)ethyl]-o-phenylenediamine $^1$H-NMR (270 MHz, CDCl$_3$) δ: 7.61 (2H, d, J=9.24 Hz), 7.56 (2H, d, J=9.24 Hz), 7.22 (2H, d, J=9.23 Hz), 7.19 (1H, t, J=7.26 Hz), 6.87 (2H, d, J=9.24 Hz), 6.76 (1H, d, J=3.24 Hz), 6.53 (1H, t, J=7.92 Hz), 6.42 (1H, d, J=7.92 Hz), 4.97 (1H, brt, J=6.27 Hz), 4.00~4.13 (3H, m), 3.26~3.57 (11H, m), 2.74~2.78 (2H, m), 2.08 (2H, br).

Example 44

N-[2-(Dimethylamino)ethyl]-N-(4-bromobenzenesulfonyl)-N'-[2-(4-chlorophenoxy)ethyl]-o-phenylenediamine.HCl $^1$H-NMR(270 MHz, DMSO-d$_6$) δ: 10.08 (1H, br), 7.85 (2H, d, J=8.58 Hz), 7.64 (2H, d, J=8.58 Hz), 7.58 (1H, t, J=6.93 Hz), 7.34 (2H, d, J=8.91 Hz), 7.17 (H, t, J=7.26 Hz), 6.98 (2H, d, J=8.58 Hz), 6.83 (1H, d, J=7.92 Hz), 6.47 (H, t, J=7.25 Hz), 6.32 (1H, d, J=6.92 Hz), 4.26~4.32 (1H, m), 4.11 (20H, t, J=5.94 Hz), 3.45~3.60 (3H, m), 3.07 (2H, brs), 2.79 (6H, dd, J=22.10, 2.97 Hz).

Example 45

N-[2-(2-Amino)ethoxyethyl]-N-(4-iodobenzenesulfonyl)-N'-[2-(4-chlorophenoxy)ethyl]-o-phenylenediamine $^1$H-NMR(270 MHz, CDCl$_3$) δ: 7.79 (2H, d, J=8.58 Hz), 7.39 (2H, d, J=8.57 Hz), 7.22 (2H, d, J=8.9 Hz), 6.88 (2H, d, J=8.91 Hz), 6.85 (1H, t, J=7.36 Hz), 6.58 (1H, t, J=7.59 Hz), 6.40 (1H, d, J=6.27 Hz), 5.11 (1H, br), 4.04~4.18 (3H, m), 3.43 3.64 (6H, m), 3.27~3.39 (1H, m), 2.99~3.05 (2H, m).

Example 46

N-[2-(Dimethylamino)ethyl]-N-(4-iodobenzenesulfonyl)-N'-[2-(4-chlorophenoxy)ethyl]-o-phenylenediamine Hydrochloride $^1$H-NMR(270 MHz, DMSO-d$_6$) δ: 10.24 (1H, brs), 7.83 (2H, d, J=8.54 Hz), 7.62 (2H, d, J=8.58 Hz), 7.58 (1H, t, J=7.24 Hz), 7.22 (2H, d, J=8.91 Hz), 7.16 (1H, t, J=7.26 Hz), 6.88 (2H, d, J=8.91 Hz), 6.82 (1H, d, J=7.92 Hz), 6.46 (1H, t, J=7.24 Hz), 6.32 (1H, d, J=6.92 Hz), 4.24~4.32 (1H, m), 4.10 (2H, t, J=5.94 Hz), 3.43~3.58 (3H, m), 3.04 (2H, brs), 2.78 (6H, dd, J=20.18, 2.94 Hz).

Example 47

N-[2-(2-Amino)ethoxyethyl]-N-(4-chlorobenzenesulfonyl)-N'-[2-(4-fluorophenoxy)ethyl]-o-phenylenediamine $^1$H-NMR(270 MHz, CDCl$_3$) δ: 7.41 (4H, s), 7.22 (2H, d, J=8.91 Hz), 7.16~7.19 (1H, m), 6.86 (2H, d, J=8.90 Hz), 6.74 (1H, d, J=8.22 Hz), 6.52 (1H, t, J=7.26 Hz), 6.40 (1H, d, J=7.90 Hz), 5.14 (1H, brt, J=5.92 Hz), 4.00~4.12 (2H, m), 3.56 (2H, q, J=5.60 Hz), 3.22~3.45 (5H, m), 2.74 (2H, t, J=5.28 Hz).

Example 48

N-[2-(Dimethylamino)ethyl]-N-(4-chlorobenzenesulfonyl)-N'-[2-(4-fluorophenoxy)ethyl]-o-phenylenediamine Hydrochloride $^1$H-NMR(270 MHz, DMSO-d$_6$) δ: 10.32 (1H, brs), 7.62 (2H, d, J=8.58 Hz), 7.48 (1H, t, J=7.98 Hz), 7.42 (2H, d, J=8.52 Hz), 7.38 (2H, d, J=8.54 Hz), 7.16 (H, t, J=7.24 Hz), 6.84 (2H, d, J=7.94 Hz), 6.76 (1H, d, J=7.42 Hz), 6.43 (1H, t, J=7.24 Hz), 6.32 (1H, d, J=6.91 Hz), 4.22~4.34 (1H, m), 4.10 (2H, t, J=5.92 Hz), 3.42~3.56 (3H, m), 3.06 (2H, brs), 2.76 (6H, dd, J=14.4, 2.68 Hz).

Example 49

N-[2-(2-Amino)ethoxyethyl]-N-(4-chlorobenzenesulfonyl)-N'-(2-phenoxyethyl)-o-phenylenediamine $^1$H-NMR(270 MHz, CDCl$_3$) δ: 7.2 (2H, d, J=7.58 Hz), 7.56 (1H, t, J=7.25 Hz), 7.43 (2H, t J=7.92 Hz), 7.23 (2H, d, J=8.57 Hz), 7.16 (1H, t, J=7.26 Hz), 6.87 (2H, d, J=8.91 Hz), 6.76 (1H, d, J=8.23 Hz), 6.49 (1H, t, J=7.59 Hz), 6.38 (1H, brt, J=7.92 Hz), 5.16 (1H, t,J=5.94 Hz), 4.11 (2H, t, J=5.94 Hz), 4.06~4.11 (H, m), 3.56 (2H q, J=5.94 Hz), 3.22~3.58 (4H, m), 2.71 (2H, t, J=5.28 Hz).

Example 50

N-[2-(Dimethylamino)ethyl]-N-(4-chlorobenzenesulfonyl)-N'-(2-phenoxyethyl)-o-phenylenediamine Hydrochloride $^1$H-NMR(270 MHz, DMSO-d$_6$) δ: 10.54 (1H, br), 7.76 (2H, d, J=7.92 Hz), 7.72~7.74 (1H, m), 7.42 (2H, d, J=8.90 Hz), 7.16 (1H, t J=7.26 Hz), 7.02 (2H, d, J=8.91 Hz), 6.82 (1H, d, J=7.54 Hz), 6.42 (1H, t, J=7.43 Hz), 6.24 (1H, d, J=7.92 Hz), 4.32~4.36 (1H, m), 4.10 (2H, t, J=5.62 Hz), 3.43~3.54 (3H, m), 3.12 (2H, brs), 2.78 (6H, dd, J=13.4, 2.7 Hz).

Example 51

N-[2-(Dimethylamino)ethyl]-N-(2-chlorobenzenesulfonyl)-N'-[2-(4-chlorophenoxy)ethyl]-o-phenylenediamine Hydrochloride $^1$H-NMR(270 MHz, DMS-d$_6$) δ: 10.77 (1H, brs), 7.52~7.74 (4H, m), 7.44 (1H, t, J=7.26 Hz), 7.36 (2H, d, J=8.91 Hz), 7.16 (1H, t, J=7.26 Hz), 7.01 (2H, d, J=9.24 Hz), 6.82 (1H, d, J=8.25 Hz), 6.57 (1H, dd J=7.92 Hz), 6.46 (1H, t, J=7.26 Hz), 4.41 −4.46 (1H, m), 4.11 (2H, t, J=5.61 Hz), 3.81~3.36 (1H, m), 3.42~3.55 (2H, m), 3.15 (2H, brs), 2.74 (6H, d, J=6.93 Hz).

Example 52

N-[2-(Dimethylamino)ethyl]-N-(3-chlorobenzenesulfonyl)-N'-[2-(4-chlorophenoxy)ethyl]-o-phenylenediamine Hydrochloride $^1$H-NMR(270 MHz, DMSO-d$_6$) δ: 10.55 (1H, brs), 7.79~7.85 (2H, m), 7.64 (2H, d, J=4.62 Hz), 7.55~7.61 (1H, m), 7.34 (2H, d, J=8.91 Hz), 7.18 (1H, t, J=8.58 Hz), 6.98 (2H, d, J=8.91 Hz), 6.83 (1H, d, J=7.59 Hz), 6.46 (1H, t, J=6.93 Hz), 6.33 (1H, d, J=7.92 Hz), 4.33~4.38 (1H, m), 4.11 (2H, t, J=5.94 Hz), 3.49~3.55 (2H, m), 3.10 (2H, br), 2.78 (6H, dd, J=18.14, 3.95 Hz).

Example 53

N-[2-(Dimethylamino)ethyl]-N-(4-chlorobenzenesulfonyl)-N'-[2-(4-methylphenoxy)ethyl]-o-phenylenediamine Hydrochloride $^1$H-NMR(270 MHz, DMSO-d$_6$) δ: 10.13 (1H, br), 7.73 (2H, d, J=8.91 Hz), 7.70 (2H, d, J=9.24 Hz), 7.54~7.68 (2H, m), 7.17 (1H, t, J=7.59 Hz), 7.09 (2H, d, J=8.58 Hz), 6.85 (2H, d, J=8.58 Hz), 6.81~6.84 (1H, m), 6.47 (1H, t, J=7.92 Hz), 6.32 (1H, d, J=7.25 Hz), 4.06 (2H, t, J=5.94 Hz), 3.45~3.56 (3H, m), 3.07 (2H, brs), 2.78 (6H, d, J=19.46 Hz).

Example 54

N-[2-(Dimethylamino)ethyl]-N-(4-chlorobenzenesulfonyl)-N'-[2-(4-bromophenoxy)ethyl]-o-phenylenediamine Hydrochloride $^1$H-NMR(270 MHz, DMSO-d$_6$) δ: 10.24 (1H, brs), 7.84 (2H, d, J=8.42 Hz), 7.62 (2H, d, J=8.54 Hz), 7.56 (1H, t, J=8.92 Hz), 7.23 (2H, d, J=8.54 Hz), 7.16 (1H, t, J=7.26 Hz), 6.84 (2H, d, J=7.94 Hz), 6.76 (1H, d, J=7.92 Hz), 6.42 (1H, t, J=7.24 Hz), 6.32 (1H, d, J=6.92 Hz), 4.23~4.33 (1H, m), 4.12 (2H, t, J=5.92 Hz), 3.42~3.58 (3H, m), 3.04 (2H, brs), 2.77 (6H, dd, J=21.21, 2.95 Hz).

Example 55

N-[2-(Dimethylamino)ethyl]-N-(4-chlorobenzenesulfonyl)-N'-[2-(4-chlorophenoxy)ethyl]-m-phenylenediamine Hydrochloride $^1$H-NMR(270 MHz, DMSO-d$_6$) δ: 10.53 (1H, br), 7.68 (2H, d, J=8.58 Hz), 7.63 (2H, d, J=8.58 Hz), 7.34 (2H, d, J=8.91 Hz), 7.08 (1H, t, J=7.92 Hz), 6.97 (2H, d, J=8.91 Hz), 6.66 (1H, d, J=8.25 Hz), 6.44 (1H, s), 6.26 (1H, d, J=7.92 Hz), 3.91~4.08 (4H, m), 3.34 (2H, t, J=5.61 Hz), 3.10~3.18 (2H, m), 2.80 (6H, d, J=4.62 Hz).

Example 56

N-[2-(Dimethylamino)ethyl]-N-(2-chlorobenzenesulfonyl)-N'-[2-(4-chlorophenoxy)ethyl]-p-phenylenediamine Hydrochloride $^1$H-NMR(270 MHz, DMSO-d$_6$) δ: 10.47 (1H, brs), 7.69 (2H, d, J=8.57 Hz), 7.59 (2H, d, J=8.58 Hz), 7.32 (2H, d, J=8.58 Hz), 6.97 (2H, d, J=8.91 Hz), 6.82 (2H, d, J=8.91 Hz), 6.62 (2H, d, J=8.57 Hz), 4.10 (2H, t, J=5.28 Hz), 3.88 (2H, t, J=6.27 Hz), 3.41 (2H, t, J=5.27 Hz), 3.08 (2H, q, J=6.27 Hz), 2.77 (6H, d, J=4.62 Hz).

Example 57

N-[2-(Dimethylamino)ethyl]-N-(5-isoquinolinesulfonyl)-N'-[2-(4-chlorophenoxy)ethyl]-o-phenylenediamine Hydrochloride $^1$H-NMR(270 MHz, DMSO-d$_6$) δ: 10.42 (1H, br), 9.65 (1H, s), 8.64 (1H, d, J=8.25 Hz), 8.53 (1H, d, J=7.26 Hz), 8.46 (1H, d, J=6.60 Hz), 8.10 (1H, d, J=6.60 Hz), 7.96 (1H, t, J=7.91 Hz), 7.35 (2H, d, J=8.91 Hz), 7.11~7.16 (1H, m), 6.97 (2H, d, J=8.91 Hz), 6.84 (1H, d, J=8.58 Hz), 6.23~6.25 (2H, m), 4.27~4.32 (1H, m), 4.01 (2H, t, J=7.25 Hz), 3.36~3.25 (2H, m), 3.13 (2H, brs), 2.77 (6H, dd, J=19.13, 2.63 Hz).

Example 58

N-[2-(Dimethylamino)ethyl]-N-(4-chlorobenzenesulfonyl)-N'-[2-(3-chlorophenoxy)ethyl]-o-phenylenediamine Hydrochloride $^1$H-NMR(270 MHz, DMSO-d$_6$) δ: 10.49 (1H, br), 8.93~8.95 (1H, m), 8.61 (1H, t, J=6.26 Hz), 8.08 (1H, t, J=6.60 Hz), 7.74 (2H, d, J=9.24 Hz), 7.68 (2H, d, J=8.90 Hz), 7.43 (1H, d, J=6.27 Hz), 7.31 (2H, t, J=8.25 Hz), 7.14~7.29 (2H, m), 6.98 (1H, t, J=7.59 Hz), 6.89 (1H, d, J=8.25 Hz), 6.48 (1H, t, J=7.92 Hz), 6.35 (1H, d, J=7.92 Hz), 4.18 (2H, t, J=5.97 Hz), 3.70~3.74 (2H, m), 3.10~3.18 (2H, m), 2.71~2.77 (6H, m).

Example 59

N-[2-(Dimethylamino)ethyl]-N-(4-chlorobenzenesulfonyl)-N'-[2-(2-chlorophenoxy)ethyl]-o-phenylenediamine Hydrochloride $^1$H-NMR(270 MHz, DMSO-d$_6$) δ: 10.24 (1H, br), 7.48~7.72 (4H, m), 7.46 (1H, t, J=7.24 Hz), 7.36 (2H, d, J=8.92 Hz), 7.14 (1H, t, J=7.24 Hz), 7.04 (2H, d, J=8.92 Hz), 6.82 (1H, d, J=8.24 Hz), 6.56 (1H, d, J=7.92 Hz), 6.46 (1H, t, J=7.24 Hz), 4.43~4.46 (1H, m), 4.10 (2H, t, J=5.60 Hz), 3.78~3.86 (1H, m), 3.42~3.54 (2H, m), 3.14 (2H, brs), 2.76 (6H, d, J=10.24 Hz).

Example 60

N-(2-Aminoethyl)-N-(4-chlorobenzenesulfonyl)-N'-[2-(4-chlorophenylamino)ethyl]-o-phenylenediamine $^1$H-NMR (270 MHz, CDCl$_3$) δ: 7.63 (2H, d, J=8.58 Hz), 7.41 (2H, d, J=8.58 Hz), 7.13~7.16 (1H, m), 7.11 (2H, d, J=8.58 Hz), 6.68~6.71 (1H, m), 6.58 (2H, d, J=8.58 Hz), 6.30~6.47 (3H, m), 5.02 (1H, t, J=5.88 Hz), 4.20 (2H, t, J=5.64 Hz), 3.86~3.96 (1H, m), 3.55 (2H, t, J=5.28 Hz), 3.04~3.11 (1H, m), 2.65~2.73 (1H, m), 2.58~2.68 (1H, m).

Example 61

N-[2-(2-Amino)ethoxyethyl]-N-(4-chlorobenzenesulfonyl)-N'-[3-(4-chlorophenoxy)propyl]-o-phenylenediamine $^1$H-NMR(270 MHz, CDCl$_3$) δ: 7.64 (2H, d, J=8.58 Hz), 7.44 (2H, d, J=8.91 Hz), 7.22 (2H, d, J=8.9 Hz), 7.15 (1H, t, J=6.93 Hz), 6.87 (2H, d, J=8.91 Hz), 6.70 (1H, d, J=8.25 Hz), 6.45 (1H, t, J=7.91 Hz), 6.34 (1H, d, J=7.59 Hz), 4.98 (1H, t, J=5.94 Hz), 4.01~4.14 (3H, m), 3.23~3.48 (6H, m), 2.75 (2H, t, J=5.20 Hz), 2.04~2.14 (2H, m).

Example 62

N-(2-Aminoethyl)-N-(4-chlorobenzenesulfonyl)-N'-(4-chlorocinnamyl)-o-phenylenediamine $^1$H-NMR(270 MHz, CDCl$_3$) δ: 7.64 (2H, d, J=8.58 Hz), 7.46 (2H, d, J=8.58 Hz), 7.28 (4H, m), 7.15 (1H, t, J=7.26 Hz), 6.71 (1H, t, J=8.25 Hz), 6.58 (1H, d, J=16.16 Hz), 6.51 (1H, t, J=7.59 Hz), 6.19~6.33 (2H, m), 3.96 (2H, d, J=5.63 Hz), 3.11~3.19 (H, m), 3.28~3.87 (1H, m), 2.632.78 (1H, m).

Example 63

N-[2-(2-Amino)ethoxyethyl]-N-(4-chlorobenzenesulfonyl)-N'-[2-(4-chlorophenyl)ethyl]-o-phenylenediamine $^1$H-NMR(270 MHz, CDCl$_3$) δ: 7.65 (2H, d, J=8.58 Hz), 7.42~7.49 (1H, m), 7.40 (LH, d, J=8.58 Hz), 7.24 (2H, d, J=9.24 Hz), 7.11~7.18 (1H, m), 6.87 (2H, d, J=8.91 Hz), 6.71 (1H, d, J=8.25 Hz), 6.44~6.51 (2H, m), 5.80 (1H, t, J=5.94 Hz), 4.05~4.12 (3H, m), 3.49~3.52 (2H, m), 2.33~2.44 (2H, m).

Example 64
N-[2-(2-Amino)ethoxyethyl]-N-(4-chlorobenzenesulfonyl)-N'-[2-(4-chlorophenylthio)ethyl]-o-phenylenediamine $^1$H-NMR(270 MHz, CDCl$_3$) δ: 7.65 (2H, d, J=8.58 Hz), 7.45 (2H, d, J=8.58 Hz), 7.35 (2H, d, J=8.91 Hz), 7.27 (2H, d, J=8.91 Hz), 7.15 (1H, t, J=6.93 Hz), 6.58 (1H, d, J=6.27 Hz), 6.49 (1H, t, J=7.59 Hz), 6.36 (1H, d, J=7.92 Hz), 5.12 (1H, brt, J=6.46 Hz), 4.01~4.10 (1H, m), 3.26~3.59 (8H, m), 3.10 (2H, t, J=7.26 Hz), 2.76 (2H, t, J=4.95 Hz).

Example 65
N-(2-Aminoethyl)-N-(4-chlorobenzenesulfonyl)-N'-[2-(4-Chlorophenylthio)ethyl]-o-phenylenediamine $^1$H-NMR(270 MHz, CDCl$_3$) δ: 7.29 (2H, d, J=8.91 Hz), 7.23 (2H, d, J=8.91 Hz), 7.11 (2H, d, J=8.58 Hz), 6.67~6.82 (1H, m), 6.58 (2H, d, J=8.58 Hz), 6.24~6.45 (3H, m), 5.04 (1H, t, J=5.92 Hz), 4.08 (2H, t, J=5.62 Hz), 3.88~3.97 (1H, m), 3.78~3.86 (2H, m), 3.05~3.12 (1H, m), 2.72~2.76 (1H, m), 2.58~2.68 (1H, m).

Example 66
3-(4-chlorobenzenesulfonylamino)-4-[2-(4-chlorophenoxy)ethyl)amino-1-(4-morpholinocarbonyl)benzene $^1$H-NMR(270 MHz, CDCl$_3$) δ: 7.70 (1H, brs), 7.61 (2H, d, J=8.57 Hz), 7.39~7.12 (5H, m), 6.86 (2H, d, J=8.91 Hz), 6.59 (1H, d, J=8.58 Hz), 6.34 (1H, d, J=1.98 Hz), 5.35 (1H, m), 4.08 (2H, m), 3.76~3.25 (10H, m).

Example 67
3-[N-[2-(2-Amino)ethoxyethyl]-N-(4-chlorobenzenesulfonyl)]amino-4-[2-(4-chlorophenoxy)ethyl]amino-1-(4-morpholinocarbonyl)benzene $^1$H-NMR(270 MHz, CDCl$_3$) δ: 7.67 (2H, d, J=8.57 Hz), 7.44 (2H, d, J=8.57 Hz), 7.31 (1H, dd, J=8.58, 1.98 Hz), 7.25 (2H, d, J=8.90 Hz), 6.86 (2H, d, J=8.90 Hz), 6.73 (1H, d, J=8.58 Hz), 6.69 (1H, d, J=1.98 Hz), 5.53 (1H, m), 4.16~4.03 (3H, m), 3.70~3.27 (15H, m), 2.73 (2H, m).

Example 68
N-[2-(2-Amino)ethoxyethyl]-N-(4-chlorobenzenesulfonyl)-N'-[2-(4-chlorophenoxy)ethyl]-N'-methy]-o-phenylenediamine $^1$H-NMR(270 MHz, CDCl$_3$) δ: 7.84 (2H, d, J=8.57 Hz), 7.46 (2H, d, J=8.57 Hz), 7.20~7.25 (1H, m), 7.21 (2H, d, J=8.91 Hz), 7.09 (1H, d, J=7.92 Hz), 6.91~6.93 (2H, m), 6.78 (2H, d, J=8.9 Hz), 4.00 (4H, br), 3.50~3.74 (4H, m), 3.50~3.57 (4H, m), 3.12~3.19 (4H, m), 2.87 (3H, s), 2.76 (2H, br).

Example 69
N-[2-(Dimethylamino)ethyl]-N-(4-chlorobenzenesulfonyl)-N'-[2-(4-chlorophenoxy)ethyl]-N'-methy]-o-phenylenediamine Hydrochloride $^1$H-NMR(270 MHz, DMSO-d$_6$) δ: 10.24 (1H, brs), 7.76 (2H, d, J=8.92 Hz), 7.72 (2H, d, J=8.92 Hz), 7.42 (2H, d, J=9.24 Hz), 7.16 (1H, t, J=7.26 Hz), 6.98 (2H, d, J=8.92 Hz), 6.84 (1H, d, J=7.92 Hz), 6.47 (1H, d, J=7.24 Hz), 6.32 (1H, d, J=6.90 Hz), 4.28~4.32 (1H, m), 4.10 (2H, t, J=5.94 Hz), 3.46 (2H, t, J=5.46 Hz), 3.06 (2H, brs), 2.89 (3H, s), 2.78 (6H, dd, J=21.89, 2.98 Hz).

Example 70
N-[2-(2-Amino)ethoxyethyl]-N-(4-chlorobenzenesulfonyl)-N'-benzyl-N'-[2-(4-chlorophenoxy)ethyl]-o-phenylenediamine $^1$H-NMR(270 MHz, CDCl$_3$) δ: 7.84 (2H, d, J=8.9 Hz), 7.45 (2H, d, J=8.58 Hz), 7.28 (4H, d, J=3.63 Hz), 7.20~7.24 (1H, m), 7.17 (2H, d, J=8.91 Hz), 6.91~6.95 (2H, m), 6.71 (2H, d, J=8.91 Hz), 4.41 (2H, d, J=2.97 Hz), 4.03~4.16 (1H, m), 3.91~3.96 (2H, m), 3.48~3.58 (2H, m), 3.00~3.20 (4H, m), 2.53 (2H, q, J=4.95 Hz).

Example 71
N-[2-(Dimethylamino)ethyl]-N-(4-chlorobenzenesulfonyl)-N'-benzyl-N'-[2-(4-chlorophenoxy)ethyl]-o-phenylenediamine Hydrochloride $^1$H-NMR(270 MHz, DMSO-d$_6$) δ: 10.26 (1H, brs), 7.78 (2H, d, J=8.56 Hz), 7.68 (2H, d, J=8.58 Hz), 7.24~7.48 (6H, m), 7.18 (1H, t, J=7.26 Hz), 6.98 (2H, d, J=8.59 Hz), 6.84 (1H, d, J=7.42 Hz), 6.47 (1H, d, J=7.34 Hz), 6.34 (1H, d, J=6.98 Hz), 4.42 (2H, d, J=2.96 Hz), 4.28~4.32 (1H, m), 4.12 (2H, t, J=5.92 Hz), 3.44 (2H, t, J=5.46 Hz), 3.06 (2H, brs), 2.78 (6H, dd, J=22.20, 2.94 Hz).

Example 72
N-[2-(4-chlorophenoxy)ethyl]-N-[2-(dimethylamino)ethyl]-N'-(4-chlorobenzenesulfonyl)-o-phenylenediamine $^1$H-NMR(270 MHz, CDCl$_3$) δ: 7.69 (2H, d, J=8.6 Hz), 7.63 (2H, dd, J=7.6, 2 Hz), 7.23 (2H, d, J=8.9 Hz), 7.17 (1H, dd, J=7.6, 2 Hz), 7.18 (1H, br), 7.16 (2H, d, J=8.61 Hz), 7.09 (1H, td, J=7.6, 2 Hz), 7.02 (1H, td, J=7.6, 2 Hz), 6.70 (2H, d, J=8.9 Hz), 3.55 (2H, brt, J=5.6 Hz), 3.23 (2H, t, J=5.6 Hz), 2.94 (2H, br), 2.43 (6H, s), 2.37 (2H, brt, J=6 Hz).

Example 73
N-[2-(4-Chlorophenoxy)ethyl]-N-(4-chlorobenzenesulfonyl)-N'-(4-chlorobenzenesulfonyl)-o-phenylenediamine $^1$H-NMR(270 MHz, CDCl$_3$) δ: 7.94 (1H, s), 7.86 (2H, dm, J=8.6 Hz), 7.54 (2H, dm, J=8.9 Hz), 7.50 (1H, dd, J=8.5, 1.3 Hz), 7.45 (2H, dm, J=8.9 Hz), 7.42 (2H, dm, J=8.6 Hz), 7.24 (1H, td, J=8.5.1.3 Hz), 7.23 (2H, dm, J=8.9 Hz), 6.89 (1H, td, J=7.9, 1.3 Hz), 6.77 (2H, dm, J=8.9 Hz), 6.46 (1H, dd, J=7.9, 1.3 Hz), 4.19 (1H, dq, J=7.3, 5.0 Hz), 3.92~3.98 (1H, m), 3.79~3.87 (1H, m), 3.44 (1H, dt, J=13.9, 4.9 Hz).

Referential Example 2
N-(2-Aminoethyl)-p-chloroaniline

4-Chlorofluorobenzene (92.00 g) and ethylenediamine (290.0 g) were placed in a pressure-resistant stainless-steel reactor. A stirrer was placed in the reactor and the reactor was sealed. Subsequently, the reaction mixture was stirred for 2 days at an external temperature of 200° C. The reaction mixture was allowed to cool, and chloroform (800 ml) was added to the mixture. The mixture was transferred to a separating funnel, washed sequentially with water (200 ml), saturated brine (200 ml), and a saturated sodium hydrogencarbonate solution (100 ml) in this order. The aqueous layer was extracted with chloroform (200 ml×3), washed with saturated brine, combined with the chloroform layer again, and dehydrated over anhydrous magnesium sulfate. The solvent was removed under reduced pressure, to thereby yield the target compound (116.69 g) as a pale-yellow oily product, Since this product contained almost no impurities and was considered to be almost pure by NMR, the product was submitted to the next reaction step without further purification.

$^1$H-NMR(270 MHz, CDCl$_3$) δ: 7.11 (2H, dm, J=8.9 Hz), 6.54 (2H, dm, J=8.9 Hz), 4.08 (1H, br), 3.14 (2H, t, J=6 Hz), 2.95 (2H, t, J=6 Hz).

Referential Example 3
2-[2-(4-Chlorophenyamino)ethylamino]-3-nitropyridine

Chloroform (1000 ml) was added to N-(2-aminoethyl)-p-chloroaniline (116.67 g) and the mixture was dissolved. Triethylamine (83.02 g) and 2-chloro-3-nitropyridine (108.40 g) were added to the resultant solution on ice in this order and stirred for 2 hours at room temperature. Subsequently, the resultant mixture was refluxed for one hour, cooled, washed with water (500 ml×2), and the aqueous layer was extracted with chloroform (500 ml). The aqueous layer was combined with the chloroform layer, washed with saturated brine, and dehydrated over anhydrous magnesium sulfate. After filtration, the solvent was removed under reduced pressure. The thus-obtained crystalline residue was purified by silica gel chromatography (elution solvent=chloroform:methanol=100:5), to thereby obtain the target compound in the form of colorless crystals (195.97 g).

$^1$H-NMR(270 MHz, CDCl$_3$) δ: 8.43 (1H, dd, J=7.5, 1.6 Hz), 8.42 (1H, dd, J=4.6, 1.6 Hz), 7.12 (2H, dm, J=8.9 Hz), 6.70 (1H, dd, J=7.5, 4.6 Hz), 6.57 (2H, dm, J=8.9 Hz), 4.17 (1H, br), 3.90 (2H, dt, J=6.3, 5.9 Hz), 3.43 (2H, t, J=5.9 Hz).

Referential Example 4

2-[2-(4-Chlorophenyamino)ethylamino]-3-aminopyridine

Ethanol (300 ml) and ethyl acetate (300 ml) were added to the product obtained from Referential Example 3 (97.11 g) and the mixture was dissolved. 20% Palladium hydroxide-carbon (7.50 g) was added to the resultant solution and the mixture was stirred for 6 hours at room temperature under hydrogen gas (1 atm). After completion of the reaction, the catalyst was removed by filtration, and the solvent was removed under reduced pressure, to thereby yield the target compound (87.16 g) as an amorphous product, This product was submitted to the next reaction step without further purification.

$^1$H-NMR(270 MHz, CDCl$_3$) δ: 7.89 (1H, dd, J=4.6, 1.6 Hz), 7.52 (2H, dm, J=8.9 Hz), 7.32 (2H, dm, J=8.9 Hz), 7.09 (1H, dd, J=7.9, 1.6 Hz), 7.00 (1H, dd, J=7.9, 4.6 Hz), 4.48 (2H brs), 4.20 (2H, m), 3.98 (2H, m).

Example 74

3-(4-Chlorobenzenesulfonylamino)-2-[2-(4-chlorophenylamino)ethylamino]pyridine

Chloroform (20 ml) was added to the product of Referential Example 4 (0.45 g) to dissolve the compound. To the resultant solution were added pyridine (0.16 g) and p-chlorobenzenesulfonyl chloride (0.40 g) in this order and the mixture was stirred for 2 days at room temperature. The solvent was removed under reduced pressure and the thus-produced residue was purified by silica gel chromatography (elution solvent=n-hexane:ethyl acetate=2:1), to thereby obtain the target compound as colorless crystals (0.64 g).

$^1$H-NMR(270 MHz, CDCl$_3$), δ: 8.02 (1H, dd, J=5.3, 1.6 Hz), 7.65 (2H, dm, J=8.6 Hz), 7.43 (2H, dm, J=8.6 Hz), 7.10 (2H, dm, J=8.9 Hz), 6.64 (1H, dd, J=7.6, 1.6 Hz), 6.57 (2H, dm, J=8.9 Hz), 6.39 (H, dd, J=7.6, 5.3 Hz), 5.73 (1H, br), 3.65~3.75 (2H, br), 3.31 (2H, brt, J=6 Hz).

Example 75

3-[N-(4-Chlorobenzenesulfonyl)-N-(2-t-butoxycarbonylaminoethyl)]amino- 2-[2-(4-chlorophenyl)aminoethyl]aminopyridine Tetrahydrofuran (800 ml) was added to the product of Example 74 (80.87 g) to dissolve the compound. Triphenylphosphine (58.20 g) and N-t-butoxycarbonyl-aminoethanol (35.77 g) were added to the resultant solution while cooling on ice. Subsequently, diisopropylazocarboxylate (44.87 g) was added dropwise to the resultant mixture over 30 min on ice, and, after completion of the dropwise addition, the mixture was stirred for one hour at room temperature. The solvent was removed under reduced pressure and the residue was purified by silica gel chromatography (elution solvent=n-hexane:ethyl acetate=2:1). The thus-eluted fraction was further purified by silica gel chromatography (elution solvent=n-hexane:ethyl acetate=1:1), to thereby yield the target compound (100.1 g) as an amorphous product, $^1$H-NMR(270 MHz, CDCl$_3$) δ: 8.09 (1H, dd, J=4.6, 1.6 Hz), 7.60 (2H, dm, J=8.6 Hz), 7.48 (2H, dm,J=8.6 Hz), 7.10 (2H, dm, J=8.9 Hz), 6.60 (2H, dm, J=8.9 Hz), 6.50 (1H, dd, J=7.7, 1.6 Hz), 6.43 (1H, dd, J=7.7, 4.6 Hz), 5.87 (1H, brt), 5.13 (1H, brt), 3,94~4.02 (1H, m), 3.68~3.76 (2H, m), 3.39 (2H, t, J=5.6 Hz), 3.10~3.,13 (3H, m), 1.39 (9H, s).

Referential Example 5

2-[2-[N-(4-Chlorophenyl)-N-t-butoxycarbonyl]aminoethyl] amino-3-nitropyridin

The product of Referential Example 3 (195.97 g) was dissolved in chlorofolm (1.2 l), and then di-t-butyldicarbonate (BoC$_2$O, 160.72 g) and N,N-dimethylaminopyridine (DMAP, 2.44 g) were added thereto, followed by stirring at room temperature for two days. In order not to consume all the starting compounds, BoC$_2$O (about 40 g) and DAMP (1.22 g) were added thereto every two days and the thus-obtained mixture was allowed to react for ten days in total. Subsequently, the solvent was removed by evaporation. The thus-obtained yellow residue was purified by means of silica gel column chromatography (solvent:n-hexane/acetic acid=9/1) to yield the target product (58.78 g) as colorless amorphous.

$^1$H-NMR(270 MHz, CDCl3) δ: 8.39 (1H, dd, J=7.5, 1.6 Hz), 8.36 (1H, dd, J=4.6, 1.6 Hz), 8.35 (1H, br), 7.27 (2H, dm, J=8.9 Hz), 7.15 (2H, dm, J=8.9 Hz), 6.66 (1H, dd, J=7.5, 4.6 Hz), 3.79 (2H, t, J=6 Hz), 3.78 (2H, dt, J=6, 6 Hz), 1.41 (9H, s).

Referential Example 6

2-[2-[N-(4-Chlorophenyl)-N-t-butoxycarbonyl]aminoethyl] amino-3-aminopyridine

The product of Referential Example 5 (54.50 g) was dissolved in ethyl acetate (500 ml), and then 20% palladium hydroxide on carbon was added thereto, followed by stirring at room temperature under hydrogen atmosphere (1 atm) for about six hours. The catalyst was filtered off and the filtrate was used in subsequent reaction without any additional treatment, $^1$H-NMR(270 MHz, CDCl$_3$) δ: 7.69 (1H, dd, J=4.9, 1.6 Hz), 7.27 (2H, dm, J=8.6 Hz), 7.14 (2H, dm, J=8.6 Hz), 6.81 (1H, dd, J=7.3, 1.6 Hz), 6.50(1H, dd, J=7.3, 4.9 Hz), 4.71 (1H, br), 3.93 (2H, t, J=6 Hz), 3.43 (2H, dt, J=5 Hz), 3.15 (H, br), 1.36 (9H, s).

Example 76

Compound A: 3-(4-Chlorobenzenesulfonyl)amino-2-[2-[N-(4-chlorophenyl)-N-t-butoxycarbonyl]aminoethyl)]aminopyridine Compound B: 3-[N,N-Bis(4-chlorobenzenesulfonyl)amino-2-[2-[N-(4-chlorophenyl)-N-t-butoxycarbonyl]aminoethyl)]-aminopyridine The filtrate of Referential Example 6 was stirred on ice, to which pyridine (17.56 g) and p-chlorobenzenesulfonyl chloride (40.99 g) were sequentially added. The mixture was stirred for 30 min on ice and additionally for one hour at room temperature. The reaction mixture was transferred to a separating funnel and ethyl acetate was added to the mixture. Subsequently, the mixture was washed with water and saturated brine. The aqueous layer was extracted with ethyl acetate (500 ml), washed with saturated brine, combined with the ethyl acetate layer, dehydrated over anhydrous magnesium sulfate, and filtered. After the solvent was removed, the thus-formed residue was purified by silica gel column chromatography (elution solvent=n-hexane:ethyl acetate=4:1), to thereby yield compound A (64.11 g) and compound B (8.90 g) in the form of colorless crystals.

Compound A: $^1$H-NMR(270 MHz, CDCl$_3$) δ: 8.17 (½×1H, dd, J=5.0, 1.7 Hz), 8.10 (½×1H, dd, J=5.0, 1.7 Hz), 7.97 (½×2H, d, J=8.9 Hz), 7.96 (½×2H, d, J=8.9 Hz), 7.55 (½×2H, d, J=8.9 Hz), 7.53 (½×2H, d, J=8.9 Hz), 7.34 (½×2H, d, J=8.6 Hz), 7.23 (½×2H, d, J=8.6 Hz), 7.10 (½×2H, d, J=8.9 Hz), 6.08 (1H, dd, J=7.6, 1.7 Hz), 6.62 (½×1H, dd, J=7.6, 5.0 Hz), 6.61 (½×1H, dd, J=7.6, 5.0 Hz), 6.56 (½×2H, d, J=8.9 Hz), 5.05 (½×1H, brt, J=6 Hz), 5.03 (½×1H, brt, J=6 Hz), 4.08~4.19 (½×1H, m), 3.60~3.95 (½×1H+2H, m), 3.33~3.38 (1H, m), 1.35 (½×9H, s), 1.31 (½×9H, s).

Compound B: $^1$H-NMR(270 MHz, CDCl$_3$) δ: 8.14 (1H, dd, J=4.9, 1.6 Hz), 7.91 (4H, dm, J=8.6 Hz), 7.54 (4H, dm, J=8.6 Hz), 7.28 (2H, dm, J=8.9 Hz), 7.16 (2H, dm, J=8.9 Hz), 6.74 (1H, dd, J=7.6, 1.6 Hz), 6.48 (1H, dd, J=7.6, 4.9 Hz), 5.03 (H, br), 3.74 (2H, brt, J=6 Hz), 3.17 (2H, brq, J=6 Hz), 1.39 (9H, s).

Example 77
3-(4-chlorobenzenesulfonylamino)-2-[2-(4-chlorophenyl) aminoethylamino)]pyridine Ethyl acetate (20 ml) was added to the compound A of Example 76 (1.53 g) to dissolve the compound. 4N HCl-ethyl acetate (7 ml) was added to the resultant solution and the mixture was stirred for 18 hours at room temperature. A sodium hydrogencarbonate solution was added to the resultant mixture to make the mixture alkaline and the product was extracted with ethyl acetate (100 ml). The ethyl acetate layer was washed with water and saturated brine and dehydrated over anhydrous magnesium sulfate. After filtration, the solvent was removed and the residue was purified by means of silica gel column chromatography (elution solvent=n-hexane:ethyl acetate=10:1), to thereby obtain the target compound (1.20 g) as colorless crystals.

$^1$H-NMR(270 MHz, CDCl$_3$) δ: 8.02 (1H, dd, J=5.3, 1.6 Hz), 7.65 (2H, dm, J=8.6 Hz), 7.43 (2H, dm, J=8.6 Hz), 7.10 (2H, dm, J=8.9 Hz), 6.64 (1H, dd, J=7.6, 1.6 Hz), 6.57 (2H, dm, J=8.9 Hz), 6.39 (1H, dd, J=7.6, 5.3 Hz), 5.73 (1H, br), 3.65~3.75 (2H, br), 3.31 (2H, brt, J=6 Hz).

In order to obtain the target compound, the process of Referential Example 4 or Example 74 can be employed for small-scale production. However, in a large scale production, the reaction point shifts and the p-chlorophenylanilino group undergoes sulfonylation. Therefore, the reaction routes as described in Referential Example 5 and subsequent Examples were necessary.

Example 78
3-[N-(2-Bromoethyl)-N-(4-chlorobenzenesulfonyl)amino]-2-[2-[N-(4-chlorophenyl)-N-t-butoxycarbonyl]aminoethyl]aminopyridine The Compound A used in Example 76 (8.25 g) was dissolved in tetrahydrofuran (80 ml). Under ice cooling, to the thus-obtained solution were added triphenylphosphine (5.98 g), 2-bromoethanol (2.86 g), and diisopropylazodicarboxylate (4.26 g) in a sequential manner, followed by stirring at room temperature for 30 minutes. The solvent was removed by evaporation, and the residue was purified by means of silica gel column chromatography (solvent:n-hexane/ethyl acetate=2/1) to yield the target product (8.98 g) as colorless crystals.

$^1$H-NMR(270 MHz, CDCl$_3$) δ: 8.06 (1H, dd, J=5.0, 1.7 Hz), 7.64 (2H, dm, J=8.6 Hz), 7.48 (2H, dm, J=8.6 Hz), 7.10 (2H, dm, J=8.6 Hz), 6.58 (2H, dm, J=8.6 Hz), 6.67 (1H, dd, J=7.6, 1.7 Hz), 6.42 (H, dd, J=7.6, 5.0 Hz), 5.54 (1H, brt, J=5 Hz), 3.99~4.13 (1H, m), 3.76~3.87 (2H, m), 3.55~3.71 (2H, m), 3.38~3.55 (1H, m), 3.24~3.38 (2H, m). 1.44 (9H, s).

Example 79
3-[N-(2-Bromoethyl)-N-(4-chlorobenzenesulfonyl)amino]-2-[2-(4-chlorophenyl)aminoethyl]aminopyridine The product of Example 78 (2.00 g) was dissolved in ethyl acetate (20 ml). Subsequently, 4N HCl (12 ml) was added thereto at room temperature, followed by stirring for 24 hours. A sodium bicarbonate solution was added thereto so as to obtain an alkaline solution, and the thus-obtained alkaline solution was extracted with ethyl acetate (100 ml). The ethyl acetate layer was washed with water and saturated brine in a sequential manner, followed by dehydration over anhydrous magnesium sulfate. The thus-obtained solution was filtered, and the solvent of the filtrate was removed by evaporation. The residue was purified by means of silica gel column chromatography (solvent: chloroform/methanol=10/1) to yield the target product (1.68 g) as colorless amorphous.

$^1$H-NIMR (270 MHz, CDCl$_3$) δ: 8.10 (1H, dd, J=4.9.2.0 Hz), 7.62 (2H, dm, J=8.6 Hz), 7.48 (2H, dm, J=8.6 Hz), 7.10 (2H, dm, J=8.9 Hz), 6.58 (2H, dm, J=8.9 Hz), 6.57 (1H, dd, J=7.7, 2.0 Hz), 6.44 (1H, dd, J=7.7, 4.9 Hz), 5.64 (1H, brt, J=6 Hz), 4.52 (1H, br), 4.17 (1H, m), 3.77 (1H, m), 3.63 (1H, m), 3.47 (1H, m), 3.30~3.38 (4H, m).

In a similar manner, compounds of Examples 80–86 described below were prepared by use of the compound A described in Example 76 and various alcohols.

Example 80
3-[N-(4-Chlorobenzenesulfonyl)-N-(2-methylaminoethyl)]amino-2-[2-(4-chlorophenyl)aminoethyl]aminopyridine $^1$H-NMR(270 MHz, CDCl$_3$) δ: 8.06 (1H, dd, J=5.0, 1.7 Hz), 7.63 (2H, dm, J=8.7 Hz), 7.46 (2H, dm, J=8.7 Hz), 7.09 (2H, dm, J=8.9 Hz), 6.59 (2H, dm, J=8.9 Hz), 6.56 (1H, dd, J=7.6, 1.7 Hz), 6.37 (1H, dd, J=7.6, 5.0 Hz), 4.80 (1H, br), 4.10~4.20 (1H, m), 3.81~3.90 (1H, m), 3.45~3.56 (1H, m), 3.25~3.40 (2H, m), 3.04~3.12 (1H, m), 2.51~2.67 (2H, m), 2.37 (3H, s).

Example 81
3-[N-(3-Aminopropyl)-N-(4-chlorobenzenesulfonyl)]amino-2-[2-(4-chlorophenyl)aminoethyl]aminopyridine $^1$H-NMR(270 MHz, CDCl$_3$) δ: 8.05 (1H, t, J=3.3 Hz), 7.68 (2H, d, J=8.5 Hz), 7.44 (2H, d, J=8.5 Hz), 7.01 (2H, d, J=8.6 Hz), 6.53 (2H, d, J=8.6 Hz), 6.36 (2H, d, J=3.3 Hz), 6.17 (1H, brt, J=6 Hz), 4.75 (1H, br), 4.35~4.43 (1H, m), 3.60~3.75 (2H, m), 3.15~3.35 (3H, m), 2.95~3.10 (2H, m), 1.75~2.00 (2H, m).

Example 82
3-[N-(4-Chlorobenzenesulfonyl)-N-(2-pyrrolidinoethyl)]amino-2-[2-(4-chlorophenyl)aminoethyl]aminopyridine $^1$H-NMR(270 MHz, CDCl$_3$) δ: 8.05 (1H, dd, J=5.0, 1.7 Hz), 7.64 (2H, dm, J=8.6 Hz), 7.46 (2H, dm, J=8.6 Hz), 7.10 (2H, dm, J=8.9 Hz), 6.61 (2H, dm, J=8.9 Hz), 6.55 (1H, dd, J=7.6, 1.7 Hz), 6.36 (1H, dd, J=7.6, 5.0 Hz), 4.79 (1H, br), 4.15~4.26 (1H, m), 3.86~3.94 (1H, m), 3.00~3.07 (1H, m), 2.60~2.73 (3H, m), 2.22~2.40 (3H, m), 1.60~1.75 (4H, m).

Example 83
3-[N-4-Chlorobenzenesulfonyl]-N-[2-( 2-hydroxyethyl)amonoethyl]amino-2-[2-(4-chlorophenyl)aminoethyl] aminopyridine $^1$H-NMR(270 MHz, CDCl$_3$) δ: 8.06 (H, dd, J=5.0, 1.7 Hz), 7.56 (2H, dm, J=8.7 Hz), 7.39 (2H, dm, J=8.7 Hz), 7.08 (2H, dm, J=8.9 Hz), 6.78 (1H, dd, J=7.6, 1.7 Hz), 6.53 (2H, dm, J=8.9 Hz), 6.43 (1H, dd, J=7.6, 5.0 Hz), 4.79 (1H, br), 4.28~4.44 (2H, m), 4.10~4.20 (1H, m), 3.80 (1H, dt, J=7.9, 1.7 Hz), 3.44~3.70 (4H, m), 3.19~3.33 (4H, m).

Example 84
3-[N-(4-Chlorobenzenesulfonyl)-N-(3-piperidinomethyl)]amino-2-[2-(4-chlorophenyl)aminoethyl]aminopyridine $^1$H-NMR(270 MHz, CDCl$_3$) δ: 8.13 (½×1H, dd, J=5.0, 1.7 Hz), 8.12 (½×1H, dd, J=5.0, 1.7 Hz), 7.67 (½×2H, d, J=8.9 Hz), 7.66 (½×2H, d, J=8.9 Hz), 7.46 (½×2H, d, J=8.9 Hz), 7.45 (½×2H, d, J=8.9 Hz), 7.09 (2H, d, J=8.9 Hz), 6.63 (½×1H, dd, J=7.6, 1.7 Hz), 6.62 (½×1H, dd, J=7.6, 1.7 Hz), 6.57 (½×2H, d, J=8.9 Hz), 6.56 (½×2H, d, J=8.9 Hz), 6.46 (½×1H, dd, J=7.6, 5.0 Hz), 6.45 (½×1H, dd, J=7.6, 5.0 Hz), 5.50 (½×1H, brt, J=6 Hz), 5.46 (½×1H, brt, J=6 Hz), 4.48 (1H, br), 4.08~4.25 (1H, m), 3.71~3.84 (1H, m), 3.49~3.60 (1H, m), 3.23~3:.40 (2H, m), 2.80~2.94 (2H, m), 2.13~2.41 (3H, m), 2.00~2.12 (1H, m), 1.40~1.70 (2H, m), 1.08~1.35 (2H, m).

Example 85
3-[N-(4-Chlorobenzenesulfonyl)-N-(2-piperidinomethyl)]amino-2-[2-(4-chlorophenyl)aminoethyl]aminopyridine $^1$H-NMR(270 MHz, CDCl$_3$) δ: 8.05 (1H, dd, J=5.0, 1.7 Hz), 7.62 (2H, dm, J=8.6 Hz), 7.46 (2H, dm, J=8.6 Hz), 7.09 (2H, dm, J=8.9 Hz), 6.60 (2H, dm, J=8.9 Hz), 6.54 (1H, dd, J=7.6, 1.7 Hz), 6.33 (1H, dd, J=7.6, 5.0 Hz), 3.78~3.92 (3H, m), 3.25~3.50 (2H, m), 2.94~3.03 (2H, m), 2.34~2.52 (2H, m), 1.75~1.85 (1H, m), 1.42~1.58 (3H, m), 1.23~1.33 (2H, m).

Example 86
3-[N-(4-Chlorobenzenesulfonyl)-N-(2-aminoethyl)]amino-2-[2-(4-chlorophenyl)aminoethyl]aminopyridine $^1$H-NMR(270 MHz, CDCl$_3$) δ: 8.07 (1H, dd, J=5.0, 1.6 Hz), 7.62 (2H, dm, J=8.6 Hz), 7.46 (2H, dm, J=8.6 Hz), 7.09 (2H, dm, J=8.9 Hz), 6.58 (2H, dm, J=8.9 Hz), 6.57 (1H, dd, J=7.6, 1.6 Hz), 6.40 (1H, dd, J=7.6, 5.0 Hz), 3.93~4.03 (1H, m), 3.74~3.85 (1H, m), 3.51~3.62 (1H, m), 3.26~3.42 (2H, m), 3.04~3.12 (1H, m), 2.79~2.87 (1H, m), 2.59~2.69 (1H, m).

Example 87
3-N,N-Bis(4-chlorobenzenesulfonyl)amino-2-[2-(4-chlorophenyl)aminoethyl]aminopyridine The Compound B used in Example 76 was dissolved in ethyl acetate (20 ml). Subsequently, 4N HCl (10 ml) was added thereto, followed by stirring at room temperature for 20 hours. A sodium bicarbonate solution was added thereto so as to obtain an alkaline solution, and the thus-obtained alkaline solution was extracted with ethyl acetate (100 ml). The ethyl acetate layer was washed with water and saturated brine in a sequential manner, followed by dehydration over anhydrous magnesium sulfate. The thus-obtained solution was filtered, and the solvent of the filtrate was removed by evaporation. The residue was purified by means of silica gel column chromatography (solvent: chloroform/methanol=10/1) to yield the target product (0.94 g) as colorless amorphous.

$^1$H-NMR(270 MHz, DMSO-d$_6$) δ: 8.23 (1H, dd, J=4.8, 1.7 Hz), 7.97 (4H, dm, J=8.8 Hz), 7.83 (4H, dm, J=8.8 Hz), 7.28 (2H, dm, J=8.9 Hz), 7.02 (1H, dd, J=7.9, 1.7 Hz), 6.87 (2H, dm, J=8.9 Hz), 6.85 (1H, br), 6.73 (1H, dd, J=7.9, 4.8 Hz), 3.62 (2H, brq, J=6.6 Hz), 3.17 (2H, brt, J=6.6 Hz).

$^1$H-NMR(270 MHz, CDCl$_3$) δ: 8.19 (1H, dd, J=4.9, 1.6 Hz), 7.87 (4H, dm, J=8.6 Hz), 7.47 (4H, dm, J=8.6 Hz), 7.13 (2H, dm, J=8.6 Hz), 6.53 (2H, dm, J=8.6 Hz), 6.83 (1H, dd, J=7.6, 1.6 Hz), 6.55 (1H, dd, J=7.6, 4.9 Hz), 4.84 (1H, brt, J=6 Hz), 3.55 (2H, brq, J=6 Hz), 3.20 (2H, brt, J=6 Hz),

Example 88
3-[N-(4-Chlorobenzenesulfonyl)-N-(2-t-butoxycarbonylaminoethyl)]amino-2-[4-(4-chlorophenyl)-2,3-dioxo-1-piperadino]pyridine The product of Example 75 (1.52 g) was dissolved in methylene chloride (30 ml). Under stirring in an ice bath, oxalyl chloride (0.50 g) and triethylamine (0.80 g) were sequentially added to the thus-obtained solution, followed by stirring at room temperature for 1 hour. Subsequently, chloroform (100 ml) was added to the resultant solution, and the mixture was washed twice with water. The aqueous layer was extracted with chloroform, and the combined chloroform layer was washed with saturated brine, followed by dehydration over magnesium sulfate. The thus-obtained solution was filtered, and the solvent of the filtrate was evaporated under reduced pressure. The residue was purified by means of silica gel column chromatography (solvent: chloroform/methanol=10/1) to yield the target product (1.53 g) as colorless amorphous.

$^1$H-NMR(270 MHz, CDCl$_3$) δ: 8.52 (1H, dd, J=4.6, 1.6 Hz), 7.50 (2H, d, J=8.8 Hz), 7.46 (2H, d, J=8.8 Hz), 7.43 (4H, s), 7.27 (1H, dd, J=7.9, 4.6 Hz), 7.14 (1H, dd, J=7.9. 1.6 Hz), 5.45 (1H, brt, J=5 Hz), 4.47~4.64 (2H, m), 3.95~4.07 (1H, m), 3.85~3.95 (1H, m), 3.73~3.85 (1H, m), 3.30~3.45 (3H, m), 1.32 (9H, s).

Referential Example 7
2-[4-(4-Chlorophenyl)-2,3-dioxo-1-piperadino]-3-nitropyridine The product of Referential Example 3 (3.10 g) was dissolved in methylene chloride (30 ml). Under stirring in an ice bath, oxalyl chloride (1.61 g) and triethylamine (3.21 g) were sequentially added to the resultant solution, followed by stirring at room temperature for 1 hour. Subsequently, chloroform (100 ml) was added to the resultant solution, and the mixture was washed twice with water. The aqueous layer was extracted with chloroform, and the combined chloroform layer was washed with saturated brine, followed by dehydration over magnesium sulfate. The thus-obtained solution was filtered, and the solvent of the filtrate was evaporated under reduced pressure. The yellow residue was purified by means of silica gel column chromatography (solvent: chloroform/methanol=10/1) to yield the target product (2.00 g) as colorless crystals.

$^1$H-NMR(270 MHz, CDCl$_3$) δ: 8.55 (1H, dd, J=4.6, 1.6 Hz), 8.23 (1H, dd, J=7.9. 1.6 Hz), 7.44 (2H, dm, J=8.9 Hz), 7.38 (2H, dm, J=8.9 Hz), 7.37 (1H, dd, J=7.9, 4.6 Hz), 4.69 (2H, m), 4.33 (2H, m).

Referential Example 8
3-Amino-2-[4-(4-chlorophenyl)-2,3-dioxo-1-piperadino]pyridine The product of the Referential Example 7 (2.00 g) was suspended in ethanol (50 ml) and methanol (10 ml). To the resultant suspension, 20% palladium hydroxide on carbon (0.50 g) was added, followed by stirring at room temperature for 1 hour under hydrogen gas (1 atm). The catalyst was filtered off, and the solvent of filtrate was evaporated under reduced pressure. The residue was purified by means of silica gel column chromatography (solvent: chloroform/methanol=10/1) to yield the target product (1.10 g) as colorless crystals. Unreacted starting compound (0.22 g) as colorless crystals was also obtained.

$^1$H-NMR(270 MHz, CDCl$_3$) δ: 7.98 (1H, dd, J=4.0, 2.0 Hz), 7.42 (2H, dm, J=9 Hz), 7.37 (2H, dm, J=9 Hz), 7.12~7.20 (2H, m), 4.33 (2H, m), 4.15 (2H, m), 4.07 (2H, brs).

Example 89

3-(4-Chlorobenzenesulfonylamino)-2-[4-(4-chlorophenyl)-2,3-dioxo-1-piperadino]pyridine The product of Referential Example 8 (1.05 g) was dissolved in chloroform (40 ml). Under stirring in an ice bath, to the resultant solution were added pyridine (0.31 g) and p-chlorobenzenesulfonylchloride (0.84 g) in a sequential manner. Subsequently the resultant solution was stirred at room temperature for 18 hours and then at 50° C. for 2 hours. Subsequently, chloroform (100 ml) was added to the resultant solution, and the mixture was washed twice with water. The aqueous layer was extracted with chloroform, and the combined chloroform layer was washed with saturated brine, followed by dehydration over magnesium sulfate. The thus-obtained solution was filtered, and the solvent of the filtrate was evaporated under reduced pressure. The yellow residue was purified by means of silica gel column chromatography (solvent: chloroform/methanol=10/1) to yield the target product (1.20 g) as colorless crystals. The starting compound (product of Referential Example 8) (0.19 g) was also obtained as colorless crystals.

$^1$H-NMR(270 MHz, CDCl$_3$) δ: 8.37 (1H, dd, J=4.6, 1.6 Hz), 7.77 (1H, dd, J=8.6, 1.6 Hz), 7.73 (2H, dm, J=8.6 Hz), 7.66 (1H, br), 7.46 (2H, dm, J=8.6 Hz), 7.42 (2H, dm, J=8.9 Hz), 7.33 (2H, dm, J=8.9 Hz), 7.32 (1H, dd, J=8.6, 4.6 Hz), 3.98 (2H, m), 3.92 (2H, m).

Example 90

3-[N-(2-Bromoethyl)-N-(4-chlorobenzenesulfonyl)]amino-2-(4-(4-chlorophenyl)-2,3-dioxo-1-piperadino]pyridine The product of Example 89 (0.45 g) was dissolved in tetrahydrofuran (20 ml). Under ice cooling, to the thus-obtained solution were added triphenylphosphine (289 mg), 2-bromoethanol (137 mg), and diisopropylazodicarboxylate (222 mg) in a sequential manner, followed by stirring at room temperature for 30 minutes. The solvent was removed by evaporation, and the residue was purified by means of silica gel column chromatography (solvent: n-hexane/ethyl acetate=2/1) to yield the target product (529 mg) as colorless amorphous.

$^1$H-NMR(270 MHz, CDCl$_3$) δ: 8.56 (1H, dd, J=4.8, 1.8 Hz), 7.53 (4H, s), 7.42 (4H, s), 7.32 (1H, dd, J=8.0, 4.8 Hz), 7.11 (1H, dd, J=8.0, 1.8 Hz), 4.3~4.5 (2H, br), 3.8~4.2 (2H, br), 3.5~3.8 (4H, br).

Example 91

3-[N-(4-Chlorobenzenesulfonyl)-N-(2-t-butoxycarbonylaminoethyl)amino-2-[4-(4-chlorophenyl)-2,3-dioxo-1-piperadino]pyridine The product of Example 89 (422 mg) was dissolved in tetrahydrofuran (20 ml). Under ice cooling, to the thus-obtained solution were added triphenylphosphine (338 mg), N-t-butoxycarbonyl-aminoethanol (207.7 mg), and diisopropylazodicarboxylate (260.4 mg) in a sequential manner, followed by stirring at room temperature for 30 minutes. The solvent was removed by evaporation, and the residue was purified by means of silica gel column chromatography (solvent: n-hexane/ethyl acetate) to yield the target product as colorless amorphous (529 mg).

$^1$H-NMR(270 MHz, CDCl$_3$) δ: 8.52 (1H, dd, J=4.6, 1.6 Hz), 7.50 (2H, d, J=8.8 Hz), 7.46 (2H, d, J=8.8 Hz), 7.43 (4H, s), 7.27 (1H, dd, J=7.9, 4.6 Hz), 7.14 (1H, dd, J=7.9, 1.6 Hz), 5.45 (1H, brt, J=5 Hz), 4.47~4.64 (2H, m), 3.95~4.07 (1H, m), 3.85~3.95 (1H, m), 3.73~3.85 (1H, m), 3.30~3.45 (3H, m), 1.32 (9H, s).

Example 92

3-[N-(4-Chlorobenzenesulfonyl)-N-(2-aminoethyl)]amino-2-[4-(4-chlorophenyl)-2,3-dioxo-1-piperadino]pyridine The product of Example 91 (529 mg) was dissolved in ethyl acetate (10 ml). Subsequently, 4N HCl (6 ml) was added thereto at room temperature, followed by stirring for 24 hours. A sodium bicarbonate solution was added thereto so as to obtain an alkaline solution, and the thus-obtained alkaline solution was extracted with ethyl acetate (100 ml). The ethyl acetate layer was washed with water and saturated brine in a sequential manner, followed by dehydration over anhydrous magnesium sulfate. The thus-obtained solution was filtered, and the solvent of the filtrate was removed by evaporation. The residue was purified by means of silica gel column chromatography (solvent: chloroform/methanol=10/1) to yield the target product (441 mg) as colorless amorphous.

$^1$H-NMR(270 MHz, CDCl$_3$) δ: 8.50 (1H, dd, J=4.6, 1.4 Hz), 7.46 (4H, s), 7.40 (2H, d, J=6.3 Hz, AB-type), 7.38 (2H, d, J=6.3 Hz, AB-type), 7.28 (1H, dd, J=8.0, 4.6 Hz), 7.19 (1H, dd, J=8.0, 1.4 Hz), 4.45~4.60 (2H, br), 3.80~4.05 (2H, br), 3.40~3.60 (1H, br), 2.80~3.20 (3H, br).

In a manner similar to that described in Examples 78 and 79, compounds of Examples 93–123 were prepared.

Example 93

3-[N-(4-Chlorobenzenesulfonyl)-N-(2-dimethylaminoethyl)]amino-2-[2-(4-chlorophenyl)aminoethyl]aminopyridine $^1$H-NMR(270 MHz, CDCl3) δ: 8.05 (1H, dd, J=4.95, 1.65 Hz), 7.62 (2H, d, J=8.91 Hz), 7.45 (2H, d, J=8.91 Hz), 7.09 (2H, d, J=8.91 Hz), 6.60 (2H, d, J=8.91 Hz), 6.55~6.11 (1H, m), 6.34~6.39 (1H, m), 4.67~4.88 (1H, br), 4.12~4.27 (1H, m), 3.81~3.96 (1H, m), 3.16~3.52 (3H, m), 2.92~3.05 (1H, m), 2.39 (1H, ddd, J=12.87, 10.56, 4.62 Hz), 2.21 (6H, s), 2.06~2.22 (1H, m).

Example 94

3-[N-[2-(2-Aminoethoxy)ethyl]-N-(4-chlorobenzenesulfonyl)]amino-2-[2-(4-chlorophenyl)aminoethyl]aminopyridine $^1$H-NMR(270 MHz, CDCl$_3$) δ: 8.07 (1H, dd, J=4.95, 1.65 Hz), 7.64 (2H, d, J=8.91 Hz), 7.47 (2H, d, J=8.58 Hz), 7.09 (2H, d, J=8.90 Hz), 6.57 (2H, d, J=8.91 Hz), 6.50~6.65 (1H, m), 6.37~6.42 (1H, m), 6.05 (1H, t, J=6.11 Hz), 4.08~4.19 (1H, m), 3.69~3.89 (1H, m), 3.22~3.75 (7H, m), 3.13~3.21 (1H, m), 2.65~2.87 (2H, m).

Example 95

3-[N-(4-Chlorobenzenesulfonyl)-N-(2-piperidyl)ethyl]]amino-2-[2-(4-chlorophenyl)aminoethyl]aminopyridine $^1$H-NMR(270 MHz, CDCl$_3$) δ: 8.07 (1H, dd, J=4.93, 1.65 Hz), 7.61 (2H, d, J=8.58 Hz), 7.47 (2H, d, J=8.58 Hz), 7.10 (2H, d, J=8.91 Hz), 6.59 (2H, d, J=8.91 Hz), 6.48~6.52 (1H, m), 6.36~6.42 (1H, m), 5.84 (1H, t, J=6.27 Hz), 4.33~4.87 (1H, br), 3.74~4.06 (2H, m ), 3.50~3.69 (1H, m), 3.25~3.48 (2H, ), 3.05~3.17 (1H, m), 2.90~3.04 (1H, m), 2.43~2.62 (2H, m), 1.18~1.90 (8H, m), 0.94~1.09 (1H, m).

Example 96

3-[N-(4-Chlorobenzenesulfonyl)-N-[2-(3-nitro-2-pyridyl)aminoethyl]]amino-2-[2-( 4-chlorophenyl)aminoethyl]aminopyridine $^1$H-NMR(270 MHz, CDCl$_3$) δ: 8.37 (1H, dd, J=8.25, 1.65 Hz), 8.25~8.33 (2H, m), 8.09 (1H, dd, J=4.95, 1.65 Hz), 7.60 (2H, d, J=8.58 Hz), 7.42 (2H, d, J=8.58 Hz), 7.07 (2H, d, J=8.90 Hz), 6.55 (2H, d, J=8.91 Hz), 6.54~6.68 (2H, m), 6.41~6.46 (1H, m), 5.71 (1H t, J=6.10 Hz), 4.43~4.54 (1H, br), 4.16~4.25 (1H, m), 3.73~3.91 (2H, m), 3.52~3.67 (1H, m), 3.25~3.50 (4H, m).

Example 97
3-[N-(4-Chlorobenzenesulfonyl)-N-[2-(1-piperazinyl)ethyl]]amino-2-[2-(4-chlorophenyl)aminoethyl]aminopyridine $^1$H-NMR(270 MHz, CDCl$_3$) δ: 8.04~8.07 (1H, m), 7.62 (2H, d, J=8.58 Hz), 7.47 (2H, d, J=8.91 Hz), 7.10 (2H, d, J=8.58 Hz), 6.78 (2H, d, J=8.90 Hz), 6.51~6.55 (1H, m), 6.34~6.39 (1H, m), 4.70~5.00 (1H, br), 4.13~4.32 (1H, m), 3.84~4.02 (1H, m), 3.19~3.50 (3H, m), 2.86~3.04 (1H, m), 2.38~2.88 (4H, br), 2.33~2.49 (1H, m), 2.01~2.32 (3H, m), 1.39~1.81 (1H, br).

Example 98
3-[N-[2-(3-Amino-2-pyridyl)aminoethyl]-N-(4-chlorobenzenesulfonyl)]amino-2-[2-(4-chlorophenyl)aminoethyl]aminopyridine $^1$H-NMR(270 MHz, CDCl$_3$) δ: 8.05 (1H, dd, J=4.95, 1.65 Hz), 7.61 (3H, m), 7.43 (2H, d, J=8.58 Hz), 7.07 (2H, d, J=8.57 Hz), 6.60 (1H, d, J=1.65 Hz), 6.58 (1H, d, J=1.65 Hz), 6.50 (3H, m), 6.38~6.48 (1H, m), 5.88 (1H, t, J=5.94 Hz), 4.30~5.00 (2H, br), 4.19~4.22 (1H, m), 2.70~3.79 (10H, m).

Example 99
3-[N-(2-Aminophenyl)methyl-N-(4-chlorobenzenesulfonyl)]amino-2-[2-(4-chlorophenyl)aminoethyl]aminopyridine $^1$H-NMR(270 MHz, CDCl$_3$) δ: 7.94 (1H, dd, J=4.95, 1.65 Hz), 7.71 (2H, d, J=8.91 Hz), 7.52 (2H, d, J=8.57 Hz), 7.10 (2H, d, J=8.91 Hz), 6.97~7.07 (1H, m), 6.58~6.67 (2H, m), 6.50 (2H, d, J=8.91 Hz), 6.42~6.52 (m, 2H), 6.33~6.38 (1H, m), 5.93 (1H, t, J=5.94 Hz), 5.24 (1H, d, J=13.53 Hz), 4.10~4.51 (3H, br), 3.83 (1H, d, J=13.53 Hz), 3.26~3.45 (2H, m), 2.97~3.16 (2H, m).

Example 100
3-[N-[2-(4-Aminophenyl)ethyl]-N-(4-chlorobenzenesulfonyl)]amino-2-[2-(4-chlorophenyl)aminoethyl]aminopyridine $^1$H-NMR(270 MHz, CDCl$_3$) δ: 8.06~8.09 (1H, m), 7.57 (2H, d, J=8.58 Hz), 7.45 (2H, d, J=8.58 Hz), 7.10 (2H, d, J=8.91 Hz), 6.87 (2H, d, J=8.25 Hz), 6.50~6.58 (5H, m), 6.39~6.44 (m, 1H), 5.33 (1H, t, J=5.94 Hz), 4.40~4.65 (1H, br), 4.00~4.13 (1H, m), 3.72~3.84 (1H, m), 3.50~3.70 (1H, br), 3.14~3.49 (4H, m), 2.53~2.72 (2H, m).

Example 101
2-[2-(4-Chlorophenyl)aminoethyl]amino-3-[N-[2-(4-morpholino)ethyl]-N-(4-chlorobenzenesulfonyl)]aminopyridine $^1$H-NMR(270 MHz, CDCl$_3$) δ: 8.06 (1H, dd, J=4.62, 1.65 Hz), 7.62 (2H, d, J=8.58 Hz), 7.48 (2H, d, J=8.91 Hz), 7.11 (2H, d, J=8.91 Hz), 6.64~6.75 (1H, m), 6.63 (2H, d, J=8.90 Hz), 6.52 (1H, dd, J=7.59, 1.98 Hz), 6.37 (1H, dd, J=7.59, 4.95 Hz), 4.62~5.1 (1H, br), 4.17~4.30 (1H, m), 3.89~4.03 (1H, m), 3.56~3.59 (4H, m), 3.22~3.55 (3H, m), 2.92~3.04 (1H, m), 2.50~2.77 (2H, m), 2.37~2.50 (1H, m), 2.10~2.36 (3H, m).

Example 102
3-[N-(3-Bromopropyl)-N-(4-chlorobenzenesulfonyl)]amino-2-[2-(4-chlorophenyl)aminoethyl]aminopyridine $^1$H-NMR(270 MHz, CDCl$_3$) δ: 8.09 (1H, dd, J=4.62, 1.65 Hz), 7.62 (2H, d, J=8.91 Hz), 7.50 (2H, d, J=8.58 Hz), 7.10 (2H, d, J=8.91 Hz), 6.58 (2H, d, J=8.91 Hz), 6.49~6.59 (1H, m), 6.38~6.52 (1H, m), 5.60 (1H, t, J=5.78 Hz), 3.92~4.08 (1H, m), 3.74~3.91 (1H, m), 3.25~3.72 (5H, m), 3.10~3.24 (1H, m), 1.74~2.20 (1H, m).

Example 103
3-[N-(4-Chlorobenzenesulfonyl)-N-[2-(imidazole-1-yl)ethyl]]amino-2-[2-(4-chlorophenyl)aminoethyl]aminopyridine $^1$H-NMR(270 MHz, CDCl$_3$) δ: 8.06~8.15 (1H, m), 7.54 (2H, d, J=8.90 Hz), 7.46 (2H, d, J=8.58 Hz), 7.42 (1H, brs), 7.11 (2H, d, J=8.91 Hz), 7.05 (1H, brs), 6.90 (1H, brs), 6.59 (2H, d, J=8.91 Hz), 6.48~6.52 (1H, m), 6.40~6.47 (1H, m), 5.12 (1H, t, J=5.94 Hz), 3.98~4.27 (3H, m), 3.62~3.81 (1H, m), 3.23~3.54 (4H, m).

Example 104
3-[N-(4-Chlorobenzenesulfonyl)-N-(3-N-methylaminopropyl)]amino-2-[2-(4-chlorophenyl)aminoethyl]aminopyridine $^1$H-NMR(270 MHz, CDCl$_3$) δ: 8.07 (1H, m), 7.62 (2H, d, J=8.58 Hz), 7.48 (2H, d, J=8.58 Hz), 7.10 (2H, d, J=8.91 Hz), 6.59 (2H, d, J=8.91 Hz), 6.45~6.53 (1H, m), 6.37~6.42 (1H, m), 6.09 (1H, t, J=5.94 Hz), 4.52~4.75 (1H, br), 3.78~3.99 (2H, m), 3.50~3.69 (1H, m), 3.25~3.44 (2H, m), 3.10 (1H, dq, J=7.58, 5.28 Hz), 2.59 (2H, ddd, J=25.73, 12.20, 6.60 Hz), 2.32 (3H, s), 1.37~1.72 (2H, m).

Example 105
3-[N-(4-Chlorobenzenesulfonyl)-N-[2-(imidazole-2-yl)thioethyl]]amino-2-[2-(4-chlorophenyl)aminoethyl]aminopyridine $^1$H-NMR(270 MHz, CDCl$_3$) δ: 8.07 (1H, dd, J=4.95, 1.65 Hz), 7.57 (2H, d, J=8.91 Hz), 7.45 (2H, d, J=8.58 Hz), 7.08 (2H, d, J=8.90 Hz), 6.90~7.21 (2H, m), 6.57 (2H, d, J=8.91 Hz), 6.42~6.51 (1H, m), 6.34~6.42 (1H, m), 5.94 (1H, t, J=5.94 Hz), 4.30~5.10 (1H, br), 3.92~4.06 (1H, m), 3.59~3.84 (2H, m), 3.28~3.40 (3H, m). 3.26 (1H, dt, J=13.52, 4.62 Hz), 2.97~3.18 (1H, m), 2.69~2.86 (1H, m).

Example 106
2-[2-(4-Chlorophenoxy)ethyl]amino-3-[N-(2-aminoethyl)-N-(4-chlorobenzenesulfonyl)]aminopyridine $^1$H-NMR(270 MHz, CDCl$_3$) δ: 8.07 (1H, dd, J=4.95, 1.65 Hz), 7.65 (2H, d, J=8.91 Hz), 7.44 (2H, d, J=8.91 Hz), 7.23 (2H, d, J=8.90 Hz), 6.85 (2H, d, J=8.91 Hz), 6.69 (1H, dd, J=7.59, 1.65 Hz), 6.59 (1H, brt, J=5.78 Hz), 6.43 (1H, dd, J=7.59, 4.95 Hz), 3.85~4.18 (4H, m), 3.66~3.77 (1H, m), 3.10 (1H, dt, J=13.5, 4.45 Hz), 2.77~2.86 (1H, m), 2.59~2.69 (1H, m).

Example 107
2-[2-(4-Chlorophenoxy)ethyl]amino-3-[N-[2-(2-aminoethoxy)ethyl]-N-(4-chlorobenzenesulfonyl)]aminopyridine $^1$H-NMR(270 MHz, CDCl$_3$) δ: 8.08 (1H, dd, J=4.95, 1.65 Hz), 7.65 (2H, d, J=8.58 Hz), 7.43 (2H, d, J=8.58 Hz), 7.23 (2H, d, J=8.90 Hz), 6.87 (2H, d, J=8.91 Hz), 6.75 (1H, dd, J=7.59, 1.65 Hz), 6.45 (1H, dd, J=7.59, 4.95 Hz), 5.89 (1H, brt, J=5.78 Hz), 4.00~4.16 (3H, m), 3.83 (2H, q, J=5.61 Hz), 3.45 (2H, t, J=5.45 Hz), 3.25~3.39 (3H, m), 2.75 (2H, t, J=5.12 Hz).

Example 108
2-[2-(4-Chlorophenoxy)ethyl]amino-3-[N-(2-dimethylaminoethyl)-N-(4-chlorobenzenesulfonyl)]aminopyridine $^1$H-NMR(270 MHz, CDCl$_3$) δ: 8.06 (1H, dd, J=4.95, 1.65 Hz), 7.63 (2H, d, J=8.91 Hz), 7.37 (2H, d, J=8.57 Hz), 7.25 (2H, d, J=8.91 Hz), 6.88 (2H, d, J=9.24 Hz), 6.83~6.91 (2H, m), 6.44 (1H, dd, J=7.59, 4.95 Hz), 4.05~4.22 (2H, m), 3.82~3.99 (2H, m), 3.58~3.71 (1H, m), 3.00~3.08 (1H, m), 2.35~2.45 (1H, m), 2.14~2.29 (1H, m), 2.20 (6H, s).

Example 109
2-[2-(4-Chlorophenylthio)ethyl]amino-3-[N-(2-aminoethyl)-N-(4-chlorobenzenesulfonyl)]aminopyridine $^1$H-NMR(270 MHz, CDCl$_3$) δ: 8.07 (1H, dd, J=4.95, 1.65 Hz), 7.65 (2H, d, J=8.58 Hz), 7.47 (2H, d, J=8.58 Hz), 7.36 (2H, d, J=8.58 Hz), 7.26 (2H, d, J=8.58 Hz), 6.65 (1H, dd, J=7.59, 1.65 Hz), 6.46 (1H, br), 6.43 (1H, dd, J=7.59, 4.95 Hz), 3.91~4.02 (1H, m), 3.47~3.76 (2H, m), 3.03~3.26 (3H, m), 2.60~2.89 (2H, m).

Example 110
2-[2-(4-Chlorophenylthio)ethyl]amino-3-[N-(2-dimethylaminoethyl)-N-(4-chlorobenzenesulfonyl)]aminopyridine $^1$H-NMR(270 MHz, CDCl$_3$) δ: 8.06 (1H, dd, J=4.95, 1.65 Hz), 7.65 (2H, d, J=8.58 Hz), 7.45 (2H, d, J=8.58 Hz), 7.40 (2H, d, J=8.58 Hz), 7.27 (2H, d, J=8.58 Hz), 6.75 (1H, dd, J=7.59, 1.65 Hz), 6.75 (1H, br), 6.42 (1H, dd, J=7.59, 4.95 Hz), 4.10~4.21 (1H, m), 3.65~3.78 (1H, m), 3.37~3.50 (1H, m), 3.12~3.22 (1, m), 2.95~3.07 (2H, m), 2.34~2.45 (1H, m), 2.14~2.27 (1H, m), 2.22 (6H, s).

Example 111
2-[2-[N-(4-Chlorophenyl)-N-(4-chlorobenzenesulfonyl)]aminoethyl]amino-3-[N-(2-aminoethyl)-N-(4-chlorobenzenesulfonyl)]aminopyridine $^1$H-NMR(270 MHz, CDCl$_3$) δ: 8.00 (1H, m), 7.64 (2H, d, J=8.91 Hz), 7.60~7.37 (6H, m), 7.34 (2H, m), 7.06 (2H, m), 6.72~6.37 (3H, m), 4.08~3.72 (2H, m), 3.63 (2H, m), 3.38~3.06 (2H, m), 3.00~2.60 (2H, m).

Example 112
3-[N-(2-Aminoethyl)-N-(4-methoxybenzenesulfonyl)]amino-2-[2-(4-methoxyphenyl)aminoethyl]aminopyridine $^1$H-NMR(270 MHz, CDCl$_3$) δ: 7.95 (1H, dd, J=4.95, 1.32 Hz), 7.52 (2H, d, J=8.57 Hz), 6.83 (2H, d, J=8.58 Hz), 6.67 (2H, d, J=8.58 Hz), 6.54 (2H, d, J=8.91 Hz), 6.46~6.47 (1H, br), 6.26~6.34 (1H, m), 3.78~3.88 (1H, m), 3.73 (3H, s), 3.62 (3H, s), 3.44~3.56 (1H, m), 3.15~3.36 (2H, m), 2.91~2.99 (1H, m), 2.63~2.71 (1H, m), 2.46~2.56 (1H, m).

Example 113
2-[2-(4-Chlorophenyl)aminoethoxy]-3-[N-(2-aminoethyl)-N-(4-chlorobenzenesulfonyl)]aminopyridine $^1$H-NMR(270 MHz, CDCl$_3$) δ: 8.13 (1H, dd, J=4.95, 1.65 Hz), 7.62 (2H, d, J=8.42 Hz), 7.42 (2H, d, J=8.42 Hz), 7.32 (1H, dd, J=7.71, 1.77 Hz), 7.10 (2H, d, J=8.90 Hz), 6.90 (1H, dd, J=7.71, 4.62 Hz), 6.55 (2H, d, J=8.90 Hz), 4.41 (2H, t), 3.55 (2H, t), 3.30 (2H, t), 2.68 (2H, m).

Example 114
3-[N-(2-Aminoethyl)-N-(p-toluenesulfonyl)]amino-2-[2-(p-tolyl)aminoethyl]aminopyridine $^1$H-NMR(270 MHz, CDCl$_3$) δ: 7.95~7.97 (1H, m), 7.48 (2H, d, J=7.92 Hz), 7.18 (2H, d, J=8.25 Hz), 6.88 (2H, d, J=8.25 Hz), 6.50 (2H, d, J=8.25 Hz), 6.45~6.48 (1H, m), 6.26~6.30 (1H, m), 3.80~3.90 (1H, m), 3.49~3.69 (2H, m), 3.23~3.27 (2H, m), 2.92~3.00 (1H, m), 2.64~2.75 (1H, m), 2.48~2.62 (1H, m), 2.33 (3H, s), 2.14 (3H, s).

Example 115
2-[2-[N-Acetyl-N-(4-chlorophenyl)]aminoethyl]amino-3-[N-(2-aminoethyl)-N-(4-chlorobenzenesulfonyl)]aminopyridine $^1$H-NMR(270 MHz, CDCl$_3$) δ: 8.03 (1H, dd, J=4.95, 1.65 Hz), 7.65 (2H, d, J=8.58 Hz), 7.48 (2H, d, J=8.58 Hz), 7.39 (2H, d, J=8.57 Hz), 7.24 (2H, d, J=8.57 Hz), 6.56 (1H, dd, J=7.59, 1.65 Hz), 6.41 (1H, m), 6.38 (1H, dd, J=7.59, 4.95 Hz), 4.35 (1H, m), 3.93 (1H, m), 3.68 (1H, m), 3.45 (2H, m), 3.13 (1H, m), 2.80 (2H, m), 1.91 (3H, s).

Example 116
2-[2-[N-(4-Chlorophenyl)-N-ethyl]aminoethyl]amino-3-[N-(2-aminoethyl)-N-(4-chlorobenzenesulfonyl)]aminopyridine $^1$H-NMR(270 MHz, CDCl$_3$) δ: 8.11 (1H, dd, J=4.62, 1.65 Hz), 7.65 (2H, d, J=8.74 Hz), 7.46 (2H, d, J=8.74 Hz), 7.13 (2H, d, J=8.91 Hz), 6.74 (2H, d, J=8.91 Hz), 6.62 (1H, dd, J=7.58, 1.65 Hz), 6.42 (1H, dd, J=7.58, 4.62 Hz), 6.25 (1H, m), 3.89 (1H, m), 3.58 (2H, m), 3.41 (2H, q), 3.08 (1H, m), 2.77 (1H, m), 2.59 (1H, m), 1.14 (3H, t).

Example 117
3-[N-(2-Aminoethyl)-N-(4-methoxybenzenesulfonyl)]amino-2-[2-(4-chlorophenyl)aminoethyl]aminopyridine $^1$H-NMR(270 MHz, CDCl$_3$) δ: 8.03~8.05 (1H, m), 7.62 (2H, d, J=8.91 Hz), 7.06 (2H, d, J=8.57 Hz), 6.93 (2H, d, J=8.90 Hz), 6.56 (2H, d, J=8.58 Hz), 6.42~6.53 (1H, br), 6.36~6.41 (1H, m), 3.88~3.99 (1H, m), 3.83 (3H, s), 3.57~3.76 (1H, m), 3.25~3.38 (2H, m), 2.99~3.07 (1H, m), 2.74~2.79 (1H, m), 2.55~2.65 (1H, m).

Example 118
3-[N-(2-Aminoethyl)-N-(p-toluenlesulfonyl)]amino-2-[2-(4-chlorophenyl)aminoethyl]aminopyridine $^1$H-NMR(270 MHz, CDCl$_3$) δ: 8.03~8.06 (1H, m), 7.56 (2H, d, J=8.25 Hz), 7.28 (2H, d, J=6.6 Hz), 7.07 (2H, d, J=6.6 Hz), 6.57 (2H, d, J=8.91 Hz), 6.41~6.50 (1H, br), 6.35~6.40 (1H, m), 3.92~4.08 (1H, m), 3.70~3.88 (1H, m), 3.45~3.67 (1H, m), 3.26~3.41 (2H, m), 3.01~3.09 (1H, m), 2.76~2.82 (1H, m), 2.63~2.68 (1H, m), 2.43 (3H, s).

Example 119
3-[N-(4-Acetylaminobenzenesulfonyl)-N-(2-aminoethyl)]amino- 2-[2-(4-chlorophenyl)aminoethyl]aminopyridine $^1$H-NMR(270 MHz, CDCl$_3$) δ: 8.04 (2H, dd, J=4.95, 1.65 Hz), 7.63 (2H, d, J=8.91 Hz), 7.58 (2H, d, J=8.91 Hz), 7.06 (2H, d, J=8.90 Hz), 6.60 (1H, dd, J=7.59, 1.65 Hz), 6.54 (2H, d, J=8.58 Hz), 6.38 (1H, dd, J=7.59, 4.95 Hz), 3.88~4.03 (1H, m), 3.70~3.85 (1H, m), 3.44~3.62 (1H, m), 3.16~3.38 (2H, m), 3.00~3.12 (1H, m), 2.75 2.89 (1H, m), 2.56~2.68 (1H, m), 2.18 (3H, s).

Example 120
3-[N-(2-Aminoethyl)-N-(4-nitrobenzenesulfonyl)]amino-2-[2-(4-chlorophenyl)aminoethyl]aminopyridine $^1$H-NMR(270 MHz, CDCl$_3$) δ: 8.24 (2H, d, J=8.58 Hz), 8.01 (1H, dd, J=4.62, 1.65 Hz), 7.80 (2H, d, J=8.91 Hz), 7.00 (2H, d, J=8.58 Hz), 6.71~6.82 (1H, m), 6.48 (2H, d, J=8.90 Hz), 6.46~6.52 (1H, m), 6.29~6.37 (1H, m), 3.90~4.04 (1H, m), 3.64~3.79 (1H, m), 3.453.59 (1H, m), 3.16~3.38 (2H, m), 3.01~3.14 (1H, m), 2.76~2.85 (1H, m), 2.52~2.66 (1H, m).

Example 121
2-[2-[N-(4-Chlorophenyl)-N-hydroxyoxalyl]aminoethyl]amino-3-(4-chlorobenzenesulfonyl)aminopyridine $^1$H-NMR(270 MHz, DMSO-d$_6$) δ: 7.80 (1H, dd, J=4.9, 1.6 Hz), 7.71 (2H, dm, J=8.6 Hz), 7.64 (2H, dm, J=8.6 Hz), 7.39 (2H, dm, J=8.6 Hz), 7.39 (2H, dm, J=8.6 Hz), 6.97 (1H, dd, J=7.5, 1.6 Hz), 6.47 (1H, dd, J=7.5, 4.9 Hz), 6.41 (1H, br), 3.78 (2H, brt, J=6.5 Hz), 3.38 (2H, brdt, J=6.5, 5 Hz).

Example 122
1-[2-(4-Chlorophenyl)aminoethoxy]-2-[N-(2-aminoethyl)-N-(4-chlorobenzenesulfonyl)]aminobenzene $^1$H-NMR(270 MHz, CDCl$_3$) δ: 7.66 (2H, d, J=8.58 Hz), 7.45 (2H, d, J=8.58 Hz), 7.31 (1H, m), 7.12 (2H, d, J=8.91 Hz), 6.95 (1H, m), 6.89 (1H, m), 6.76 (1H, m), 6.62 (2H, d, J=8.91 Hz), 4.19 (2H, m), 3.42 (4H, m), 2.64 (2H, m).

Example 123
1-[2-(4-Chlorophenyl)aminoethoxy]-2-[N-[2-(2-aminoethoxy)ethyl]-N-(4-chlorobenzenesulfonyl)]aminobenzene $^1$H-NMR(270 MHz, CDCl$_3$) δ: 7.70 (2H, d, J=8.58 Hz), 7.42 (2H, d, J=8.58 Hz), 7.34~7.28 (1H, m), 7.12 (2H, d, J=8.91 Hz), 7.00~6.88 (2H, m), 6.58 (2H, d, J=8.91 Hz), 4.13 (2H, m), 3.73 (2H, m), 3.47 (2H, m), 3.34 (4H, m), 2.71 (2H, m).

Referential Example 9
3-Nitro-4-(4-morpholino)-1-(4-morpholinocarbonyl)benzene To a solution of 4-fluoro-3-nitrobenzoic acid (2.14 g) in tetrahydrofuran, carbonyldiimidazole (2.06 g) was added, followed by stirring at room temperature for 2 hours. When bubbling of carbon dioxide gas stopped, morpholin (2.22 g) was added thereto, followed by stirring at room temperature for 2 hours. The resultant solution was diluted with acetic acid, and the thus-obtained solution was washed with 2N HCl, saturated aqueous sodium bicarbonate solution, and saturated brine in a sequential manner. The organic layer was dehydrated over anhydrous magnesium sulfate, and the solvent was evaporated under reduced pressure. The residue was purified by means of column chromatography (solvent: hexane/acetic acid=1/1) to yield the target product (2.66 g) as orange-colored crystals.

$^1$H-NMR(270 MHz, CDCl$_3$) δ: 7.89 (1H, d, J=1.98 Hz), 7.58 (1H, dd, J=8.58, 1.98 Hz), 7.13 (1H, d, J=8.58 Hz), 3.85 (4H, t, J=4.70 Hz), 3.70 (4H, brs), 3.65 (4H, brs), 3.11 (4H, t, J=4.70 Hz).

Example 124
3-[N-(4-Chlorobenzenesulfonyl)]amino-4-(4-morpholino)-1-(4-morpholinocarbonyl)benzene The product of Referential Example 9 (1.0 g) was dissolved in a mixture of ethanol and acetic acid (30 ml). To the thus-obtained solution, 5% palladium on carbon (0.2 g) was added, and the resultant mixture was stirred at room temperature under hydrogen atmosphere until the starting compound was completely consumed. Subsequently, the catalyst was filtered off, and the solvent of the filtrate was evaporated under reduced pressure. The residue was dissolved in acetic acid, and the resultant solution was washed with saturated brine. The organic layer was dehydrated over potassium carbonate, and the solvent was evaporated to thereby obtain an aniline compound (0.90 g). The aniline compound was dissolved in pyridine (5 ml), and 4-chlorobenzenesulfonylchloride (722 mg) was added thereto, followed by stirring at room temperature for 1 hour under ice cooling. Subsequently, an excess pyridine was evaporated, and the residue was diluted with acetic acid. The resultant solution was washed with 2N HCl, saturated aqueous sodium bicarbonate solution, and saturated brine in a sequential manner, and the organic layer was dehydrated over anhydrous magnesium sulfate. The solvent was evaporated under reduced pressure, and the residue was purified by means of column chromatography (solvent: hexane/acetic acid=1/1) to yield the target product (1.44 g) as white crystals.

$^1$H-NMR(270 MHz, CDCl$_3$) δ: 7.95 (1H, brs), 7.77 (2H, d, J=8.58 Hz), 7.56 (1H, s), 7.43 (2H, d, J=8.58 Hz), 7.17 (2H, m), 3.95~3.30 (12H, m), 2.63 (4H, m).

Example 125
3-[N-[2-(2-t-Butoxycarbonylaminoethoxy)ethyl]-N-(4-chlorobenzenesulfonyl)]amino-4-(4-morpholino)-1(4-morpholinocarbonyl)benzene The product of Referential Example 124 (800 mg), N-t-butoxycarbonylaminoethanol (423 mg), and triphenylphosphine (540 mg) were dissolved in tetrahydrofuran (15 ml). To the resultant solution, diisopropylazocarboxylate (417 mg) was added dropwise under ice cooling, followed by stirring at room temperature for 1 hour. The solvent was evaporated under reduced pressure, and the residue was purified by means of column chromatography (solvent: hexane/acetic acid=1/1) to yield the target product (1.16 g) as pale-brown oily matter.

$^1$H-NMR(270 MHz, CDCl$_3$) δ: 7.83 (2H, d, J=8.90 Hz), 7.52 (2H, d, J=8.90 Hz), 7.37 (1H, dd, J=8.24, 1.98 Hz), 7.14 (1H, d, J=1.98 Hz), 7.12 (1H, d, J=8.24 Hz), 4.81 (1H, brs), 4.06~2.80 (24H, m), 1.44 (9H, s).

Example 126
3-[N-[2-(2-Aminoethoxy)ethyl-N-(4-chlorobenzenesulfonyl)]amino-4-(4-morpholino)-1(4-morpholinocarboxyl)benzene t-Butoxycarbonyl compound (398 mg) was dissolved in ethyl acetate (5 ml). The resultant solution was stirred on ice, during which 4N HCl-ethyl acetate solution (2 ml) was added thereto. The mixture was stirred overnight at room temperature. The reaction mixture was made alkaline with an aqueous saturated sodium hydrogencarbonate solution and extracted with ethyl acetate. The organic layer was washed with saturated brine, dried over anhydrous sodium sulfate, and the solvent was removed under reduced pressure. The resultant residue was crystallized from hexane, to thereby yield the target compound (254 mg).

$^1$H-NMR(270 MHz, CDCl$_3$) δ: 7.84 (2H, d, J=8.57 Hz), 7.52 (2H, d, J=8.57 Hz), 7.38 (1H, dd, J=8.24, 1.98 Hz), 7.14 (1H, d, J=1.98 Hz), 7.12 (1H, d, J=8.24 Hz), 4.06~2.40 (26H, m).

In a manner similar to that described in Examples 124–126, the compounds of Examples 127–139 were obtained.

Example 127
2-(4-Morpholino)-1-[N-[2-(2-aminoethoxy)ethyl]-N-(4-chlorobenzenesulfonyl)]aminobenzene $^1$H-NMR(270 MHz, CDCl$_3$) δ: 7.85 (2H, d, J=8.57 Hz), 7.49 (2H, d, J=8.57 Hz), 7.31 (1H, m), 7.15 (1H, d, J=7.25 Hz), 6.98 (2H, m), 4.01 (2H, m), 3.81 (4H, m), 3.55~2.35 (12H, m).

Example 128
2-(4-Morpholino)-1-[N-[2-(dimethylamino)ethyl]-N-(4-chlorobenzenesulfonyl)]aminobenzene Hydrochloride Salt $^1$H-NMR(270 MHz, DMSO-d$_6$) δ: 10.26 (1H, brs), 7.32 (2H, d, J=8.58 Hz), 7.28~7.32 (1H, m), 7.22 (1H, t, J=8.25 Hz), 6.94 (2H, d, J=8.58 Hz), 6.82 (1H, d, J=8.56 Hz), 6.67 (1H, t, J=7.58 Hz), 4.16~4.22 (1H, m), 4.02~4.24 (8H, br), 2.86~2.91 (2H, m), 2.82 (6H, d, J=3.84 Hz).

Example 129
2-(1-Piperazino)-1-[N-[2-(dimethylamino)ethyl]-N-(4-chlorobenzenesulfonyl)]aminobenzene Hydrochloride Salt $^1$H-NMR(270 MHz, DMSO-d$_6$) δ: 10.26 (1H, brs), 7.31 (2H, d, J=8.58 Hz), 7.28~7.32 (1H, m), 7.22 (1H, t, J=8.24

Hz), 6.94 (2H, d, J=8.58 Hz), 6.84 (1H, d, J=8.54 Hz), 6.67 (1H, t, J=7.58 Hz), 4.16~4.22 (1H, m), 3.04~3.22 (8H, m), 2.88~2.93 (2H, m), 2.76 (6H, d, J=3.96 Hz).

Example 130

2-[4-(4-Chlorophenyl)-1-piperazino]-1-[N-(2-aminoethyl)-N-(4-chlorobenzenesulfonyl)]aminobenzene $^1$H-NMR(270 MHz, CDCl$_3$) δ: 7.79 (2H, d, J=8.58 Hz), 7.51 (2H, d, J=8.58 Hz), 7.40~7.15 (4H, m), 7.06 (1H, m), 6.91~6.82 (3H, m), 3.96~2.44 (12H, m).

Example 131

2-[4-(4-Chlorophenyl)-1-piperazino]-1-[N-[2-(2-aminoethoxy)ethyl]-N-(4-chlorobenzenesulfonyl)]aminobenzene $^1$H-NMR(270 MHz, CDCl$_3$) δ: 7.87 (2H, d, J=8.58 Hz), 7.50 (2H, d, J=8.58 Hz), 7.36~7.18 (4H, m), 7.06~6.95 (2H, m), 6.88 (2H, d, J=8.91 Hz), 4.01 (2H, m), 3.55~2.46 (14H, m).

Example 132

2-[4-(4-Chlorophenyl)-1-piperazino]-1-[N-[2-(dimethylamino)ethyl]-N-(4-chlorobenzenesulfonyl)]aminobenzene $^1$H-NMR(270 MHz, CDCl$_3$) δ: 7.85 (2H, d, J=8.58 Hz), 7.49 (2H, d, J=8.58 Hz), 7.33~7.18 (2H, m), 7.23 (2H, d, J=8.91 Hz), 7.03~6.94 (2H, m), 6.88 (2H, d, J=8.91 Hz), 3.86~3.64 (2H, m), 3.86~3.64 (6H, m), 2.98 (2H, m), 2.22 (2H, t), 2.08 (6H, s).

Example 133

2-[4-(4-Chlorophenyl)-1-homopiperazino]-1-[N-(4-chlorobenzenesulfonyl)]aminobenzene $^1$H-NMR(270 MHz, CDCl$_3$) δ: 7.93 (1H, brs), 7.69 (2H, d, J=8.57 Hz), 7.53 (1H, d, J=7.92 Hz), 7.42 (2H, d, J=8.57 Hz), 7.19 (2H, d, J=9.24 Hz), 7.17~6.96 (3H, m), 6.63 (2H, d, J=9.24 Hz), 3.59 (4H, m), 2.88 (2H, m), 2.74 (2H, m), 1.98 (2H, m).

Example 134

2-[4-(4-Chlorophenyl)-1-homopiperazino]-1-[N-[2-(2-aminoethoxy)ethyl]-N-(4-chlorobenzenesulfonyl)]aminobenzene $^1$H-NMR(270 MHz, CDCl$_3$) δ: 7.81 (2H, d, J=8.58 Hz), 7.46 (2H, d, J=8.58 Hz), 7.27~7.07 (4H, m), 6.93~6.82 (2H, m), 6.63 (2H, d, J=9.23 Hz), 3.96~2.45 (18H, m), 2.20~1.80 (2H, m).

Example 135

2-[4-(4-Chlorophenyl)-1-homopiperazino]-1-[N-[2-(dimethylamino)ethyl]-N-(4-chlorobenzenesulfonyl)]aminobenzene.HCl $^1$H-NMR(270 MHz, DMSO-d$_6$) δ: 7.91 (2H, d, J=8.58 Hz), 7.75 (2H, d, J=8.58 Hz), 7.20~7.26 (1H, m), 7.18 (2H, d, J=9.24 Hz), 7.00 (1H, t, J=7.26 Hz), 6.74~6.83 (4H, m), 4.04~4.10 (1H, m), 3.62~3.68 (2H, m), 3.06 3.60 (10H, m).

Example 136

2-[4-(4-Chlorophenyl)-1-piperazino]-3-[N-(2-aminoethyl)-N-(4-chlorobenzenesulfonyl)]aminopyridine $^1$H-NMR(270 MHz, CDCl$_3$) δ: 8.25 (1H, dd, J=4.62, 1.82 Hz), 7.76 (2H, d, J=8.41 Hz), 7.53 (2H, d, J=8.41 Hz), 7.22 (2H, d, J=8.91 Hz), 7.12 (1H, dd, J=7.92, 1.82 Hz), 6.87 (2H, d, J=8.91 Hz), 6.79 (1H, dd, J=7.92, 4.62 Hz), 4.00~3.34 (6H, m), 3.24 (4H, m), 2.70 (2H, m).

Example 137

2-[4-(4-Chlorophenyl)-1-piperazino]-3-[N-[2-(2-aminoethoxy)ethyl]-N-(4-chlorobenzenesulfonyl)]aminopyridine $^1$H-NMR(270 MHz, CDCl$_3$) δ: 8.22 (1H, dd, J=4.95, 1.98 Hz), 7.77 (2H, d, J=8.58 Hz), 7.51 (2H, d, J=8.58 Hz), 7.22 (2H, d, J=9.23 Hz), 7.12 (1H, dd, J=7.59, 1.98 Hz), 6.88 (2H, d, J=9.23), 6.75 (1H, dd, J=7.59, 4.95 Hz), 4.06~3.08 (14H, m), 2.66 (2H, m).

Example 138

2-[4-(4-Chlorophenyl)-1-piperazino]-3-[N-(2-dimethylaminoethyl)-N-(4-chlorobenzenesulfonyl)]aminopyridine $^1$H-NMR(270 MHz, CDCl$_3$) δ: 8.21 (1H, dd, J=4.62, 1.77 Hz), 7.75 (2H, d, J=8.58 Hz), 7.50 (2H, d, J=8.58 Hz), 7.22 (2H, d, J=8.90 Hz), 7.05 (1H, dd, J=7.71, 1.77 Hz), 6.87 (2H, d, J=8.90), 6.72 (1H, dd, J=7.71, 4.62 Hz), 3.98~3.45 (6H, m), 3.22 (4H, m), 2.24 (2H, m), 2.11 (6H, s).

Referential Example 10

8-t-Butoxycarbonylamino-1,2,3,4-tetrahydroquinoline

8-Aminoquinoline (50 g) and palladium-carbon (5 g) were added to ethanol (100 ml) and the resultant mixture was subjected to catalytic reduction under hydrogen atmosphere (4 kgf/cm$^2$). After consumption of all low materials having been confirmed, the catalyst was removed and the solvent was removed under reduced pressure. The thus-obtained reduced compound was dissolved in chloroform (300 ml), and the resultant solution was stirred on ice, during which a chloroform solution containing di-t-buthyldicarbonate (83 g) was added dropwise thereto. After completion of addition, the mixture was stirred at room temperature. After consumption of all low materials having been confirmed, the solvent was removed. The residue was purified by means of silica gel column chromatography (elution solvent=hexane:ethyl acetate=4:1), to thereby yield the target compound (60 g) as colorless crystals.

$^1$H-NMR(270 MHz, CDCl$_3$) δ: 7.26 (1H, d, J=1.32 Hz), 6.82 (1H, d, J=7.59 Hz), 6.66 (1H, t, J=7.59 Hz), 6.02 (1H, brs), 3.32 (2H, t, J=5.45 Hz), 2.78 (2H, t, J=6.27 Hz), 1.90 (2H, m), 1.50 (9H, s).

Referential Example 11

8-t-Butoxycarbonylamino-1-(4-chlorophenoxyacetyl)-1,2,3,4-tetrahydroquinoline

The product of the Referential Example (5 g) was dissolved in pyridine (100 ml). The resultant solution was stirred on ice, during which 4-chlorophenoxyacetylchloride (5 g) was added thereto. The mixture was further stirred at room temperature. After consumption of all low materials having been confirmed, the solvent was removed under reduced pressure and the resultant residue was subjected to extraction with ethyl acetate. The organic layer was washed with saturated brine and dried over anhydrous magnesium sulfate. Subsequently, the solvent was removed under reduced pressure. The residue was purified by means of NH silica gel column chromatography (elution solvent= hexane:ethyl acetate=5:1), to thereby yield the target compound (7 g) as colorless crystals.

$^1$H-NMR(270 MHz, CDCl$_3$) δ: 7.91 (1H, d, J=8.25 Hz), 7.60 (1H, d, J=7.92 Hz), 7.30~6.63 (6H, m), 4.92~4.73 (2H, m), 4.62 (1H, d, J=14.84 Hz), 4.35 (1H, d, J=14.84 Hz), 2.95~2.63 (2H, m), 2.48~2.21 (2H, m), 1.50 (9H, s).

Referential Example 12
8-t-Butoxycarbonylamino-1-[2-(4-chlorophenoxy)ethyl]-1,2,3,4-tetrahydroquinoline The product of Referential Example 11 (20 g) was dissolved in tetrahydrofuran (200 ml) and the resultant solution was stirred on ice, during which dimethylsulfideborane (27 ml) was added dropwise thereto. After completion of addition, the mixture was stirred at room temperature. After consumption of all materials having been confirmed, the mixture was stirred on ice and excessive volumes of acetone and methanol were added to thereto, followed by stirring at room temperature. Subsequently, the solvent was removed under reduced pressure and the resultant residue was extracted with ethyl acetate. The organic layer was washed with saturated brine and dried over anhydrous magnesium sulfate. The solvent was removed under reduced pressure. The residue was purified by means of silica gel column chromatography (elution solvent=hexane:ethyl acetate=15:1), to thereby yield the target compound (16 g) as colorless crystals.

$^1$H-NMR(270 MHz, CDCl$_3$) δ: 7.94 (1H, d, J=7.92 Hz), 7.86 (1H, s), 7.25 (2H, d, J=8.58 Hz), 7.02~6.93 (3H, m), 6.73 (1H, d, J=6.93 Hz), 4.10 (2H, t, J=5.12 Hz), 3.16 (2H, t, J=5.12 Hz), 3.10~3.02 (2H, m), 2.80 (2H, t, J=6.76 Hz), 1.89~1.80 (2H, m), 1.48 (9H, s).

Example 139
8-(4-Chlorobenzenesulfonyl)amino-1-[2-(4-chlorophenoxy)ethyl]-1,2,3,4-tetrahydroquinoline The product of Referential Example 12 (31 g) was dissolved in ethyl acetate (500 ml) and the resultant solution was stirred on ice, during which a 4N hydrochloride-ethyl acetate solution was added dropwise thereto. The mixture was stirred moderately at room temperature and allowed to stand for 15 hours. The mixture was stirred on ice again and a 2N aqueous sodium hydroxide solution was added to make the mixture alkaline. Subsequently, the mixture was extracted with ethyl acetate. The organic layer was washed with saturated brine and dried over anhydrous magnesium sulfate. The solvent was removed under reduced pressure and the thus-obtained amino compound was dissolved in pyridine (400 ml). The resultant solution was stirred on ice, during which 4-chlorobenzenesulfonyl chloride (20 mg) was added thereto. The mixture was stirred at 50° C. and after consumption of all low materials having been confirmed, the solvent was removed under reduced pressures. The resultant residue was extracted with chloroform. The organic layer was washed with saturated brine and dried over anhydrous magnesium sulfate. The solvent was removed under reduced pressure. The residue was purified by means of NH silica gel column chromatography (elution solvent=hexane:ethyl acetate=2:1), to thereby yield the target compound.

$^1$H-NMR(270 MHz, CDCl$_3$) δ: 8.47 (1H, s), 7.72 (2H, d, J=8.58 Hz), 7.54 (1H, d, J=7.91 Hz), 7.39~7.17 (6H, m), 6.93 (1H, t, J=7.92 Hz), 6.76 (1H, d, J=6.92 Hz), 4.00 (2H, t, J=4.62 Hz), 4.18 (1H, s), 2.92~2.88 (2H, m), 2.82 (2H, t, J=4.78 Hz), 2.73 (2H, t, J=6.77 Hz), 1.81~1.73 (2H, m).

Example 140
8-[N-[2-(2-Aminoethoxy)ethyl]-N-(4-chlorobenzenesulfonyl)]amino-1-[2-(4-chlorophenoxy)ethyl]-1,2,3,4-tetrahydroquinone The product of Example 139 (400 mg), N-t-butoxycarbonylaminoethoxy ethanol (210 mg), and triphenylphosphine (270 mg) were dissolved in tetrahydrofuran (10 ml) and the resultant solution was stirred on ice, during which diisopropylazocarboxylate (210 mg) was added dropwise thereto. Subsequently, the mixture was stirred at room temperature for one hour. The solvent was removed under reduced pressure. The residue was purified by means of silica gel chromatography. A portion (400 mg) of the thus-obtained oily product was dissolved in ethyl acetate (5 ml) and the resultant solution was stirred on ice, during which a 4N hydrochloride-ethyl acetate solution (2 ml) was added dropwise thereto. The mixture was stirred overnight at room temperature. The thus-obtained reaction mixture was made alkaline by using an aqueous saturated sodium hydrocarbonate solution and subjected to extraction with ethyl acetate. The organic layer was washed with saturated brine and dried over anhydrous magnesium sulfate. The solvent was removed under reduced pressure. The residue was crystallized from hexane, to thereby produce the target compound (282 mg).

$^1$H-NMR(270 MHz, CDCl$_3$) δ: 7.83 (2H, d, J=8.57 Hz), 7.47 (2H, d, J=8.58 Hz), 7.24 (2H, d, J=8.90 Hz), 6.95~6.99 (1H, m), 6.89 (2H, d, J=8.91 Hz), 6.72 (1H, t, J=7.59 Hz), 6.62~6.65 (1H, m), 4.17~4.32 (1H, m), 3.85~4.00 (1H, m), 3.72~3.84 (1H, m), 3.493.60 (1H, m), 3.27~3.47 (2H, m), 3.26~3.85 (2H, m), 3.40~3.80 (1H, m), 2.71~2.85 (1H, m), 2.50~2.70 (1H, m), 1.87~2.20 (1H, m), 1.76~1.82 (1H, m), 1.10~1.38 (4H, m), 0.84~0.92 (1H, m).

Referential Example 13
2-(4-Chlorophenylthio)nitrobenzene

2-Fluoronitrobenzene (1.5 g) and 4-chlorothio phenol (1.5 g) were dissolved in ethanol (30 ml) and potassium carbonate (1.4 g) was added thereto, followed by stirring at 60° C. for five hours. Subsequently, the solvent was removed under reduced pressure and the residue was dissolved in water (50 ml). The resultant solution was subjected to extraction with ethyl acetate (30 ml×2). The organic layer was washed sequentially with water and saturated brine and dried over anhydrous sodium sulfate. The solvent was removed under reduced pressure. The residue was re-crystallized from diethyl ether, to thereby produce the target compound (2.1 g) as pale-brown crystals.

$^1$H-NMR(270 MHz, CDCl$_3$) δ: 8.22 (1H, d, J=8.25 Hz), 7.52 (2H, d, J=8.91 Hz), 7.45 (2H, d, J=8.91 Hz), 7.37 (1H, t, J=7.92 Hz), 7.20~7.27 (1H, m), 6.86 (1H, d, J=7.92 Hz).

Referential Example 14
2-(4-Chlorophenylthio)aniline 2-(4-Chlorophenylthio)nitrobenzene (1.0 g) was dissolved in a mixture of acetic acid (5 ml) and 6N hydrochloride (5 ml), and tin (1.0 g) was added thereto, followed by stirring for six hours at room temperature. After the solvent was removed under reduced pressure, the residue was dissolved in water (50 ml) and a pH of the resultant solution was adjusted to 9–10 with potassium carbonate. The thus-obtained solution was extracted with ethyl acetate. The extracted solution was washed sequentially with water and saturated brine and dried over anhydrous sodium sulfate. Subsequently, the solvent was removed under reduced pressure and the residue was crystallized from ethyl acetate under stirring, to thereby yield the target compound (880 mg) as pale-yellow crystals.

$^1$H-NMR(270 MHz, CDCl$_3$) δ: 7.41 (1H, dd, J=7.59, 1.32 Hz), 7.23 (1H, t, J=5.94 Hz), 7.16 (2H, d, J=8.58 Hz), 6.99 (2H, d, J=8.58 Hz), 6.71~6.78 (2H, m), 4.26 (2H, brs).

Example 141
N-(4-Chlorobenzenesulfonyl)-2-(4-chlorophenylthio)aniline

The product of Referential Example 14 (800 mg) was dissolved in pyridine (5 ml) and the resultant solution was stirred on ice, during which 4-chlorobenzene sulfonyl chloride (742 mg) was added thereto, followed by stirring for three hours at room temperature. Ethyl acetate (50 ml) was added to the reaction mixture. The mixture was washed sequentially with water and saturated brine and dried over anhydrous sodium sulfate. Subsequently, the solvent was removed under reduced pressure and the residue was purified by means of silica gel column chromatography (elution solvent=chloroform:ethanol=100:5), to thereby yield the target compound (1.2 g) as colorless crystals.

$^1$H-NMR(270 MHz, CDCl$_3$) δ: 7.95 (1H, d, J=8.91 Hz), 7.54 (2H, d, J=8.57 Hz), 7.38~7.46 (2H, m), 7.27 (2H, d, J=8.58 Hz), 7.11 (2H, d, J=8.58 Hz), 6.74 (2H, d, J=8.91 Hz).

Example 142

2-(4-Chlorophenylthio)-N-(4-chlorobenzenesulfonyl)-N-(2-dimethylaminoethyl)aniline.HCl The product of Example 141 (1 g) was dissolved in anhydrous tetrahydrofuran (5 ml) and triphenylphosphine (0.96 g), and N,N-dimethylamino ethanol (0.32 g) were added thereto, followed by stirring for five minutes on ice. To the resultant solution was gradually added dropwise diisopropylazodicarboxylate (0.74 g). After completion of addition, the mixture was stirred overnight at room temperature. Subsequently, the solvent was removed under reduced pressure and the residue was purified by means of silica gel column chromatography (elution solvent=ethyl acetate:hexane=1:3), to thereby yield the target compound (0.38 g) as pale-yellow oily products. The oily product (0.35 g) was dissolved in ethyl acetate (8 ml) and stirred at room temperature, during which a 4N hydrochloride—ethyl acetate solution (0.2 ml) was added thereto, followed by stirring at room temperature for 3 hours. The precipitated crystals were collected by filtration, washed with n-hexane, and dried under reduced pressure at 40° C. for six hours, to thereby yield the target compound (0.32 g) as colorless powder.

$^1$H-NMR(270 MHz, DMSO-d$_6$) δ: 10.32 (1H, brs), 7.72 (2H, d, J=8.58 Hz), 7.62 (2H, d, J=8.58 Hz), 7.42 (2H, d, J=8.58 Hz), 7.34~7.41 (1H, m), 7.14 (1H, t, J=7.56 Hz), 7.06 (2H, d, J=8.56 Hz), 6.82 (1H, d, J=7.58 Hz), 6.76 (1H, d, J=8.21 Hz), 4.02 (2H, brz), 3.21 (2H, d, J=6.6 Hz), 2.76 (6H, s).

Referential Example 15

2-(4-Chlorophenoxy)nitrobenzene

2-Fluoronitrobenzene (1.5 g) and 4-chlorophenol (1.3 g) were dissolved in dimethylformamide (20 ml) and potassium carbonate (1.4 g) was added thereto. The mixture was stirred overnight at 80° C. After the mixture was cooled, water (100 ml) was added thereto and the mixture was extracted with ethyl acetate (50 ml×2). The mixture was washed with water and saturated brine and dried over anhydrous sodium sulfate. The solvent was removed under reduced pressure and the residue was re-crystallized from methanol, to thereby yield the target compound (2.2 g) as pale-yellow crystals.

$^1$H-NMR(270 MHz, CDCl$_3$) δ: 8.22 (1H, d, J=8.22 Hz), 7.42 (2H, d, J=8.94 Hz), 7.36 (1H, t, J=7.92 Hz), 7.20~7.24 (1H, m), 7.22 (2H, d, J=8.94 Hz), 6.84 (1H, d, J=7.92 Hz).

Referential Example 16

2-(4-Chlorophenylamino)nitrobenzene

2-Fluoronitrobenzene (3.0 g) and 4-chloroaniline (2.5 g) were dissolved in pyridine (30 ml) and stirred at 80° C. for 18 hours. The resultant solution was allowed to cool, and thereafter, water (100 ml) was added thereto and the mixture was extracted with ethyl acetate (50 ml×3). The organic layer was washed with water and saturated brine and dried over anhydrous sodium sulfate. The solvent was removed under reduced pressure and the residue was re-crystallized from ethyl acetate-hexane, to thereby yield the target compound (2.5 g) as pale-brown crystals.

$^1$H-NMR(270 MHz, CDCl$_3$) δ: 9.40 (1H, brs), 8.20 (1H, dd, J=8.58 Hz), 7.37 (2H, d, J=8.90 Hz), 7.35~7.39 (2H, m), 7.21 (2H, d, J=8.90 Hz), 7.15~7.19 (2H, m), 6.80 (1H, t, J=7.26 Hz).

According to the methods described in Referential Example 14 and Examples 141 and 142, the compounds of Examples 143–146 were obtained.

Example 143

1-N-[2-(2-Aminoethoxy)ethyl]-N-(4-chlorobenzenesulfonyl)-2-(4-chlorophenylthio)aniline $^1$H-NMR(270 MHz, CDCl$_3$) δ: 7.71 (2H, d, J=8.91 Hz), 7.43 (2H, d, J=8.58 Hz), 7.31 (2H, d, J=8.58 Hz), 7.25 (2H, d, J=8.58 Hz), 7.11~7.18 (2H, m), 7.05~7.93 (1H, m), 6.93 (1H, d, J=7.58 Hz), 3.80~3.90 (2H, m), 3.53~3.65 (2H, m), 3.33~3.43 (2H, m), 2.72~2.75 (2H, m).

Example 144

1-[N-[2-(2-Aminoethoxy)ethyl]-N-(4-chlorobenzenesulfonyl)]-2-(4-chlorophenoxy)aniline $^1$H-NMR(270 MHz, CDCl$_3$) δ: 8.11 (1H, s), 7.70 (2H, d, J=8.58 Hz), 7.57 (2H, d, J=8.58 Hz), 7.40 (2H, d, J=8.91 Hz), 7.30~7.36 (1H, m), 7.13~7.19 (1H, m), 6.79 (2H, d, J=8.91 Hz), 6.80 (1H, t, J=4.29 Hz), 3.47~3.80 (4H, m), 2.86 (2H, t, J=5.28 Hz).

Example 145

1-[N-[2-(Dimethylamino)ethyl]-N-(4-chlorobenzenesulfonyl)]-2-(4-chlorophenoxy)aniline.HCl $^1$H-NMR(270 MHz, DMSO-d$_6$) δ: 10.35 (1H, br), 7.73 (2H, d, J=8.58 Hz), 7.60 (2H, d, J=8.58 Hz), 7.41 (2H, d, J=8.58 Hz), 7.34~7.42 (1H, m), 7.17 (1H, t, J=7.59 Hz), 6.84 (1H, d, J=8.58 Hz), 6.76 (1H, d, J=8.24 Hz), 4.03 (2H, br), 3.21 (2H, t, J=6.6 Hz), 2.79 (6H, s).

Example 146

N-[2-(2-Aminoethoxy)ethyl]-N-(4-chlorobenzenesulfonyl)-N'-(4-chlorophenyl)-o-phenylenediamine $^1$H-NMR(270 MHz, CDCl$_3$) δ: 7.63 (2H, d, J=8.58 Hz), 7.39 (2H, d, J=8.57 Hz), 7.13~7.20 (4H, m), 7.00 (2H, d, J=8.91 Hz), 6.76 (1H, s), 6.68 (1H, t, J=7.92 Hz), 4.26 (1H, br), 3.51~3.68 (2H, m), 3.28~3.41 (4H, m), 3.15~3.33 (2H, m).

Example 147

N-(4-Chlorobenzenesulfonyl)-N-(2-dimethylaminoethyl)-N'-[2-(4-chlorobenzyloxy)ethyl]-o-phenylenediamine $^1$H-NMR(270 MHz, CDCl$_3$) δ: 7.66 (2H, d, J=8.58 Hz), 7.24 (2H, d, J=8.57 Hz), 7.16 (1H, t, J=5.61 Hz), 6.85~6.91 (4H, m), 6.72 (1H, d, J=8.25 Hz), 6.45~6.49 (2H, m), 5.77 (1H, t, J=5.94 Hz), 4.72 (2H, s), 4.04~4.11 (3H, m), 3.48~3.56 (2H, m), 3.00~3.08 (1H, m), 2.36~2.40 (1H, m), 2.15 (6H, s).

Example 148

(1) N-(4-Chlorobenzenesulfonyl)-o-phenylenediamine

In a 1-L three-neck flask, o-phenylenediamine (56.13 g) was added to pyridine (350 ml) and the resultant solution was stirred with a stirrer bar to dissolve the compound. The solution was cooled in an ice-water bath, so that the temperature inside the reaction mixture became 2–3° C. 4-Chlorophenylsulfonyl chloride (73.04 g) was dissolved in pyridine (100 ml) and the resultant solution was added dropwise to the aforementioned mixture by using dropping funnel. The reaction temperature was maintained at 10° C. or lower and the dropping step required 70 minutes. The reaction mixture exhibited deep-purplish-red color. Subsequently, the mixture was stirred at 10° C. or lower for 15 minutes. The flask was removed from the ice-water bath and returned to room temperature. The mixture was further stirred for one hour. The solvent, pyridine, was removed with an aspirator under reduced pressure at 50° C. and the residue was diluted in ethyl acetate (1 L). The resultant solution was transferred to a 2-L separating funnel and water (0.5 L) and an adequate volume of a 2N hydrochloride solution were added thereto. The volume of the 2N hydrochloride solution to be added was regulated so that the pH of the washing solution became 2–3. The washing solution was extracted with ethyl acetate (0.3 L×2). The thus-obtained ethyl acetate layer was washed with saturated brine (0.3 L×3) and dried over anhydrous sodium sulfate. The solvent was removed under reduced pressure and red crystals were precipitated. Ethyl acetate (0.3 L) was added to the thus-obtained crystals to dissolve the crystals. Subsequently, the crystals were re-crystallized from the mixture of solvents (hexane:ethyl acetate=10:1). The thus-produced crystals were collected through suction-filtration, washed with the same solvent mixture, and air-dried, to thereby yield pale-yellow crystals (79.28 g). The mother liquid for re-crystallization and the washing solution were combined. Subsequently, the solvent was removed under reduced pressure. The residue was dissolved in ethyl acetate (30 ml), and the mixture of solvents (100 ml) (hexane:ethyl acetate=10:1) was added thereto, followed by re-crystallization. The thus-obtained crystals were subjected to suction-filtration, washed, and air-dried, to thereby produce pale-yellow crystals (6.41 g). Through the second re-crystallization, the target product (85.69 g) was obtained.

Mp.: 140.0° C.; $^1$H-NMR(solvent: CDCl$_3$) δ: 7.68 (2H, dt, J=9, 2 Hz), 7.43 (2H, dt, J=9, 2 Hz), 7.06 (1H, ddd, J=8, 8, 2 Hz), 6.75 (1H, dd, J=8, 1.3 Hz), 6.55 (1H, ddd, J=8.8, 1.3 Hz), 6.48 (1H, dd, J=8, 2 Hz), 6.25 (1H, brs), 4.10 (2H, br).

(2) N-(4-Chlorophenoxyacetyl)-N'-(4-chlorobenzenesulfonyl)-o-phenylenediamine

In a 2-L three-neck flask, the product of step (1) (84.71 g), pyridine (28.40 g), and dichloromethane (700 ml) were placed, and the resultant mixture was: stirred with a stirrer. The temperature inside the solution was maintained between 16–17° C. on a water bath. Subsequently, ice-cold dichloromethane (100 ml) containing 4-chlorophenoxyacetyl chloride (70.74 g) was added dropwise to the solution by using a dropping funnel while the temperature being maintained. During the dropwise addition, crystals started to precipitate. After the dropwise addition was carried out over one hour, the mixture was further stirred at the same temperature for one hour. The crystals were suction-filtered, washed with dichloromethane, and air-dried. The filtrate and the washing solution were combined and the solvent was removed under reduced pressure. To the thus-obtained crystalline residue was added methanol (500 ml) and the resultant solution was stirred and suspended. A 20% aqueous sodium hydroxide solution (60 ml) was added to the aforementioned solution so as to dissolve insoluble matter and hydrolyzed a portion of generated N-acyl compound of sulfonamide. Subsequently, an approximately half the volume of methanol was removed under reduced pressure and the resultant solution was made acidic by addition of a 2N aqueous hydrochloride solution, to thereby precipitate pale-reddish-brown crystals. After stirring for approximately three hours at room temperature, the crystals were suction-filtered and air-dried. The crystals were combined with the crystals obtained from the reaction mixture, and methanol (1 L) was added thereto. The resultant solution was refluxed for 15 minutes. The color of the crystals was changed from red to yellow and after the crystals were transferred into the solvent layer, the color disappeared into almost colorless. After being allowed to stand so that the temperature returned to room temperature, the crystals were suction-filtered and washed with methanol (200 ml×2). After air-drying, an almost colorless target product (128.50 g) was obtained.

Mp.: 188.5° C.; $^1$H-NMR(solvent: CDCl$_3$) δ: 7.81 (1H, dd, J=8, 1.5 Hz), 7.61 (2H, dt, J=9, 2 Hz), 7.38 (2H, dt, J=9, 2 Hz), 7.32 (2H, dt, J=9, 3.5 Hz), 7.30 (1H, ddd, J=8,8, 1.5 Hz), 7.07 (1H, ddd, J=88, 1.5 Hz), 6.97 (2H, dt, J=9, 3.5 Hz), 6.88 (1H, brs), 6.84 (1H, dd, J=8, 1.5 Hz), 4.57 (2H, s).

(3) N-[2-(4-Chlorophenoxy)ethyl]-N'-(4-chlorobenzenesulfonyl)-o-phenylenediamine In a 2-L three-neck flask, the product of step (2) (100.00 g) was dissolved in tetrahydrofuran (500 ml) by using a stirrer and cooled on a water bath so that the inside temperature became 2–3° C. To the resultant solution, a borane-tetrahydrofuran complex—1 M tetrahydrofuran solution (532 ml) was added by using a syringe. After stirring for one hour at 5° C., the mixture was further stirred for four hours at room temperature, to thereby obtain an almost colorless reaction mixture. The reaction mixture was cooled again on a water bath, and methanol (100 ml) was added gradually thereto by using a pipette, to dissolve the excessive borane-tetrahydrofuran complex. After completion of hydrogen gas generation, the reaction mixture was removed from the water bath and stirred for one hour during the temperature was returned to room temperature. Extremely small quantities of impurities such as fibers of filter were removed through suction-filtered and the solvent was removed under reduced pressure. To the residue was added methanol (300 ml) before drying, to thereby crystallize the residue. About one half in volume of methanol was removed under reduced pressure, to thereby yield a colorless mud-like product. The product was added to water (1 L) and the resultant solution was stirred. Crystals in the solution were suction-filtered, washed with water, and air-dried for three days, to thereby yield the target product (97.12 g). This product was submitted directly to the next reaction without further purification.

Mp.: 157.5° C.; $^1$H-NMR(solvent: CDCl$_3$) δ: 7.65 (2H, dt, J=9, 2 Hz), 7.38 (2H, dt, J=9, 2 Hz), 7.23 (2H, dt, J=9, 3.5 Hz), 7.15 (1H, ddd, J=8, 8, 4 Hz), 6.85 (2H, dt, J=9, 3.5 Hz), 6.74 (1H, brd, J=8 Hz), 6.49~6.56 (2H, m), 6.20 (1H, brs), 4.74 (1H, br), 4.07 (2H, t, J=6 Hz), 3.47 (2H, brq).

(4) N-(4-Chlorobenzenesulfonyl)-N-(2-dimethylaminoethyl)-N'-[2-(4-chlorophenoxy)ethyl]-o-phenylenediamine In a 1-L three-neck flask, the product of (3) (41.90 g), 2-dimethylaminoethylchloride hydrochloride salt (17.25 g), a stirrer, and 2-propanol (530 ml) were placed. Under stirring, sodium hydroxide (8.81 g: pellet-state) was added to the solution and the mixture was further stirred for one hour at room temperature. Because the stirring was hindered by the generation of salts, 2-propanol (530 ml) was added to the mixture and the mixture was additionally stirred for 30 minutes. Subsequently, the mixture was heated to 60° C. in an oil-bath to obtain enough temperature for the reaction, in which step 30 minutes is required to be spared. After being stirred for one hour at 60° C., the mixture was allowed to stand at room temperature for cooling. The solvent was removed under reduced pressure. To the residue was added methanol (300 ml) and after the solvent was removed under reduced pressure, methanol (100 ml) was added to the resultant residue to yield mud-like product. Water (300 ml) was added thereto and after the solvent was removed under reduced pressure, the residue was washed with methanol (100 ml) and air-dried for two days, to thereby yield the target product (47.25 g) as cream-white color powders. Methanol (470 ml) was added to the resultant crystals, and the resultant solution was refluxed to dissolve the product. The solution was allowed to stand for three hours at room temperature to re-crystallize the product. After being suction-filtered, the resultant crystals were washed with methanol (100 ml×2) and air-dried, to thereby yield the same compound as in Example 2, as almost colorless crystals (42.05 g).

Mp.: 102.3° C.; $^1$H-NMR(solvent: CDCl$_3$) δ: 7.65 (2H, d, J=8.58 Hz), 7.40 (2H, d, J=8.58 Hz), 7.24 (2H, d, J=8.91 Hz), 7.18 (1H, m), 6.87 (2H, d, J=8.91 Hz), 6.72 (1H, d, J=8.25 Hz), 6.52 (1H, dd, J=8, 6.5 Hz), 6.47 (1H, dd, J=8, 2.3 Hz), 5.78 (1H, brt), 4.02~4.14 (3H, m), 3.51 (2H, m), 3.08 (1H, m), 2.38 (1H, m), 2.17 (6H, s), 2.13 (1H, m).

(5) N-(4-Chlorobenzenesulfonyl)-N-(2-dimethylaminoethyl)-N'-[2-(4-chlorophenoxy)ethyl]-o-phenylenediamine 1-phosphate Salt Acetone was added to the product of step: (4) (40.00 g) to dissolve the compound. Under heating on an oil-bath, an acetone solution (200 ml) containing orthophopate (8.00 g) and ethanol (200 ml) were sequentially added to the resultant solution. The mixture was heated and stirred. After a while, crystals were generated. After one-hour refluxing, the mixture was removed from the oil-bath and stirred while the temperature of the mixture was returned to room temperature. The generated crystals were suction-filtered and washed with acetone (150 ml×3). The obtained crystals were air-dried and further dried by use of a vacuum pump, to thereby yield the target product (43.90 g) as colorless crystals.

Mp.: 160.3° C.; $^1$H-NMR(solvent: CDCl$_3$) δ: 7.72 (2H, dt, J=9,2 Hz), 7.63 (2H, dt, J=9,2 Hz), 7.35 (2H, dt, J=9,3.5 Hz), 7.17 (1H, ddd, J=8, 6, 3 Hz), 7.0~7.8 (3H, br), 7.00 (2H, dt, J=9, 3.5 Hz), 6.78 (1H, brd, J=8 Hz), 6.49 (1H, dd, J=8, 6 Hz), 6.47 (1H, dd, J=8, 3 Hz), 5.7~6.0 (1H, br), 4.10 (2H, t, J=5.5 Hz), 4.02 (1H, ddd, J=14, 9, 5.5 Hz), 3.46 (2H, brt, J=5.5 Hz), 3.2 (1H, ddd, J=14, 5.5, 4 Hz), 2.37~2.48 (1H, m), 2.22~2.33 (1H, m), 2.23 (6H, s) water content: ≦0.2%; DSC: endothermic peak 158.7° C. (10° C./min).

(6) Instead of orthophospate used in step (5), use of phosphate monohydrate also produced the compound of (5). However, when phosphate monohydrate was used at room temperature, the compound of (4), phosphate monohydrate, having an infrared spectrum different from that of compound (5) was obtained at an almost the same yield as the compound of (4). This compound was transformed to the compound of (5) under heating.

The physical properties of the compound of (4) phosphate monohydrate are as follows:
Colorless Crystals
Mp.: 140.0° C.; $^1$H-NMR(Measurement solvent: CDCl$_3$) δ: The same as the compound of (5). Water content: approximately 3%; DSC: Endothermic peak 118.2° C. (10° C./min).

Text Example 1
Ethanol Ulcer

Rats were fasted for 24 hours and orally administered with a drug. After one hour, 99.5% ethanol (1 ml/rat) was fed through oral administration. After one hour of ethanol administration, the abdomens of the rats were dissected and the size of ulcer in the gland gastric region was measured for each rat. The results are shown in Table 1.

TABLE 1

| Example | ED$_{50}$ (mg/kg) | Suppression (%) | Example | ED$_{50}$ (mg/kg) | Suppression (%) |
|---|---|---|---|---|---|
| 3 | 14 | 88 | 47 | | 100 |
| 4 | 5.3 | 85 | 68 | | 94 |
| 8 | | 86 | 70 | | 96 |
| 9 | | 85 | 86 | | 79 |
| 10 | | 82 | 95 | | 99 |
| 11 | | 96 | 97 | | 81 |
| 21 | | 99 | 106 | 8.4 | 98 |
| 23 | | 98 | 111 | | 100 |
| 26 | | 98 | 113 | | 87 |
| 28 | | 100 | 116 | | 99 |
| 33 | | 83 | 122 | | 99 |
| 35 | | 99 | 134 | | 98 |
| 41 | | 93 | 136 | | 80 |
| 43 | | 78 | 140 | | 94 |

Test Example 2
HCl-ethanol Ulcer

Rats were fasted for 24 hours and orally administered with a drug. After one hour, 60% ethanol containing 0.15 N hydrochloric acid (1 ml/rat) was perorally administered to each rat. One hour after ethanol administration, the size of ulcer in the gland gastric region was measured for evaluation of anti-ulcer effects of the drug.

TABLE 2

| Example | Suppression (%) | Example | Suppression (%) |
|---|---|---|---|
| 3 | 91 | 53 | 92 |
| 32 | 88 | 54 | 77 |
| 36 | 92 | 55 | 88 |
| 38 | 93 | 56 | 88 |
| 40 | 88 | 58 | 88 |
| 42 | 91 | 69 | 99 |
| 44 | 87 | 71 | 99 |
| 48 | 85 | 132 | 88 |
| 50 | 81 | 135 | 89 |
| 51 | 83 | 142 | 98 |
| 52 | 87 | | |

Test Example 3
Acid-secretion Suppression

Rats were fasted for 24 hours and the abdomens of the rats were dissected under anesthesia with ether. The pyloric region was ligated and a drug was administered to the duodenum. After four hours, the stomach was removed and the gastric juice was collected to evaluate the acid-secretion suppresssing effects by measuring the total acidity of the gastric juice through titration.

TABLE 3

| Example | Suppression (%) | Example | Suppression (%) |
|---|---|---|---|
| 13 | 82 | 70 | 81 |
| 21 | 76 | 95 | 90 |
| 26 | 82 | 131 | 89 |
| 43 | 80 | 134 | 87 |
| 45 | 80 | 137 | 76 |
| 61 | 87 | 140 | 85 |
| 68 | 83 | | |

Test Example 4

H/K-ATPase Inhibition

The inhibitory effect was measured under pH 7.4, by using H/K-ATPase isolated and purified from the rabbit gastric mucous membrane.

TABLE 4

| Example | $IC_{50}$ ($\mu$M) | Example | $IC_{50}$ ($\mu$M) |
|---|---|---|---|
| 4 | 7.4 | 27 | 38.0 |
| 21 | 49.4 | 28 | 79.0 |
| 22 | 190 | 29 | 5.0 |
| 23 | 230 | 70 | 1.1 |
| 24 | 130 | 86 | 1.1 |
| 25 | 140 | 140 | 2.0 |
| 26 | 2.1 | 144 | 11.4 |

Test Example 5

Anti-*Helicobacter-pylori* Action

Using clinically isolated 10 bacterial strains, the minimum inhibitory concentration (MIC) was measured according to the agar plate dilution method.

TABLE 5

| Example | MIC ($\mu$g/ml) | Example | MIC ($\mu$g/ml) |
|---|---|---|---|
| 3 | 0.78–3.13 | 77 | 6.25–12.5 |
| 4 | 25–50 | 92 | >100 |
| 8 | 1.56–6.25 | 95 | 50–>100 |
| 9 | 25–50 | 97 | 25–100 |
| 10 | 25–100 | 111 | 25 |
| 13 | 25–50 | 112 | 12.5–50 |
| 14 | 6.25–50 | 113 | 25–50 |
| 17 | 25–50 | 114 | 12.5–25 |
| 21 | 50–100 | 116 | 6.25–12.5 |
| 60 | 6.25–25 | 122 | 12.5–25 |
| 62 | 1.56–12.5 | 132 | 3.13–12.5 |
| 65 | 6.25–25 | 136 | 3.13–12.5 |
| 68 | 100–>100 | 138 | 3.13–12.5 |
| 70 | 6.25–12.5 | 144 | 25–50 |

Test Example 6

Hemolytic Action

A compound was dissolved in 1% DMSO containing saline to form a solution and to the resultant solution was added a certain amount of 10% rat red blood cell stock that had been cleansed. After incubation for 30 minutes at, 37° C., the mixture was centrifugally separated and the supernatant was obtained. The absorbance (540 nm) of the supernatant was measured. The hemolysis ratio was calculated. In calculation, hemolysis occurring in saline and that in distilled water were considered as 0% and 100%, respectively.

TABLE 6

| Example | $HC_{50}$ ($\mu$g/ml) | Example | $HC_{50}$ ($\mu$g/ml) |
|---|---|---|---|
| 3 | 72.3 | 42 | >100 |
| 21 | 71.1 | 50 | >100 |
| 22 | 55.7 | 51 | 84.6 |
| 24 | 99.6 | 57 | >100 |
| 25 | 120 | 58 | 71.2 |
| 30 | >100 | 128 | >100 |
| 32 | >100 | 129 | >100 |
| 43 | >100 | 145 | >100 |
| 40 | >100 | | | formulation examples by using the compound of Example 3 are shown below. However, the present invention is not limited by such examples. The form of formulation encompasses all physical forms applicable to drugs, and, in addition to tablets and granules, includes injections, powders capsules, suppositories, ointments, and creams.

Example 149

| <Tablets> | |
|---|---|
| The compound of Example 3 | 10 mg |
| Lactose | 118.3 mg |
| Microcrystalline cellulose | 30 mg |
| Hydroxypropyl cellulose | 0.9 mg |
| Magnesium stearate | 0.9 mg |

The above ingredients were mixed uniformly, and according to the customary method a tablet weighing 150 mg was produced.

Example 150

| <Granules> | |
|---|---|
| The compound of Example 3 | 10 mg |
| Lactose | 113.5 mg |
| Cornstarch | 70 mg |
| Hydroxypropyl cellulose | 1 mg |
| Magnesium stearate | 2.5 mg |

The above ingredients were mixed uniformly, and according to the wet or dry method granules (150 mg) are produced.

Industrial Applicability

The sulfonamide derivative (1) or a salt thereof according to the present invention exhibits radical scavenging action, gastric mucous secretion augmenting action, and anti-hp action, is effective in the treatment of experimental ulcers, and thus is effective as a peptic ulcer therapeutic agent.

What is claimed is:

1. A sulfonamide compound represented by the following formula (1):

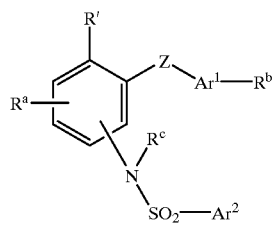
(1)

wherein Z represents an imino group, —N(R$^2$)—(CH$^2$)$_n$—, —N(R$^2$)—(CH$^2$)$_n$—N(R$^3$)—, —N(R$^2$)—(CH$^2$)$_n$—O—, —N(R$^2$)—(CH$^2$)$_n$—S—, —N(R$^2$)—(CH$^2$)$_n$—NHSO$_2$—, —N(R$^2$)—CH$_2$CH=CH—, —O(CH$_2$)—N(R$^3$)—, or —N(R$^2$)—(CH$^2$)$_n$—O—CH$_2$—;

- Ar$^1$ represents an aromatic hydrocarbon group, a saturated heterocyclic group or an unsaturated heterocyclic group selected from the group consisting of pyridyl, thienyl, furyl, quinolyl, oxazolyl, thiazolyl, thiadiazolyl, and tetrazolyl.
- Ar$^2$ represents a phenyl group, an alkyl group, a naphthyl group, a quinolyl group, an isoquinolyl group, a thienyl group, or a pyridyl group, which optionally has one through three substituents selected from among a halogen atom, an alkyl group, an alkoxy group, an acetamido group, and a nitro group;
- R$^a$ represents a hydrogen atom, a morpholinoyl group, an alkoxy group, or an aminoalkoxy group;
- R$^b$ represents a hydrogen atom, a halogen atom, an alkyl group, or an alkoxy group;
- R$^c$ represents a hydrogen atom, or an alkyl group or a halogenobenzenesulfonyl group, which optionally has a substituent;
- R$^1$ represents a hydrogen atom, or R$^1$ and R$^2$ together form a trimethylene group;
- R$^2$ represents a hydrogen atom, an alkyl group, a dialkylaminoalkyl group, a benzyl group, a halogenophenyl group, or a halogenobenzenesulfonyl group, R$^2$ and R$^1$ together form a trimethylene group, or R$^2$ and R$^3$ together for an ethanedioyl group or an alkylene group;
- R$^3$ represents a hydrogen atom, an alkyl group, a hydroxyoxalyl group, an alkanoyl group, a sulfonyl group, an alkoxycarbonyl group, or a halogenobenzenesulfonyl group, or R$^3$ and R$^2$ together form an ethanedioyl group or an alkylene group;
- n is a number of 2–4; and
- Z is not —N(R$^2$)—CH$_2$—CH=CH— when Ar$^2$ is an isoquinolyl group, or a pharmaceutically acceptable salt thereof.

2. A sulfonamide compound according to claim 1 or a pharmaceutically acceptable salt thereof, wherein R$^c$ is an alkyl group having a substituent selected from the group consisting of an amino group, a dialkylamino group, an aminoalkoxy group, a dialkylaminoalkoxy group, a heterocyclic group, and a hydroxyl group.

3. A pharmaceutical composition comprising a sulfonamide compound as recited in claim 1 or 2 or a pharmaceutically acceptable salt thereof and a pharmaceutically acceptable carrier therefor.

4. A method for treating a patient in need of treatment for a peptic ulcer comprising administration of an effective dose of a sulfonamide compound as recited in claim 1 or 2 or a pharmaceutically acceptable salt thereof.

5. A method for treating a patient in need of treatment for a Helicobacter-Pylori infection comprising administering an effective dose of sulfonamide compound as recited in claim 1 or 2 or a pharmaceutically acceptable salt thereof.

6. A sulfonamide compound according to claim 1 of the formula N-(4-chlorobenzenesulfonyl)-N-(2-dimethylaminoethyl)-N'-[2-(4-chlorophenoxy)ethyl ]-o-phenylenediamine or a pharmaceutically acceptable salt thereof.

7. N-[2-(2-Aminoethoxy)ethyl]-N-(4-chlorobenzenesulfonyl)-N'-[2-(4-chlorophenoxy)ethyl]-o-phenylenediamine or a pharmaceutically acceptable salt thereof.

8. N-(4-Chlorobenzenesulfonyl)-N-[2-(2-dimethylamino)ethoxyethyl]-N'-[2-(4-chlorophenoxy)ethyl]-o-phenylenediamine or a pharmaceutically acceptable salt thereof.

* * * * *

UNITED STATES PATENT AND TRADEMARK OFFICE
CERTIFICATE OF CORRECTION

PATENT NO. : 6,403,607 B1
DATED : June 11, 2002
INVENTOR(S) : Hiroyoshi Hidaka et al.

It is certified that error appears in the above-identified patent and that said Letters Patent is hereby corrected as shown below:

Column 47,
Line 5,

" 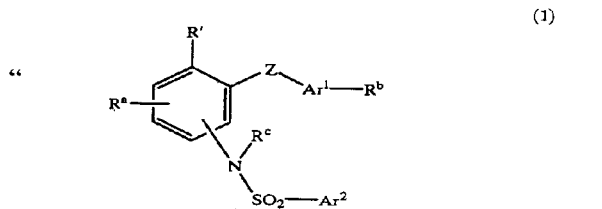 "

should read -- 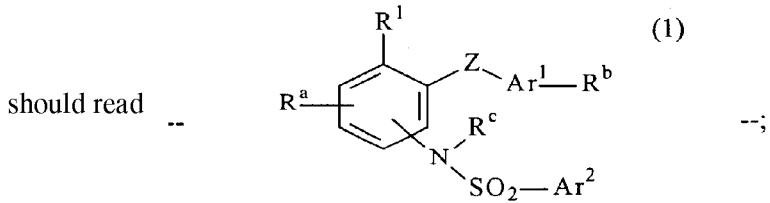 --;

Lines 13-17, "--CH$^2$--" should read -- --CH$_2$-- --, each occurrence;
Line 44, "for" should read -- form --.

Signed and Sealed this

Thirteenth Day of May, 2003

JAMES E. ROGAN
*Director of the United States Patent and Trademark Office*